US011834688B2

(12) United States Patent
Qin et al.

(10) Patent No.: US 11,834,688 B2
(45) Date of Patent: Dec. 5, 2023

(54) LIGASE FUSION PROTEINS AND APPLICATION THEREOF

(71) Applicant: GENEQUANTUM HEALTHCARE (SUZHOU) CO., LTD., Suzhou (CN)

(72) Inventors: Gang Qin, Suzhou (CN); Cao Lv, Suzhou (CN); Joachim Walter, Mittelbiberach (DE); Rolf Werner, Biberach an der Riss (DE); Yunpeng Zhong, Suzhou (CN)

(73) Assignee: GENEQUANTUM HEALTHCARE (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 17/815,371

(22) Filed: Jul. 27, 2022

(65) Prior Publication Data

US 2023/0097252 A1 Mar. 30, 2023

Related U.S. Application Data

(62) Division of application No. 17/374,262, filed on Jul. 13, 2021, now Pat. No. 11,453,870.

(30) Foreign Application Priority Data

Jan. 28, 2021 (WO) ................ PCT/CN2021/074082

(51) Int. Cl.
| | | |
|---|---|---|
| *C12N 9/52* | (2006.01) | |
| *A61K 47/68* | (2017.01) | |
| *C12N 11/06* | (2006.01) | |
| *A61K 47/60* | (2017.01) | |

(52) U.S. Cl.
CPC ............... *C12N 9/52* (2013.01); *A61K 47/60* (2017.08); *A61K 47/6801* (2017.08); *A61K 47/6817* (2017.08); *C12N 11/06* (2013.01); *C12Y 304/2207* (2013.01); *C07K 2319/61* (2013.01)

(58) Field of Classification Search
CPC . C12N 9/52; C12N 11/06; C12N 9/50; C12N 11/04; C12N 11/087; A61K 47/60; A61K 47/6801; A61K 47/6817; A61K 47/6803; A61K 47/6855; A61K 47/6889; C12Y 304/2207; C07K 2319/61; C07K 2319/20; C07K 1/18; C07K 1/22; C07K 2319/00; C12P 21/02; C12P 21/06
See application file for complete search history.

(56) References Cited

U.S. PATENT DOCUMENTS

| | | | |
|---|---|---|---|
| 7,238,489 B2 | 7/2007 | Schneewind et al. | |
| 7,429,472 B2 | 9/2008 | Darzins et al. | |
| 7,888,086 B2 | 2/2011 | Darzins et al. | |
| 8,202,700 B2 | 6/2012 | Darzins et al. | |
| 11,453,870 B2 | 9/2022 | Qin et al. | |
| 2006/0024808 A1 | 2/2006 | Darzins et al. | |
| 2006/0229253 A1 | 10/2006 | Doronina et al. | |
| 2011/0321183 A1 | 12/2011 | Ploegh et al. | |
| 2014/0120035 A1 | 5/2014 | Govindan et al. | |
| 2016/0032346 A1 | 2/2016 | Tsourkas et al. | |
| 2016/0193355 A1 | 7/2016 | Qin et al. | |
| 2016/0297890 A1 | 10/2016 | Agatsuma et al. | |
| 2017/0112944 A1 | 4/2017 | Qin et al. | |
| 2020/0277403 A1 | 9/2020 | Tsourkas et al. | |
| 2021/0187114 A1 | 6/2021 | Qin et al. | |

FOREIGN PATENT DOCUMENTS

| | | |
|---|---|---|
| CN | 106237341 | 12/2016 |
| EP | 3647419 A1 | 5/2020 |
| WO | WO 2004/072232 | 8/2004 |
| WO | WO 2005/054821 | 6/2005 |
| WO | WO 2006/093529 | 9/2006 |
| WO | WO 2008/054821 | 5/2008 |
| WO | WO 2014/140317 | 9/2014 |
| WO | WO 2014/177042 | 11/2014 |
| WO | WO 2014/183066 | 11/2014 |
| WO | WO 2015/165413 | 11/2015 |
| WO | WO 2016/014501 | 1/2016 |
| WO | WO 2017/167712 A1 | 10/2017 |
| WO | WO 2020/072764 A1 | 4/2020 |

OTHER PUBLICATIONS

Warden_Rothman et al., Analytical Chemistry, 2013, 85, 11090-11097 (Year: 2013).*
Buckley, D. et al., "HaloPROTACS: Use of Small Molecule PROTACs to Induce Degradation of HaloTag Fusion Proteins," ACS Chemical Biology, 2015, 10, 1831-1837.
Guimaraes, C. et al., "Site-specific C-terminal and Internal Loop Labeling of Proteins Using Sortase-mediated Reactions," Nature Protocols, 2013, 8 (9), 1787-1799.
Hirakawa, H. et al., "Artificial Protein Complexes for Biocatalysis," Topics in Catalysis, 2012, 55, 1124-1137.
Hoelzel, C. et al., "Visualizing and Manipulating Biological Processes Using HaloTag and SNAP-Tag Technologies," HHS Public Access, Author Manuscript, available in PMC 2020, 31 pages, face of article states: Published in final edited form as: Chembiochem. 2020; 21(14), 1935-1946, doi:10.1002/cbic.202000037.

(Continued)

*Primary Examiner* — Sudhakar Katakam

(74) *Attorney, Agent, or Firm* — Hoxie & Associates LLC

(57) ABSTRACT

The present disclosure relates to the field of biotechnology. In particular, provided are a ligase fusion protein and an immobilized ligase comprising the same. Also provided is use of the ligase fusion protein or the immobilized ligase in the preparation of conjugates. Further provided is a process for the preparation of conjugates using a ligase or a ligase unit.

28 Claims, 11 Drawing Sheets

Specification includes a Sequence Listing.

(56) References Cited

OTHER PUBLICATIONS

Ke, N. et al., "Visualization of Periplasmic and Cytoplasmic Proteins with a Self-labeling Protein Tag," Journal of Bacteriology, 2016, 198 (7), 1035-1043.

Li, A. et al., "Research Progress of Microbial Haloalkane Dehalogenase—A Review," Wei Sheng Wu Xue Bao (Acta Microbiologica Sinica), 2015, 55 (4), 381-388, Abstract only.

Beerli, et al., "Sortase Enzyme-Mediated Generation of Site-Specifically Conjugated Antibody Drug Conjugates with High In Vitro and In Vivo Potency", *PLOS ONE*, vol. 10, No. 7, pp. e0131177, (2015).

Bradshaw, et al., "Molecular Features of the Sortase Enzyme Family", *FEBS Journal*, (2015), 282: 2097-2114.

Carillo, et al., "The Multiple Sequence Alignment Problem in Biology", *SIAM J Applied Math*, (1988), 48:1073-1082.

Dramsi, et al., "Sorting Sortases: a Nomenclature Proposal for the Various Sortases of Gram-Positive Bacteria", *Research in Microbiology*, 156: 289-297, (2005). Abstract Only.

Fernandez-Suarez, et al., "Protein-Protein Interaction Detection in Vitro and in Cells by Proximity Biotinylation", vol. 130, No. 29, pp. 9251-9253, (2008).

Gao, et al., "Recent Advances in Site Specific Conjugations of Antibody Drug Conjugates (ADCs)", *Current Cancer Drug Targets*, vol. 16, No. 6, pp. 469-479(11), (2016). Abstract Only.

Hay, et al., "In vivo polyester immobilized sortase for tagless protein purification", *Microbial Cell Factories*, vol. 14, No. 1, pp. 190, (2015).

Malik, et al., "A Comprehensive in Silico Analysis of Sortase Superfamily", *J Microbiol.*, (2019), 57(6): 431-443.

Smith, D.W., *Biocomputing: Informatics and Genome Projects*, Academic Press, New York, (1993).

Warden-Rothman, et al., "Sortase-Tag Expressed Protein Ligation: Combining Protein Purification and Site-Specific Bioconjugation into a Single Step", *Analytical Chemistry*, vol. 85, No. 22, pp. 11090-11097, (2013).

Witte, et al., "Site-Specific Protein Modification Using Immobilized Sortase in Batch and Continuous-Flow Systems", *Nat. Protoc.*, 35 (2015), 10(3): 508-516.

Zhao, et al., "One-Step Purification and Immobilization of Extracellularly Expressed Sortase A by Magnetic Particles to Develop a Robust and Recyclable Biocatalyst", *Sci. Rep.*, (2017), 7: 6561.

\* cited by examiner

A

B

C

LIGASE FUSION PROTEINS AND APPLICATION THEREOF

CROSS-REFERENCE TO RELATED APPLICATIONS

This application is a divisional application of U.S. application Ser. No. 17/374,262, filed on Jul. 13, 2021, which claims the benefit of International Application No PCT/CN2021/074082, filed on Jan. 28, 2021, the disclosures of which are incorporated herein by reference in their entireties.

REFERENCE TO AN ELECTRONIC SEQUENCE LISTING

The contents of the electronic sequence listing (sequence-listing.xml; Size:40,386 bytes; and Date of Creation: Jul. 26, 2022) are herein incorporated by reference in its entirety.

TECHNICAL FIELD

The present disclosure relates to the field of biotechnology, in particular to a ligase fusion protein and an immobilized ligase comprising the same. Also provided is use of the ligase fusion protein or the immobilized ligase in the preparation of conjugates. Further provided is a process for the preparation of conjugates using a ligase or a ligase unit.

BACKGROUND

Demands for high-quality conjugates, especially bioconjugates, such as those for bioscience research, diagnosis or therapeutics purposes, are increasing rapidly. However, the high-throughput production of bioconjugates is far from satisfying, partially because that the complex nature of biomolecules makes the high-quality standards for bioconjugates difficult to be met.

Conventional conjugation process is chemistry based. For example, in a typical process for antibody-drug conjugate (ADC) production, the drug is chemically conjugated to lysine or cysteine residue in the antibody via a linker. The antibody is prepared through upstream and downstream purification processes before entering the conjugation process. After the conjugation step, another downstream purification process is required to remove the aggregates, solvents, by-products and impurities from the ADC. The multiple downstream steps along the process from antibody preparation to ADC production significantly increase cost and time, and simultaneously lower the yield. Moreover, the conjugation reaction has to be conducted in chemical isolators for safety reasons, making the process difficult to scale up. Overall, the conventional processes involve multiple upstream and downstream purification steps, which are time-consuming, uneconomic, inflexible and lack scalability.

Ligases, such as Sortase enzymes are applied to catalyze conjugation in a highly substrate-specific and efficient manner under mild conditions (e.g., WO2015/165413A1, WO2014/177042 and WO2014/140317), which may reduce time, cost, and waste. Despite the many advantages, however, industrial application of ligases for conjugation is still limited due to several challenges.

Challenges such as low operational stability and reusability of the enzymes may be somewhat overcome by enzyme immobilization. Immobilized sortase A on cyanogen-bromide activated Sepharose (see, e.g., Witte et al., Site-specific protein modification using immobilized sortase in batch and continuous-flow systems, Nat Protoc, (2015), 10(3): 508-516) or His$_6$-tagged sortase A immobilized on nickel-modified magnetic particles (see, e.g., Zhao et al., One-step purification and immobilization of extracellularly expressed sortase A by magnetic particles to develop a robust and recyclable biocatalyst, Sci Rep, (2017), 7: 6561) has been employed for conjugation.

However, removal of residual enzyme contaminants carried over from the upstream catalytic reaction remains a major concern for most enzyme-catalyzed conjugates, especially for bioconjugates, because residual enzyme contaminants (in the case of immobilized enzyme, free enzymes non-specifically adsorbed on the support may still fall off) can be difficult to remove. Therefore, there is a need for ligases that are cost efficient, stable, controllable and easily removable from the conjugate product.

SUMMARY

In a general aspect, provided is a ligase fusion protein comprising a ligase and a Halo tag.

In some embodiments, the ligase is a transpeptidase. In some embodiments, the ligase is a sortase. In some embodiments, the ligase is a sortase A. In some preferred embodiments, the sortase A comprises an amino acid sequence selected from the group consisting of SEQ ID NOs: 1-26 or an amino acid sequence having a sequence identity of at least about 85%, at least about 90%, at least about 95%, or at least about 99% thereto. In some other preferred embodiments, the sortase A comprises amino acid substitutions of SNAT, YNAT, WNDT or VNNS at positions 34, 100, 105 and 136, preferably, the sortase A comprises the amino acid sequence of SEQ ID NO: 27 or an amino acid sequence having a sequence identity of at least about 85%, at least about 90%, at least about 95%, or at least about 99% thereto.

In an embodiment, the Halo tag is a mutant haloalkane dehalogenase or a variant thereof that removes the halogen from a haloalkyl substrate and forms a covalent linkage with the remaining alkyl group. In some embodiments, the Halo tag comprises the amino acid sequence of SEQ ID NO: 28 or an amino acid sequence having a sequence identity of at least about 85%, at least about 90%, at least about 95%, or at least about 99% thereto.

In a preferable aspect, provided is a ligase fusion protein having an altered isoelectric point (pI) compared to the ligase from which it is derived, wherein the ligase has an alkaline pI and the Halo tag has an acidic pI. In some embodiments, the ligase has an isoelectric point (pI) of about 7.5 to about 10.0, the Halo tag has an isoelectric point of about 4.5 to about 5.0, and the pI of the ligase fusion protein is about 2.0 to about 4.5 pH units lower than that of the ligase.

In another general aspect, provided is an immobilized ligase, comprising the ligase fusion protein according to the present disclosure immobilized to a support.

Also provided is use of the ligase fusion protein or the immobilized ligase according to the present disclosure in the preparation of a conjugate.

In yet another general aspect, provided is a process for the preparation of a conjugate comprising a first moiety and a second moiety, comprising the steps of:

(a) providing System 1 comprising the first moiety and providing System 2 comprising the second moiety; and (b) contacting a ligase unit with System 1 and System 2 in step (a) to catalyze the conjugation reaction between the first moiety and second moiety to obtain the conjugate, wherein the ligase unit comprises a ligase, the first moiety and the second moiety each independently comprises a biomolecule, a protein, an antibody, an antibody fragment, a receptor, a signal transduction factor, a cell growth factor, a nucleic acid or a nucleic acid analogue, a small molecule compound, a glycan, a PEG moiety, a radionuclide, a cytokine, an immunomodulator, a tracer molecule, a fluorophore, a fluorescent molecule, a peptide, a polypeptide, or a peptidomimetic; and one of the first moiety and the second moiety further comprises the recognition motif of the ligase donor substrate, and the other one of the first moiety and the second moiety comprises the recognition motif of the ligase acceptor substrate.

In some embodiments, the ligase unit comprises a free ligase, preferably a transpeptidase, more preferably a sortase, even more preferably a sortase A, most preferably the ligase unit comprises the ligase fusion protein according to the present disclosure.

In some other embodiments, the ligase unit comprises a ligase immobilized to a support, preferably, the ligase is covalently immobilized to the support, preferably the ligase is a transpeptidase, more preferably a sortase, even more preferably a sortase A, most preferably the ligase unit comprises the immobilized ligase according to the present disclosure.

In some embodiments, at least one of System 1 and System 2 in step (a) comprises one or more impurities. In some other embodiments, at least one of System 1 and System 2 in step (a) is a harvested clarified cell culture fluid (HCCF).

In some embodiments, the process further comprises the steps of
(1) subjecting System 1 in step (a) before step (b), and/or
(2) subjecting System 2 in step (a) before step (b), and/or
(3) subjecting the conjugate obtained in step (b),
to one or more chromatography steps to remove one or more impurities.

The chromatography step can be independently selected from the group consisting of affinity chromatography, hydrophobic interaction chromatography, ion exchange chromatography, mixed mode chromatography, hydroxyapatite chromatography and a combination thereof. Preferably, the chromatography step is selected from affinity chromatography, ion exchange chromatography, and a combination thereof.

In some embodiments, at least one of the first moiety and the second moiety comprises an antibody or an antibody fragment, and at least one of steps (1)-(3) comprises an affinity chromatography; preferably, the antibody or antibody fragment comprises an Fc fragment, and the affinity chromatography is Protein A affinity chromatography.

DETAILED DESCRIPTION

General Definitions

Figure 1:
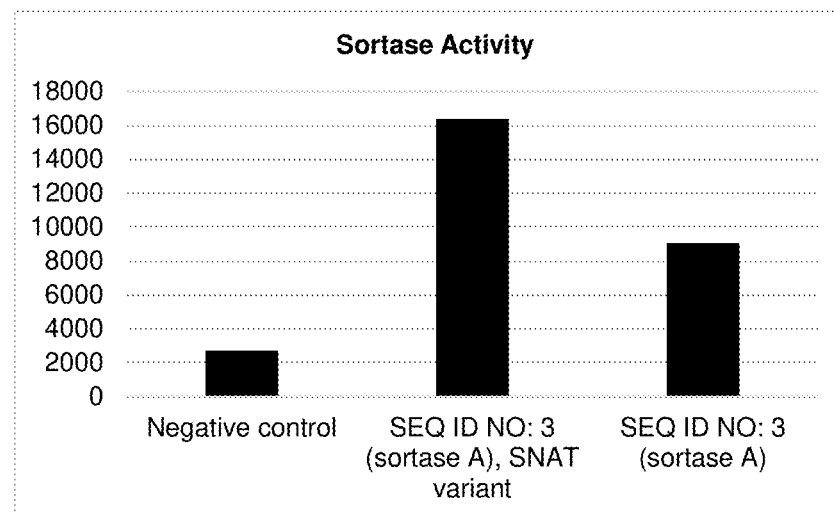
FIG. 1 depicts the sortase activities of an exemplary SrtA derived from *Staphylococcus warneri* (SEQ ID NO: 3) and its SNAT variant.

Unless defined otherwise, all technical and scientific terms used herein have the same meaning as is commonly understood by one of skill in the art. In addition, the terms and experimental procedures relating to protein and nucleic acid chemistry, molecular biology, cell and tissue culture, microbiology and immunology are those terms and common procedures widely used in the art. When a trade name is present herein, it refers to the corresponding commodity or the active ingredient thereof. All patents, published patents applications and publications cited herein are hereby incorporated by reference. Meanwhile, for better understanding of the present disclosure, definitions and explanations of relevant terms are provided below.

As used herein, the expression "at least one" or "one or more" refers to one, two, three, four, five, six, seven, eight, nine or more, one hundred, two hundred, three hundred, four hundred, five hundred, six hundred, seven hundred, eight hundred, nine hundred or more, etc. As used herein, "a" and "an" unless clearly indicated to the contrary, should be understood to mean "at least one".

When a certain amount, concentration, or other value or parameter is set forth in the form of a range, a preferred range, or a preferred upper limit or a preferred lower limit, it should be understood that it is equivalent to specifically revealing any range formed by combining any upper limit or preferred value with any lower limit or preferred value, regardless of whether the said range is explicitly recited. Unless otherwise stated, the numerical ranges listed herein are intended to include the endpoints of the range and all integers and fractions (decimals) within the range. For example, the expression "i" is an integer of 2 to 20" means that i is any integer of 2 to 20, for example, i can be 2, 3, 4, 5, 6, 7, 8, 9, 10, 11, 12, 13, 14, 15, 16, 17, 18, 19 or 20. Other similar expressions should also be understood in a similar manner.

The terms "about" and "approximately", when used in connection with a numerical variable, such as a concentration, an isoelectric point (pI), a pH, a temperature or a certain range, generally mean that the value of the variable and all values of the variable are within experimental error (for example, within a 95% confidence interval for the mean) or within ±10% of a specified value, or a wider range.

The term "optional" or "optionally" means the event described subsequent thereto may, but not necessarily happen, and the description includes the cases wherein the said event or circumstance happens or does not happen.

The expression "comprising" or similar expressions "including", "containing" and "having" are open-ended, and do not exclude additional unrecited elements, steps, or ingredients. The expression "consisting of" excludes any element, step, or ingredient not designated. The expression "consisting essentially of" means that the scope is limited to the designated elements, steps or ingredients, plus elements, steps or ingredients that are optionally present that do not substantially affect the essential and novel characteristics of the claimed subject matter. It should be understood that the expression "comprising" encompasses the expressions "consisting essentially of" and "consisting of".

As used here, the definition of "biomolecule" encompasses proteins, nucleic acids, lipids, carbohydrates, small nucleotides, amino acids and derivatives thereof.

As used herein, a "nucleic acid" or a "polynucleotide" refers to a polymer of at least two nucleotides or nucleotide derivatives joined together by phosphodiester bonds, including deoxyribonucleic acid (DNA) and ribonucleic acid (RNA).

As used herein, a "vector" is a vehicle used to transfer exogenous nucleic acids into a host cell, where the exogenous nucleic acids are amplified or expressed. As used herein, the definition of "vector" encompasses plasmids, linearized plasmids, viral vectors, cosmids, phage vectors, phagemids, artificial chromosomes (e.g., yeast artificial chromosomes and mammalian artificial chromosomes), etc. As used herein, a vector could be expressible and/or replicable inside a host cell, meaning that the vector is able to express RNA polynucleotides or polypeptides and/or to produce multiple copies of the vector in the host cell. To be "expressible" or "replicable", a vector could comprise nucleic acid sequences or elements operably linked to a promoter. As used herein, "operably linked" with reference to nucleic acid sequences or elements means that these nucleic acid sequences are functionally related to each other. For example, a promoter can be operably linked to a nucleic acid sequence encoding a polypeptide, whereby the promoter regulates or mediates the transcription of the nucleic acid. Those skilled in the art could select and use appropriate vectors for a particular purpose.

As used herein, "peptide", "polypeptide" or "protein" refers to two or more amino acids covalently joined. Unless otherwise specified, these terms are interchangeably.

As used herein, "sequence identity" has an art-recognized meaning and the percent of sequence identity between two polypeptides can be calculated by aligning the two sequences using publicly available algorithms, such as the Basic Local Alignment Search Tool (BLAST) and the Fast Adaptive Shrinkage/Thresholding Algorithm (FASTA) (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994). While there are a number of methods to measure identity between two polypeptides, the term "identity" is well known to skilled artisans (Carrillo, H. & Lipman, D., *SIAM J Applied Math* 48:1073 (1988)).

As used herein, the term "variant" refers to a protein having substitutions, deletions, insertions of one or more residues when compared to a reference protein. The reference protein can be a naturally occurring protein that can be isolated from natural source (i.e., a wild-type protein) or an engineered protein. As used herein, the function or activity of a variant, such as a sortase A variant or a Halo tag variant, is substantially similar with or comparable to or higher than that of the reference sortase A or Halo tag, respectively.

In the context of the present specification, the positions of amino acids in a protein are defined as follows: (i) starting from the N-terminus; and (ii) the position of the $1^{st}$ amino acid from the N-terminus is designated as 1. An amino acid (such as Ser) at a given position (such as position 34) can be expressed as Ser34. An amino acid (such as His) at a given amino acid position (such as position 272) substituted with another amino acid (such as Phe) can be expressed as His272Phe.

As used herein, a "ligase" refers to an enzyme that can catalyze the covalent linkage of two or more molecules. A ligase can specifically catalyze the conjugation between a first moiety comprising the recognition motif of the ligase donor substrate and a second moiety comprising the recognition motif of the ligase acceptor substrate to produce a target conjugate.

As used here, the term "transpeptidation reaction" refers to a chemical reaction in which one or more amino acids (such as a peptide) is transferred from one molecule to another molecule. A transpeptidase is an enzyme that is able to catalyze a transpeptidation reaction between a donor substrate and an acceptor substrate. In a simplified transpeptidation reaction catalyzed by a sortase, the sortase first cleaves the recognition motif of a ligase donor substrate (also referred to as a donor recognition motif, such as LPXTG, when SrtA is used) to form a substrate-enzyme intermediate through formation of a thioester bond; next, the recognition motif of a ligase acceptor substrate (also referred to as an acceptor recognition motif, such as GGG) nucleophilically attacks the thioester bond to release the enzyme and form a new peptide bond between the two substrates. A transpeptidation reaction often results in conjugation of two parties to form a conjugate.

As used herein, the term "conjugation" refers to the covalent linkage of at least two parties (e.g., at least two molecules or at least two ends of the same molecule).

As used herein, a "conjugate" can be prepared from at least two parties (e.g., at least two molecules or at least two ends/side chains of the same molecule) through covalent linkage.

As used herein, a "bioconjugate" refers to a conjugate with at least one of the conjugated parties being a biomolecule. Examples of bioconjugates include therapeutic molecules conjugated to polymer, lipid, antibody, peptide, aptamer, or small molecular ligands, such as siRNA conjugates, peptide hormone conjugates, peptide-peptide conjugates, peptide-drug conjugates, antibody-drug conjugates and multispecific antibodies, or the like.

The term "targeting molecule" refers to a molecule that has an affinity for a particular target (e.g., receptor, cell surface protein, cytokine, etc.). A targeting molecule can deliver the payload to a specific site in vivo through targeted delivery. A targeting molecule can recognize one or more targets. The specific target sites are defined by the targets it recognizes. For example, a targeting molecule that targets a receptor can deliver a cytotoxin to a site containing a large number of the receptor. Examples of targeting molecules include, but are not limited to antibodies, antibody fragments, binding proteins for a given antigen, antibody mimics, scaffold proteins having affinity for a given target, ligands, and the like.

As used herein, the term "antibody-drug conjugate (ADC)" refers to a conjugate comprising an antibody or an antibody fragment coupled to a payload covalently.

As used herein, the terms "activity", "enzymatic activity" and "catalytic activity" of a ligase (such as a sortase) refer to the ability of the ligase to catalyze a conjugation reaction and can be used interchangeably. As used herein, the catalytic activity of a sortase in a conjugation reaction, for example, a conjugation reaction between an antibody and a payload, can be expressed as conjugation efficiency (conjugation efficiency=(molars of conjugated antibody: molars of total antibody)×100%) or DAR (Drug-to-Antibody Ratio, average drug to antibody ratio for a given preparation of antibody drug conjugate) distribution.

As used herein, the term "antibody (Ab)" is an immunoglobulin (Ig) molecule or a derivative thereof that specifically binds to an antigen through at least one antigen-binding site. A "conventional" or "full-length" antibody typically consists of four polypeptides: two heavy chains (HC) and two light chains (LC). As used herein, the definition of "antibody" encompasses conventional antibodies, recombinant antibodies, multispecific antibodies (e.g., bispecific antibodies), fully human antibodies, non-human antibodies, humanized antibodies, chimeric antibodies, intrabodies, diabodies, nanobodies (i.e., single-domain antibodies, VHH domains), and anti-idiotypic antibodies. Also contemplated are members of any immunoglobulin type (e.g., IgG, IgM, IgD, IgE, IgA and IgY), any class (e.g. IgG1, IgG2, IgG3, IgG4, IgA1 and IgA2) or subclass (e.g., IgG2a and IgG2b), or any derivatives thereof.

As used herein, an "antibody fragment" of an antibody refers to any portion of an antibody comprising fewer amino acid residues than a full-length antibody, such as an antigen-binding fragment that contains at least a portion of the variable domains (e.g. one or more CDRs) of the antibody and specifically binds to the same cognate antigen as the full-length antibody, or an Fc fragment that contains heavy chain constant regions of the antibody and binds to Fc receptors on the cell surface. Antibody fragments can be obtained by various methods, such as chemical or enzymatic treatment, chemical synthesis or recombinant DNA technology. Examples of antibody fragments include, but are not limited to, Fv (the fragment variable region), scFv (single-chain Fv fragment), dsFv (disulfide-stabilized variable fragment), scdsFv (single-chain disulfide-stabilized variable fragment), diabody, Fd (the fragment difficult), Fab (the fragment antigen binding), scFab (single-chain Fab), Fab', F(ab')2, Fc (the fragment crystallizable region) and any derivatives thereof.

As used herein, the term "payload" refers to a functional moiety which is comprised in a conjugate, for example, linked via a linker. Examples of payload include, but are not limited to, small molecule compounds (also referred to as small molecule drugs, e.g., inhibitors and toxins (such as cytotoxins)), radionuclides (e.g., $^{225}$Ac, $^{211}$At, $^{212}$Bi, $^{213}$Bi, $^{67}$Ga, $^{123}$I, $^{124}$I, $^{125}$I, $^{131}$I, $^{111}$In, $^{177}$Lu, $^{191m}$Os, $^{195m}$Pt, $^{186}$Re, $^{188}$Re, $^{119}$Sb, $^{153}$Sm, $^{99m}$Tc, $^{227}$Th and $^{90}$Y), glycans, PEG moieties, nucleic acids and analogues (e.g., interfering RNAs), tracer molecules (e.g., fluorophores and fluorescent molecules), polypeptides (e.g., protein tags, bioactive peptides, enzymes, antibodies and antibody fragments, and protein toxins) and peptidomimetics. As used herein, payloads comprising a linker (such as a linker comprising a recognition motif of the ligase substrate) and a payload as described above are considered.

As used herein, the term "natural amino acid" refers to an amino acid that is a protein constituent amino acid, including the common twenty amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine), and the less common selenocysteine and pyrrolysine.

As used here, the term "unnatural amino acid" refers to an amino acid that is not a protein constituent amino acid. In particular, the term refers to an amino acid that is not a natural amino acid as defined above.

As used herein, the term "peptidomimetic" refers to a compound that mimics the conformation and desirable features of a particular peptide.

As used herein, a "receptor" refers to a structure inside or on the surface of a cell that binds a specific substance and causes a specific effect in the cell. Receptors may include T-cell receptors, B-cell receptors, and receptors of signaling molecules, cell growth factors and cytokines as described herein.

As used herein, a "signal transduction factor" refers to any substance that plays a role in a signal transduction event across or through a cell. Signal transduction factors may include, but not limited to, signaling molecules (such as steroid hormones, retinoic acid, thyroid hormone, vitamin D3, peptide hormones, neuropeptides, eicosanoids, neurotransmitters and cytokines) and receptors thereto.

As used herein, the term "immunomodulator" refers to a biologically active substance that is capable of affecting the functioning of the immune system. An immunomodulator can be immunosuppressive (such as an immunosuppressant/immunosuppressive agent) or immunostimulatory (such as an immunostimulant/immunostimulator). Examples of immunomodulators may include, but are not limited to, cytokines, thymus hormones (e.g., thymulin, thymosin and thymopoietin), lentinan, β-glucans, inulin, levamisole, isoprinosine, IMPDH inhibitors (e.g., azathioprine, leflunomide, mycophenolic acid, mizoribine, ribavirin, and tiazofurin), calcineurin inhibitors (e.g., cyclosporine and tacrolimus), mTOR inhibitors (e.g., sirolimus and everolimus), P38 inhibitors, NF-κB inhibitors (e.g., bortezomib), corticosteroids (e.g., prednisone, budesonide and prednisolone), Janus kinase inhibitors (e.g., tofacitinib and baricitinib), anti-cytokine antibodies and antibodies against T-cell receptors.

As used herein, the term "cell growth factor" refers to any substance that is capable of stimulating cellular growth, healing, proliferation, survival and differentiation. Examples of growth factors may include, but are not limited to, epidermal growth factor (EGF), fibrablast growth factor (FGF), transforming growth factor (TGF), platelet-derived growth factor (PDGF), teratocarcinoma-derived growth factor (TDGF), insulin-like growth factor (IGF), nerve growth factor (NGF), vascular endothelial growth factor (VEGF) and erythropoietin (EPO).

As used herein, the term "cytokine" refers to any substance released by the cells of the immune system and having an effect on other cells. Examples of cytokines may include chemokines, lymphokines, colony-stimulating factors (CSFs), monocyte chemoattractant proteins (MCPs), angiogenesis factors, interleukins, interferons, tumor necrosis factors (TNFs), growth factors, and other secreted and cell surface molecules that transmit signals to other cells. Cytokines include, but are not limited to, INFα, INFβ, INFγ, IL-1, IL-2, IL-4 IL-6, IL-8/CXCL8 IL-10, IL-12, IL-13, IL-15, IL-17, IL-18, IL-23, IP-10/CXCL10, eotaxin/CCL11, MCP-1/CCL2, MIP-1α/CCL4, RANTES/CCL5, TNFα, TNFβ, and growth factors.

A small molecule compound refers to a molecule with a size comparable to that of an organic molecule commonly used in medicine. The term does not encompass biological macromolecules (e.g., proteins, nucleic acids, etc.), but encompasses low molecular weight peptides or derivatives thereof, such as dipeptides, tripeptides, tetrapeptides, pentapeptides, and the like. Typically, the molecular weight of the small molecule compound can be, for example, about 100 to about 2000 Da, about 200 to about 1000 Da, about 200 to about 900 Da, about 200 to about 800 Da, about 200 to about 700 Da, about 200 to about 600 Da, about 200 to about 500 Da. As used herein, a small molecule compound may also be known as a drug.

Cytotoxin refers to a substance that inhibits or prevents the expression activity of a cell, cellular function, and/or causes destruction of cells. In some cases, the cytotoxins currently used in ADCs may be more toxic than commonly used chemotherapeutic drugs. Examples of cytotoxins include, but are not limited to, drugs that target the following targets: microtubule cytoskeleton, DNA, RNA, kinesin-mediated protein transport, regulation of apoptosis. The drug that targets microtubule cytoskeleton may be, for example, a microtubule-stabilizing agent or a tubulin polymerization inhibitor. Examples of microtubule-stabilizing agents include but are not limited to taxanes. Examples of tubulin polymerization inhibitors include but are not limited to maytansinoids, auristatins, vinblastines, colchicines, and dolastatins. The DNA-targeting drug can be, for example, a drug that directly disrupts the DNA structure or a topoisomerase inhibitor. Examples of drugs that directly disrupt DNA structure include but are not limited to DNA double strand breakers, DNA alkylating agents, DNA intercalators. The DNA double strand breakers can be, for example, an enediyne antibiotic, including but not limited to dynemicin, esperamicin, neocarzinostatin, uncialamycin, and the like. The DNA alkylating agent may be, for example, a DNA bis-alkylator (i.e. DNA-cross linker) or a DNA mono-alkylator. Examples of DNA alkylating agents include but are not limited to pyrrolo[2,1-c][1,4]benzodiazepine (PBD) dimer, 1-(chloromethyl)-2,3-dihydrogen-1H-benzo[e]indole (CBI) dimer, CBI-PBD heterodimer, dihydroindolobenzodiazepine (IGN) dimer, duocarmycin-like compound, and the like. Examples of topoisomerase inhibitors include but are not limited to camptothecins and anthracyclines. The RNA-targeting drug may be, for example, a drug that inhibits splicing, and examples thereof include but are not limited to pladienolide. Drugs that target kinesin-mediated protein transport can be, for example, mitotic kinesin inhibitors including, but not limited to, kinesin spindle protein (KSP) inhibitors.

A spacer is a structure that is located between different structural modules and can spatially separate the structural modules. The definition of spacer is not limited by whether it has a certain function or whether it can be cleaved or degraded in vivo. Examples of spacers include but are not limited to amino acids and non-amino acid structures, wherein non-amino acid structures can be, but are not limited to, amino acid derivatives or analogues. "Spacer sequence" refers to an amino acid sequence serving as a spacer, and examples thereof include but are not limited to a single amino acid such as Leu, Gln, etc., a sequence containing a plurality of amino acids, for example, a sequence containing two amino acids such as GA, etc., or, for example, GGGS, GGGGSGGGGS, etc. Other examples of spacers include, for example, self-immolative spacers such as PAB (p-aminobenzyl), and the like.

The term "alkyl" refers to a straight or branched saturated aliphatic hydrocarbon group consisting of carbon atoms and hydrogen atoms, which is connected to the rest of the molecule through a single bond. The alkyl group may contain 1 to 20 carbon atoms, referring to $C_1$-$C_{20}$ alkyl group, for example, $C_1$-$C_4$ alkyl group, $C_1$-$C_3$ alkyl group, $C_1$-$C_2$ alkyl, $C_3$ alkyl, $C_4$ alkyl, $C_3$-$C_6$ alkyl. Non-limiting examples of alkyl groups include but are not limited to methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethyl butyl, 1,1-dimethylbutyl, 2,3-dimethylbutyl, 1,3-dimethylbutyl or 1,2-dimethylbutyl, or their isomers. A bivalent radical refers to a group obtained from the corresponding monovalent radical by removing one hydrogen atom from a carbon atom with free valence electron(s). A bivalent radical have two connecting sites which are connected to the rest of the molecule. For example, an "alkylene" or an "alkylidene" refers to a saturated divalent hydrocarbon group, either straight or branched. Examples of alkylene groups include but are not limited to methylene (—$CH_2$—), ethylene (—$C_2H_4$—), propylene (—$C_3H_6$—), butylene (—$C_4H_8$—), pentylene hexylene (—$C_6H_{12}$—), 1-methylethylene (—$CH(CH_3)CH_2$—), 2-methylethylene (—$CH_2CH(CH_3)$—), methylpropylene, ethylpropylene, and the like.

As used herein, when a group is combined with another group, the connection of the groups may be linear or branched, provided that a chemically stable structure is formed. The structure formed by such a combination can be connected to other moieties of the molecule via any suitable atom in the structure, preferably via a designated chemical bond. For example, when describing a combination of a $C_{1-4}$ alkylene with one of the groups including —CH$_2$—, —NH—, —(CO)—, —NH(CO)—, —(CO)NH—, the C$_{1-4}$ alkylene may form a linear connection with the above groups, such as C$_{1-4}$ alkylene-CH$_2$—, C$_{1-4}$ alkylene-NH—, C$_{1-4}$ alkylene-(CO)—, C$_{1-4}$ alkylene-NH(CO)—, C$_{1-4}$ alkylene-(CO)NH—, —CH$_2$—C$_{1-4}$ alkylene, —NH—C$_{1-4}$ alkylene, —(CO)—C$_{1-4}$ alkylene, —NH(CO)—C$_{1-4}$ alkylene, —(CO)NH—C$_{1-4}$ alkylene. The resulting bivalent structure can be further connected to other moieties of the molecule.

As used herein, the term "isoelectric point (pI)" is the pH (power of hydrogen) value of an aqueous solution of a molecule (such as a protein) at which the molecule has no net surface charge and is expressed as pH units. The pI of a protein can be experimentally measured using methods well-known in the art, such as, imaged capillary isoelectric focusing (iCIEF) and capillary isoelectric focusing (CIEF). Different biomolecules (proteins, nucleic acids, polysaccharides, etc.) with different pIs may be differently charged at a given pH, allowing them to be separated by methods such as ion exchange chromatography or isoelectric focusing.

As used herein, a molecule having an "alkaline pI" means that the pI of the molecule is below 7.0. As used herein, a molecule having an "acidic pI" means that the pI of the molecule is above 7.0.

As used herein, a "protein tag" refers to a polypeptide that can be introduced to a molecule of interest to facilitate the detection, isolation, immobilization or capture of the molecule of interest, or improve one or more properties (such as expression level, solubility and stability) of the molecule of interest.

Ion exchange chromatography (IEX) separates biomolecules based on differences in their net surface charge and differences in their affinity towards the ion exchanger (also referred to as the medium, resin or stationary phase). It is a commonly used technique for biomolecule purification. For example, in the anion exchange chromatography, a protein with a pI below the buffer pH will have negative net surface charge and bind to the positively charged anion exchanger; however, another protein with a pI above the buffer pH will have positive net surface charge and do not bind to the positively charged anion exchanger, and will thereby pass through the medium along with the buffer.

As used herein, the term "support" refers to a water-insoluble substance that can be isolated from a reaction mixture in solid or semi-solid form, such as a surface, a gel, a polymer, a matrix, a particle, a resin, a bead or a membrane.

The term "clarification" refers to removal of insoluble impurities from a system containing a biomolecule of interest. The process of "clarification" could be monitored by reduced turbidity, as measured for example, in nephelometric turbidity unit (NTU).

The term "polishing step" refers to a step to further remove minor contaminants and aggregates present in a mixture. Generally, in a process of ADC or antibody preparation, one or more polishing steps may be employed, wherein the polishing step may be selected from affinity chromatography, cation exchange chromatography, anion exchange chromatography, hydrophobic interaction chromatography, mixed mode chromatography and hydroxyapatite chromatography.

As used herein, the terms "impurities" and "contaminants" refer to undesirable substances in a mixture of a target molecule, such as cells, cell debris, host cell proteins and other proteins, endotoxins, media components, lipids, excess reaction materials (such as unreacted linker-payload intermediates), nucleic acids and viruses.

As used herein, the term "ppm (parts per million)" refers to the amount units of a contaminant (such as HCP or Protein A) per million units of the total mass of a target molecule (such as a target conjugate). The term is used to refer to a measure of purity of a target molecule.

The term "ultrafiltration" or "UF" refers to membrane filtration technique which employs controlled pore, semi-permeable membranes to concentrate or fractionate dissolved molecules. Molecules much larger than the pores are retained in the feed solution and are concentrated in direct proportion to the volume of liquid that passes through the membrane. The pore size of the ultrafiltration membrane is generally between 1-100 nm.

The term "diafiltration" or "DF" refers to a technique that uses ultrafiltration membranes to completely remove, replace or lower the concentration of salts or solvents from solutions containing proteins, peptides, nucleic acids, and other biomolecules. The process selectively utilizes permeable (porous) membrane filters to separate the components of solutions and suspensions based on their molecular size. Ultrafiltration and diafiltration can be used in combination and referred to as UF/DF.

Virus inactivation is included in purification process of many biotherapeutics to ensure safety. Several virus inactivation techniques are known in the art including, temperature, pH, radiation and exposure to certain chemical agents. Typically, virus inactivation could be performed by low-pH treatment. For Fc fragment-containing molecules, virus inactivation could be performed, for example, following a chromatography process step (e.g., Protein A affinity chromatography or cation exchange chromatography). In such cases, the pool containing the target molecule is adjusted to the pH desired for virus inactivation and held there for a certain length of time (viral inactivation acidification (VIA) step), the combination of pH and time having been shown to result in virus inactivation. The VIA pool is adjusted to a pH value close to neutral (viral inactivation neutralization (VIN) step) for further downstream processing.

Virus filtration (also known as virus-retentive filtration) is a common step of the purification process of many biotherapeutics. Virus filtration could be performed by UF or nano-filtration. Comparing with other dedicated virus clearance unit operations such as low pH or heat treatment, in most cases virus filtration is gentler, thus with less potential adverse impacts on product quality. Commercially available virus filtration products could be applied, according to the sizes of the viruses to be removed.

The term "process step" or "unit operation," as used interchangeably herein, refers to the use of one or more methods or devices to achieve a certain result in a purification process.

The term "continuous process," as used herein, refers to a process for purifying a target molecule, which includes two or more process steps (or unit operations), such that the output from one process step flows directly into the next process step in the process, without interruption and/or without the need to collect the entire volume of the output from a process step before performing the next process step. Continuous processes, as described herein, also include processes where the input of the fluid material in any single process step or the output is discontinuous or intermittent. Such processes may also be referred to as "semi-continuous" processes.

Ligase Fusion Proteins

In a general aspect, provided is a ligase fusion protein comprising a ligase and a Halo tag.

Ligase

The ligase of the present disclosure can be any ligase of interest. Particularly, it can specifically catalyze the conjugation between a first moiety comprising the recognition motif of the ligase donor substrate and a second moiety comprising the recognition motif of the ligase acceptor substrate to produce a target conjugate.

In some embodiments, the ligase is a transpeptidase. The transpeptidase can be naturally occurring or engineered. In some preferred embodiments, the ligase is a sortase, such as a sortase A (SrtA), sortase B (SrtB), sortase C (SrtC), sortase D (SrtD), sortase E (SrtE) or sortase F (SrtF), but not limited to. A "sortase" or "sortase enzyme" herein refers to an enzyme having sortase activity to catalyze a transpeptidation reaction, including for example, class A, class B, class C, class D, class E and class F sortases of the sortase enzyme superfamily (see, e.g., Dramsi, et al., Sorting sortases: a nomenclature proposal for the various sortases of Gram-positive bacteria, *Research in Microbiology*, (2005), 156: 289-297; Bradshaw, et al., Molecular features of the sortase enzyme family, *FEBS Journal*, (2015), 282: 2097-2114; Malik and Kim, A comprehensive in silico analysis of sortase superfamily, *J Microbiol.*, (2019), 57(6): 431-443; and EP3647419A1), but not limited thereto. Such an enzyme may be referred to as a SrtA, SrtB, SrtC, SrtD, SrtE or SrtF, but not limited thereto. A sortase can be naturally occurring or engineered. Naturally occurring sortase enzymes can be found in a variety of gram-positive bacteria, such as any strain, species or subspecies of the genera of *Streptococcus* (e.g., *Streptococcus pneumoniae* and *Streptococcus pyogenes*), *Staphylococcus* (e.g., *Staphylococcus* argenteus and *Staphylococcus aureus*), *Bacillus* (e.g., *Bacillus anthracis*) and *Listeria* (e.g., *Listeria monocytogenes*), but are not limited to. An engineered sortase, such as a sortase variant with substitutions, deletions or insertions of one or more amino acid residues, can be obtained from its natural counterpart via methods known in the art, such as protein engineering and chemical synthesis. Also contemplated are other variants (such as those with one or more active groups or labels) of any wild-type sortase known in the art. The provision is that the variant has identical or similar function of the wild-type sortase. Those skilled in the art will readily be able to identify a sortase and assign it to a specific class based on its sequence and other characteristics. However, the definition of sortase is not limited by any classification method or nomenclature system.

In some particular embodiments, the ligase is a sortase A (SrtA). A SrtA can be naturally occurring or engineered. Examples of SrtA include those described in, for example, U.S. Pat. No. 7,238,489 and Malik and Kim, 2019, supra, such as those from any strain, subspecies or species of the genera of *Streptococcus* (e.g., *Streptococcus pneumoniae* and *Streptococcus pyogenes*), *Staphylococcus* (e.g., *Staphylococcus* argenteus and *Staphylococcus aureus*), *Streptomyces* (e.g., *Streptomyces coelicolor*), *Bacillus* (e.g., *Bacillus anthracis*), *Lactobacillus* (e.g., *Lactobacillus plantarum*) and *Listeria* (e.g., *Listeria monocytogenes*), but are not limited to. The amino acid sequences of various SrtA can be found in, for example, U.S. Pat. No. 7,238,489 or public sequence databases (such as GenBank and Uniprot), the relevant content of which is incorporated herein by reference. Exemplary amino acid sequences of naturally occurring SrtA useful in the present disclosure can be proteins of Uniprot Accession Numbers: Q2FV99, A0A3S0JRJ4, A0A2T4Q430, A0A507SMZ3, A0A1F2JEX6, A0A364UNR7, A0A1J3ZU75, A0A0M2NSU2, A0A432A5VI, A0A1J4HB57, A0A4Q8MXV4, W1W5Z3, A0A2T4KDK7, A0A2K4DQX6, A0A2T4KHW3, A0A380FYB6, A0A2K4C0Y9, A0A4Q9WQB8, A0A121AFU6, A0A1Q8DH59, A0A5B2YTH7, A0A533IYI6, Q4L923, A0A1F1M8Z4, A0A2A1KC84 and A0A133Q671, but are not limited to. Engineered SrtA have been reported in various literatures, for example, WO 2016/014501, the relevant content of which is incorporated herein by reference. For example, an engineered SrtA having one or more substitutions (such as Pro94Arg, Asp160Asn, Asp165Ala, Lys190Glu, Lys196Thr, Glu105Lys and Glu108Gln) when compared to Q2FV99, or a truncated SrtA with an N-terminal 59 amino acids deletion compared to Q2FV99 as described in WO 2016/014501 may be considered. The amino acid sequence of a SrtA variant can have a sequence identity of at least about 85%, at least about 90%, at least about 95%, or at least about 99% with any other amino acid sequence described above. Also contemplated are variants (such as those with one or more active groups or labels) of any wild-type SrtA known in the art. The provision is that the variant has identical or similar function of the wild-type SrtA.

In some embodiments, the SrtA comprises an amino acid sequence selected from the group consisting of SEQ ID NOs: 1-26 (WT). In some other embodiments, the SrtA comprises an amino acid sequence selected from the group consisting of SEQ ID NOs: 1-26 and comprises amino acid substitutions at positions 34, 100, 105 and 136. In some embodiments, the amino acid residues at positions 34, 100, 105 and 136 are substituted with Ser, Asn, Ala and Thr (i.e., [Ser34][Asn100][Ala105][Thr136], SNAT), Tyr, Asn, Ala and Thr (i.e., [Tyr34][Asn100][Ala105][Thr136], YNAT), Trp, Asn, Asp and Thr (i.e., [Trp34][Asn100][Asp105][Thr136], WNDT), or Val, Asn, Asn and Ser (i.e., [Val34][Asn100][Asn105][Ser136], VNNS), respectively. In a particular embodiment, the sortase A comprises the amino acid sequence of SEQ ID NO: 27, which is the SNAT counterpart of SEQ ID NO: 1.

In some embodiments, the sortase A comprises an amino acid sequence having a sequence identity of at least about 85%, at least about 90%, at least about 95%, or at least about 99% with an amino acid sequence selected from the group consisting of SEQ ID NOs: 1-26.

In some embodiments, the sortase A comprises an amino acid sequence having a sequence identity of at least about 85%, at least about 90%, at least about 95%, or at least about 99% with an amino acid sequence selected from the group consisting of SEQ ID NOs: 1-26 and comprises amino acid substitutions of SNAT, YNAT, WNDT or VNNS at positions 34, 100, 105 and 136.

In another aspect, provided is a SrtA comprising an amino acid sequence selected from the group consisting of SEQ ID NOs: 1-26 and comprising amino acid substitutions of SNAT, YNAT, WNDT or VNNS at positions 34, 100, 105 and 136 or an amino acid sequence having a sequence identity of at least about 85%, at least about 90%, at least about 95%, or at least about 99% thereto. In another particular aspect, provided is a SrtA comprising the amino acid sequence of SEQ ID NO: 27 or an amino acid sequence having a sequence identity of at least about 85%, at least about 90%, at least about 95%, or at least about 99% thereto.

Halo Tag

A Halo tag is a mutant haloalkane dehalogenase or a variant thereof that removes the halogen from a haloalkyl substrate (e.g., an agent comprising a haloalkyl moiety —(CH$_2$)$_{2-30}$—X, wherein X is a halogen like F, Cl, Br, I, particularly Cl or Br) and forms covalent linkage with the remaining moiety of the substrate. Mutant haloalkane dehalogenases have been described in, for example, WO 2006/093529 and WO 2008/054821, the relevant content of which is incorporated herein by reference. Mutant haloalkane dehalogenases useful in the present disclosure may include, but are not limited to, mutants of *Xanthobacter* dehalogenases (such as *Xanthobacter autotrophicus* dehalogenase (DhlA)) or *Rhodococcus* dehalogenases (such as *Rhodococcus rhodochrous* dehalogenase (DhaA)), such as those comprising one or more substitutions at the catalytic triad residues, such as substitution of His272 with Phe/Ala/Gly/Gln/Asn or Asp106 with Cys or other substitutions as described in WO 2008/054821. The provision is that the mutant haloalkane dehalogenase is able to form covalent linkage with a haloalkyl substrate.

In some preferred embodiments, the Halo tag comprises the amino acid sequence of SEQ ID NO: 28. In some embodiments, the Halo tag comprises an amino acid sequence having at least about 85%, at least about 90%, at least about 95%, or at least about 99% sequence identity with SEQ ID NO: 28.

Embodiments Further Comprising Additional Elements and/or Modifications

Optionally, the ligase fusion protein may further comprise one or more additional elements, such as an additional polypeptide or a label. Preferably, the ligase fusion protein substantially preserves the desired properties. Those of skills in the art can select a suitable element based on the desired function or property of the fusion protein. Methods for introducing such elements are known in the art.

The additional polypeptide can be a protein tag with a desired property. Examples of protein tags may include, but be not limited to, reporter proteins, binding tags and solubility-enhancement tags. Examples of reporter proteins include, but are not limited to, fluorescent proteins (e.g., green fluorescent protein and its variants), AP (Alkaline Phosphatase) and HRP (Horseradish Peroxidase). A binding tag can effectively bind to a corresponding binding partner in a covalent or non-covalent manner Examples of binding tags include, but are not limited to, polyhistidine tag (i.e., His tag, e.g., His6 or Hiss tag), Fc tag (the constant region (domain 3 and 4) of immunoglobulin heavy-chain), calmodulin tag, maltose-binding protein (MBP), glutathione-S-transferase (GST), S tag (which interacts with ribonuclease S-protein), peptides that bind avidin/streptavidin/neutravidin (e.g., SBP tag, Strep tag and Strep tag II), Halo tag, SNAP tag and CLIP tag (engineered mutants of the DNA repair protein O$^6$-alkylguanine-DNA alkyltransferase) and variants thereof. A solubility-enhancement tag, when expressed as a part of a recombinant protein, can typically enhance the expression level and solubility of the recombinant protein. Examples of solubility-enhancement tags include, but are not limited to, GB1 tag (the B1 domain of Streptococcal protein G), the Z domain of Staphylococcal protein A, SUMO (Small ubiquitin-related modifier), thioredoxin, GST and MBP. It is appreciated that the property of a protein tag does not constitute any limitation on the embodiments, and a protein tag can have one or more properties, for example, a reporter protein or a binding tag can be a solubility-enhancement tag as well.

The additional polypeptide can also be a short peptide that can serve as a linker, a spacer or an enzyme-cleavable sequence (such as a TEV protease recognition motif or a thrombin recognition motif). In some embodiments, a linker peptide (such as a polyglycine stretch, (G$_4$S)$_n$, wherein G is glycine, S is serine, and n is an integer of 1-6, preferably n is an integer of 2-5) which is rigid or flexible may be inserted between the ligase and the Halo tag to ensure the proper function of the fusion protein using methods known in the art. In some embodiments, the linker peptide is (G$_4$S)$_2$. In some embodiments, the ligase fusion protein comprises the amino acid sequence of SEQ ID NO: 29.

The label can be a tracer molecule, such as a fluorophore, a radionuclide, a fluorescent molecule, a fluorescent quantum dot or a nanogold particle. The label can also be an affinity label, such as Biotin. Such labels may be used to monitor reactions catalyzed by the fusion protein or to track or immobilize the fusion protein.

The ligase fusion protein may comprise one or more modifications, wherein the ligase, the Halo tag and the additional polypeptide (when applicable) are independently modified through, for example, substitution, deletion, addition, insertion of one or more amino acids, or introduction of moieties or active groups at one or more suitable residues, as long as the desired biological activities or functions of the modified fusion protein are substantially similar with that of the corresponding fusion protein.

Specific Embodiments for Ligases Having an Alkaline pI

In a preferable aspect, provided is a ligase fusion protein having an altered pI comparing to the ligase from which it is derived, wherein the ligase has an alkaline pI and the Halo tag has an acidic pI. By fusing to a ligase with an alkaline pI to a Halo tag with an acidic pI, a ligase fusion protein with an altered pI is obtained, thereby leading to certain beneficial effects under certain circumstances. For example, the ligase fusion protein may have altered charge characteristics comparing to the ligase under certain conditions (for example, in a specific buffer system at a given pH or in an in vivo environment), thereby leading to, for example, altered solubility, stability or electrostatic interaction patterns (i.e., the ability to form electrostatic interaction with a charged substance) comparing to the ligase.

In some embodiments, the ligase has an isoelectric point (pI) of about 7.5 to about 10.0, the Halo tag has a pI of about 4.5 to about 5.0, and the pI of the ligase fusion protein is about 2.0 to about 4.5 pH units lower than that of the ligase. In those embodiments comprising one or more additional elements (such as additional polypeptides or labels as defined above or a combination thereof) and/or modifications (such as amino acid substitutions, deletions, additions, insertions, or moieties or active groups), it is preferable that the desired pI difference between the ligase fusion protein and the ligase is achieved. In some embodiments, the additional polypeptide (if applicable) may have a specific pI that helps to achieve the desired pI of the ligase fusion protein.

In some embodiments, the pI of the ligase fusion protein is about 2.0 to about 2.5 pH units lower than that of the ligase, such as about 2.0, 2.1, 2.2, 2.3, 2.4 or 2.5 pH units lower than that of the ligase. In some embodiments, the pI of the ligase fusion protein is about 2.6 to about 3.0 pH units lower than that of the ligase, such as about 2.6, 2.7, 2.8, 2.9 or 3.0 pH units lower than that of the ligase. In some embodiments, the pI of the ligase fusion protein is about 3.1 to about 3.5 pH units lower than that of the ligase, such as about 3.1, 3.2, 3.3, 3.4 or 3.5 pH units lower than that of the ligase. In some embodiments, the pI of the ligase fusion protein is about 3.6 to about 4.0 pH units lower than that of the ligase, such as about 3.6, 3.7, 3.8, 3.9 or 4.0 pH units lower than that of the ligase. In some embodiments, the pI of the ligase fusion protein is about 4.1 to about 4.5 pH units lower than that of the ligase, such as about 4.1, 4.2, 4.3, 4.4, 4.5 pH units lower than that of the ligase.

In some embodiments, the pI of the ligase fusion protein is about 4.5 to about 6.5, such as about 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4 or 6.5. In some preferred embodiments, the pI of the ligase fusion protein is about 5.0 to about 6.0.

In some embodiments, the pI of the ligase is about 7.5 to about 8.5, such as 7.5, 7.6, 7.7, 7.8, 7.9, 8.0, 8.1, 8.2, 8.3, 8.4 or 8.5. In some embodiments, the pI of the ligase is about 8.6 to about 9.5, such as 8.6, 8.7, 8.8, 8.9, 9.0, 9.1, 9.2, 9.3, 9.4 or 9.5. In some embodiments, the pI of the ligase is about 9.6 to about 10.0, such as about 9.6, 9.7, 9.8, 9.9 or 10.0.

In some particular embodiments, the pI of the fusion protein is about 5.0 to about 6.0, and the pI of the ligase is about 7.6 to about 9.7.

In some embodiments, the ligase is a sortase. The sortase can be selected from SrtA, SrtB, SrtC, SrtD, SrtE and SrtF.

In some preferred embodiments, the SrtA comprises an amino acid sequence selected from the group consisting of SEQ ID NOs: 1-12 (WT). In some other embodiments, the SrtA comprises an amino acid sequence selected from the group consisting of SEQ ID NOs: 1-12 and comprises amino acid substitutions at positions 34, 100, 105 and 136. In some embodiments, the amino acid residues at positions 34, 100, 105 and 136 are substituted with Ser, Asn, Ala and Thr (SNAT), Tyr, Asn, Ala and Thr (YNAT), Trp, Asn, Asp and Thr (WNDT), or Val, Asn, Asn and Ser (VNNS), respectively. The pIs of these SrtA are listed in Table 1.

TABLE 1

| | WT | SNAT | YNAT | WNDT | VNNS |
|---|---|---|---|---|---|
| SEQ ID NO: 1 | 7.673 | 8.508 | 8.473 | 7.675 | 8.508 |
| SEQ ID NO: 2 | 8.867 | 9.114 | 9.066 | 8.874 | 9.114 |
| SEQ ID NO: 3 | 9.445 | 9.458 | 9.403 | 9.306 | 9.458 |
| SEQ ID NO: 4 | 8.874 | 9.123 | 9.075 | 8.881 | 9.123 |
| SEQ ID NO: 5 | 8.867 | 9.114 | 9.066 | 8.874 | 9.114 |
| SEQ ID NO: 6 | 9.114 | 9.306 | 9.255 | 9.123 | 9.306 |
| SEQ ID NO: 7 | 8.868 | 9.114 | 9.066 | 8.874 | 9.114 |
| SEQ ID NO: 8 | 8.867 | 9.114 | 9.066 | 8.874 | 9.114 |
| SEQ ID NO: 9 | 9.132 | 9.471 | 9.414 | 9.319 | 9.471 |
| SEQ ID NO: 10 | 8.896 | 9.33 | 9.275 | 9.141 | 9.33 |
| SEQ ID NO: 11 | 9.414 | 9.659 | 9.605 | 9.544 | 9.659 |
| SEQ ID NO: 12 | 8.896 | 9.33 | 9.275 | 9.141 | 9.33 |

In some embodiments, the sortase A comprises an amino acid sequence having a sequence identity of at least about 85%, at least about 90%, at least about 95%, or at least about 99% with an amino acid sequence selected from the group consisting of SEQ ID NOs: 1-12.

In some embodiments, the sortase A comprises an amino acid sequence having a sequence identity of at least about 85%, at least about 90%, at least about 95%, or at least about 99% with an amino acid sequence selected from the group consisting of SEQ ID NOs: 1-12 and comprises amino acid substitutions of SNAT, YNAT, WNDT or VNNS at positions 34, 100, 105 and 136.

In a particular embodiment, the sortase A comprises the amino acid sequence of SEQ ID NO: 27. It is the SNAT counterpart of SEQ ID NO: 1 and has a pI of 8.508.

In some embodiments, a linker peptide (such as a polyglycine stretch, $(G_4S)_n$, wherein G is glycine, S is serine, and n is an integer of 1-6, preferably n is an integer of 2-5) which is rigid or flexible may be inserted between the ligase and the Halo tag to ensure the proper function of the fusion protein using methods known in the art. In some embodiments, the linker peptide is $(G_4S)_2$. In some embodiments, the ligase fusion protein comprises the amino acid sequence of SEQ ID NO: 29.

Methods for Obtaining the Ligase Fusion Protein

The ligase, the Halo tag and the additional polypeptide (when applicable) can be fused in any manner. In some embodiments, the ligase is N-terminal to the Halo tag. In some embodiments, the Halo tag is N-terminal to the ligase. In some embodiments, a linker peptide (such as a polyglycine stretch, $(G_4S)_n$, wherein G is glycine, S is serine, and n is an integer of 1-6, preferably n is an integer of 2-5) which is rigid or flexible may be inserted between the ligase and the Halo tag to ensure the proper function of the fusion protein using methods known in the art. In some embodiments, the linker peptide is $(G_4S)_2$. In some embodiments, the ligase fusion protein comprises the amino acid sequence of SEQ ID NO: 29.

The ligase fusion protein can be obtained using various techniques known in the art, such as expressed from a nucleic acid obtained by recombinant DNA techniques, chemical synthesis, enzyme-catalyzed coupling or chemical coupling methods. In some preferred embodiments, the ligase fusion protein is a recombinant protein encoded by a nucleic acid comprising nucleic acid sequences encoding the ligase and the Halo tag. The recombinant protein can be expressed in and purified from a suitable host cell, such as a mammalian cell, a bacterium, a yeast cell or an insect cell, preferably a bacterium, such as E. coli.

Nucleic Acids and Vectors

Also provided is a nucleic acid encoding the ligase fusion protein according to the present disclosure, comprising a first polynucleotide encoding the ligase and a second polynucleotide encoding the Halo tag according to the present disclosure, wherein the first and second polynucleotides are operably linked to a promoter. In some embodiments, the nucleic acid according to the present disclosure further comprises a third polynucleotide encoding an additional polypeptide operably linked to the ligase and the Halo tag. Examples of the third polypeptide are as described above.

In some embodiments, the first polynucleotide encodes a sortase A, and the second polynucleotide encodes a Halo tag. In some embodiments, the first polynucleotide encodes a sortase A having an amino acid sequence selected from the group consisting of SEQ ID NOs: 1-26, and the second polynucleotide encodes a Halo tag having the amino acid sequence of SEQ ID NO: 28. In a particular embodiment, the first polynucleotide encodes a SrtA having the amino acid sequence of SEQ ID NO: 27 and the second polynucleotide encodes a Halo tag having the amino acid sequence of SEQ ID NO: 28. In another particular embodiment, the nucleic acid encodes a ligase fusion protein having the amino acid sequence of SEQ ID NO: 29. It is appreciated by those of skill in the art that one or more nucleotides in the nucleic acid can be optimized without departing from the spirit of the present disclosure.

In some embodiments, the nucleic acid according to the present disclosure is prepared as recombinant nucleic acids, which may further comprise one or more additional polynucleotides, such as regulatory elements and polynucleotides encoding protein tags. Such regulatory elements may regulate the expression of the fusion protein according to the present disclosure, including, but not limited to, enhancers, insulators, internal ribosome entry sites (IRES). The recombinant nucleic acids comprising the nucleic acid according to the present disclosure can be prepared using molecular cloning techniques well known in the art, for example, chemical synthesis, site-directed mutagenesis and polymerase chain reaction (PCR) techniques (see Sambrook, J., E. F. Fritsch, and T. Maniatis (1989), *Molecular cloning: a laboratory manual*, 2nd ed., Cold Spring Harbor Laboratory, Cold Spring Harbor, N.Y.).

In some embodiments, the nucleic acid according to the present disclosure is cloned into a vector, preferably, an expression vector expressible in a host cell (e.g., a bacterial, mammalian, yeast or insect cell). Those skilled in the art are able to select suitable expression vector based on the nature of the ligase fusion protein and the host cell to be used. In some embodiments, the vector is a bacterial expression vector expressible in bacteria, such as *E. coli*. In some embodiments, the expression vector can further contain one or more selective marker genes, for example, a neomycin or puromycin resistance gene. After expression, the fusion protein can be purified using methods known in the art according to the protein tag used. Depending on the type of host cells and purification strategies to be used, those of skills in the art are able to select suitable expression vectors, promoters, regulatory elements and protein tags.

Immobilized Ligase

In another general aspect, provided is an immobilized ligase, comprising the ligase fusion protein according to the present disclosure immobilized to a support.

The support may be in solid form or semi-solid form made of any material. Non-limiting examples of the support may include, but are not limited to, a resin (e.g., an agarose resin, silicone resin, polymethyl methacrylate resin, epoxy resin or cellulose resin), gel (such as an alginate hydrogel), a bead/microsphere/particle (e.g., a polystyrene bead, a magnetic particle), a plate, a well, a tube, a film, a membrane, a matrix and glass (e.g., a glass slide).

In some preferred embodiments, the support is a resin. In some more preferred embodiments, the support is selected from the group consisting of agarose resin, silicone resin, polymethyl methacrylate resin and cellulose resin. In a particular embodiment, the support is a highly crosslinked agarose resin.

Methods of enzyme immobilization are known in the art, such as adsorption, covalent or non-covalent binding, entrapment, encapsulation, and cross linking. It is desirable that a maximum enzymatic activity of the ligase is preserved after immobilization and a minimum amount of free ligase is present in the conjugate product after the conjugation reaction. Preferably, the support is modified on the surface to comprise one or more functional groups such that the ligase fusion protein can be covalently immobilized on the support.

Preferably, the support comprises one or more chemically active functional groups that can form covalent bond with reactive groups (such as amines, thiols and carboxylates) of the ligase fusion protein or with reactive groups in a haloalkyl substrate, or the support comprises one or more binding partners of a corresponding binding tag/affinity label that is comprised in the ligase fusion protein. Correspondence relationship between chemically active functional groups and the reactive groups or correspondence relationship between binding tags/affinity labels and binding partners are well-known in the art.

In some embodiments, the support comprises chemically active functional groups that can form covalent bond with reactive groups (such as amines, thiols and carboxylates) on the ligase fusion protein or with reactive groups in a haloalkyl substrate. In some particular embodiments, the support comprises functional groups selected from the group consisting of cyanate ester, isothiocyanates, isocyanates, carbodiimides, N-Hydroxysuccinimide (NHS) esters, amines, carbonates, epoxides, maleimides, haloacetyls, aziridines, ethyl chloroformate and aliphatic aldehydes.

In some embodiments, the support is an epoxy-activated resin, a CNBr (cyanogen bromide)-activated resin or an NHS-activated resin, preferably an epoxy-activated resin. In some particular embodiments, the support is an epoxy-activated agarose resin, preferably an epoxy-activated highly crosslinked agarose resin. In some preferred embodiments, before reacting with the haloalkyl substrate, the epoxy-activated resin is pre-processed to introduce amino group. In some preferred embodiments, the pre-processing of the epoxy-activated resin is performed using ammonia. In some preferred embodiments, the pre-processing of the epoxy-activated resin results in introduction of amino group on the oxirane ring and ring-opening of the oxirane ring gives a hydroxy group. Such hydroxy group are optionally end-capped in subsequent procedures of the preparation of the support. In a particular embodiment, the pre-processing of the epoxy-activated resin results in introduction of amino group on the oxirane ring and ring-opening of the oxirane ring gives a hydroxy group which is optionally esterified using esterification agent (e.g., acetylation agent like $Ac_2O$) in subsequent procedures of the preparation of the support. Such preprocessed epoxy-activated resin is within the scope of "epoxy-activated resin" as defined above. In some preferred embodiments, the resin is an agarose resin (such as a highly crosslinked agarose resin) or a polymethyl methacrylate resin.

In some other embodiments, the support comprises one or more binding partners of a corresponding binding tag/affinity label that is comprised in the ligase fusion protein, such as an additional tag or affinity label. Correspondence relationship between reactive groups or between binding tags/affinity labels and binding partners are well-known in the art. Examples of binding tags/affinity labels and the corresponding binding partners may include, but are not limited to, His tag and $Ni^{2+}$, biotin/SPB tag/Strep tag/Strep tag II and streptavidin/avidin/neutravidin, GST tag and Glutathione, Fc tag and Protein A, calmodulin tag and $Ca^{2+}$, MBP and amylose, S tag and ribonuclease S-protein, SNAP tag and benzylguanine (BG) derivatives, and CLIP tag and benzylcytosine (BC) derivatives.

In some preferred embodiments, the support is functionalized to form covalent interaction with the Halo tag by comprising haloalkyl linkers. The haloalkyl linkers can be introduced to the support by covalently connecting one or more functional groups comprised by the support to one or more reactive groups in haloalkyl substrates, and the support obtained thereby is also known as a haloalkyl linker-modified support. The haloalkyl linker-modified support is within the scope of "support" as defined above. Examples of haloalkyl substrates include but are not limited to those described in e.g., US20060024808A1 and WO2006093529. Haloalkyl substrates and methods for preparing such supports are described in, for example, U.S. Pat. Nos. 7,429,472, 7,888,086 and 8,202,700, Japanese Pat. No. 4748685, the relevant content of which is incorporated herein by reference.

The haloalkyl substrate may comprise a haloalkyl moiety comprising a primary or secondary halo group, preferably a primary halo group. The halo group in the haloalkyl moiety is selected from F, Cl, Br and I, preferably selected from Cl and Br. In some embodiments, the haloalkyl substrate has a structure of the following formula (I):

$$(F1_a—H1_b)_r—Lh-(F2_b—H2_a)_s \quad (I)$$

wherein,
F1 and F2 are independently a moiety comprising a reactive group which can form covalent bond with chemically active functional groups comprised by the support;
H1 and H2 are independently selected from halo $C_{2-30}$ alkyl;
Lh is a chemical bond or is a $C_{3-200}$ alkylene, and wherein one or more (—$CH_2$—) structures in the alkylene is optionally replaced by —O—, —NH—, —(CO)—, —NH(CO)— and —(CO)NH—;
Lh is optionally substituted with 1, 2 or 3 substituents selected from —O—$C_{1-10}$ alkyl, —NH—$C_{1-10}$ alkyl, —(CO)—$C_{1-10}$ alkyl, —NH(CO)—$C_{1-10}$ alkyl and —(CO)NH—$C_{1-10}$ alkyl;
a is 0 or 1, b is 0 or 1, provided that a and b are different;
r is an integer of 1 to 100;
s is an integer of 1 to 100.

In some embodiments, r is an integer of 1 to 10, for example, 1, 2, 3, 4, 5, 6, 7, 8, 9 or 10. In some embodiments, s is an integer of 1 to 10, for example, 1, 2, 3, 4, 5, 6, 7, 8, 9 or 10. In some embodiments, reactive group in F1 or F2 is selected from amino, amines, thiol group, thiols and active esters. In some embodiments, the active ester contains one or more carboxylic acid radicals (such as in carbonic acid monoester of suitable alcohol or phenol, e.g. electron-deficient phenol like 4-nitrophenol; or such as in NHS esters or sulfo-NHS esters) or one or more sulfonic acid radicals (such as in methane sulfonic acid active ester, e.g., MsO—).

In a particular embodiment, F1 or F2 is

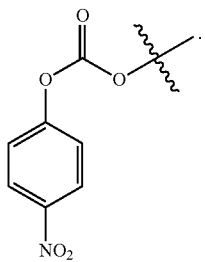 [SMILES: *OC(=O)Oc1ccc([N+](=O)[O-])cc1]

In some embodiments, H1 and H2 are independently selected from halo $C_{2-20}$ alkyl, preferably halo $C_{2-10}$ alkyl, especially halo $C_6$ alkyl. In some particular embodiments, the alkyl in H1 or H2 is a linear alkyl. In a particular embodiment, H1 or H2 is $(CH_2)_{2-30}$—X, preferably $(CH_2)_{2-20}$—X, more preferably $(CH_2)_{2-10}$—X, especially $(CH_2)_6$—X, wherein X is a halogen selected from F, Cl, Br and I.

In some preferred embodiments, the support is Halo-Link™ resin (Promega).

In some more preferred embodiments, the support is a resin that may comprise a haloalkyl linker comprising the structure of —$(CH_2)_{2-30}$—X, wherein X is a halogen selected from F, Cl, Br and I. In a particular embodiment, the support is a haloalyl linker-modified resin, preferably an agarose resin or a polymethyl methacrylate resin, more preferably a highly crosslinked agarose resin.

In some particular embodiments, a is 1, b is 0, r is 1, s is 1, F1 is

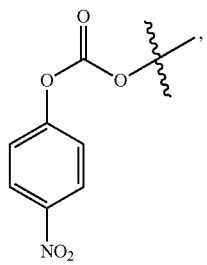 [SMILES: *OC(=O)Oc1ccc([N+](=O)[O-])cc1]

Lh is

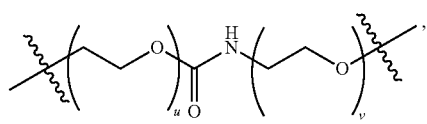

H2 is $(CH_2)_{2-20}$—Cl, and the haloalkyl substrate is a chloroalkyl substrate having the structure of formula (I-1):

(I-1)

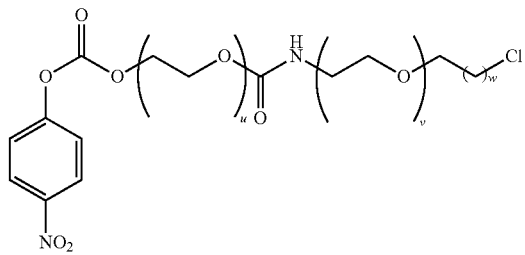

wherein, u is an integer of 1 to 20, v is an integer of 0 to 20, and w is an integer of 1 to 19.

In a particular embodiment, u is 3, v is 2, and w is 5, and the chloroalkyl substrate has the following structure of formula (I-1-1):

(I-1-1)

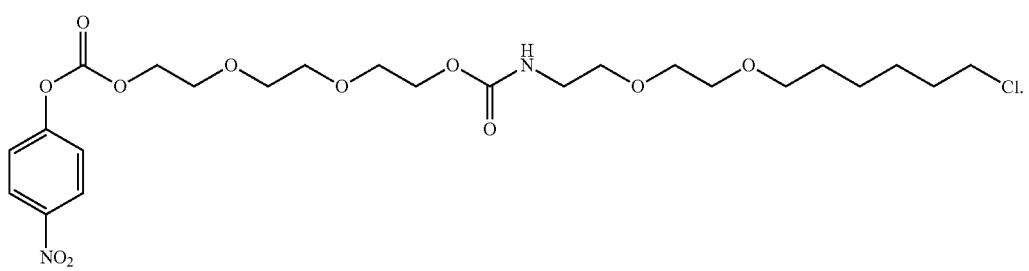

In a particular embodiment, the support is a chloroalkyl linker-modified support and has the structure of formula (II):

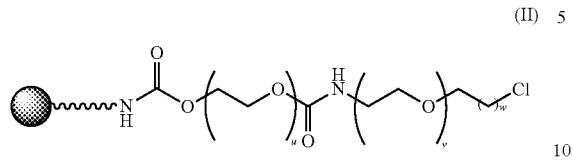
(II)

wherein u is an integer of 1 to 20, v is an integer of 0 to 20, and w is an integer of 1 to 19;

depicts the support and is a resin, a bead, a membrane, a gel, a matrix, a film, a plate, a well, a tube, a glass slide or a surface, preferably a resin, more preferably an agarose resin, a silicone resin, a polymethyl methacrylate resin or cellulose resin, and most preferably a highly crosslinked agarose resin. Note that for the sake of clarity, only a single chloroalkyl-linker moiety is depicted attached to the support, but it is understood that there would be many such chloroalkyl-linker moieties attached to the support.

In an embodiment, the chloroalkyl linker-modified support as shown in formula (II) is prepared using a resin, a bead, a membrane, a gel, a matrix, a film, a plate, a well, a tube, a glass slide or a surface as denoted by

, with the chloroalkyl substrate of formula (I-1).

In a particular embodiment, the chloroalkyl linker-modified support as shown in formula (II) is prepared from a preprocessed epoxy-activated resin, which is prepared by introduction of amino group on the oxirane ring of the epoxy-activated resin, and ring-opening of the oxirane ring during the preprocessing gives a hydroxy group which is optionally esterified using $Ac_2O$ in subsequent procedures of the preparation of the support, and the support as shown in formula (II) has the structure of formula (II-1):

wherein, the substructure

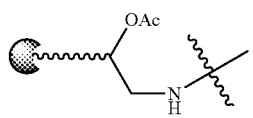 [SMILES: *NCC(C)OC(C)=O]

represents the preprocessed epoxy-activated resin, wherein the moiety

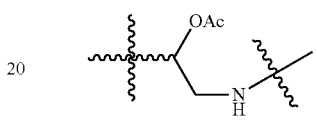

represents an oxirane ring which is reacted with amino group and ring-opened to give a hydroxy group esterified subsequently to form AcO—, and the moiety

represents the other part of the preprocessed epoxy-activated resin.

In some embodiments, the immobilized ligase has the following structure:

Support-Linker-HaloTag Ligase wherein

Support is a solid support, e.g. selected from resin, a bead, a membrane, a gel, a matrix, a film, a plate, a well, a tube, a glass slide or a surface, preferably a resin, more preferable an agarose resin, a silicone resin, a polymethyl methacrylate resin or cellulose resin, most preferably a highly crosslinked agarose resin;

Linker is a linker moiety, covalently bound to the Support, e.g., comprising a chain of 10 to 60 carbon atoms, optionally comprising one or more ether, ester, carbamate, and/or amide bonds; e.g., a linker moiety of Formula (II-1') or (II')

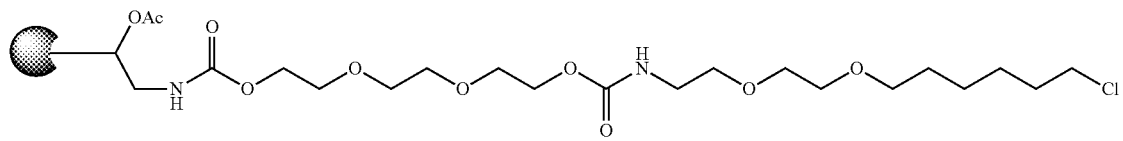
(II-1)

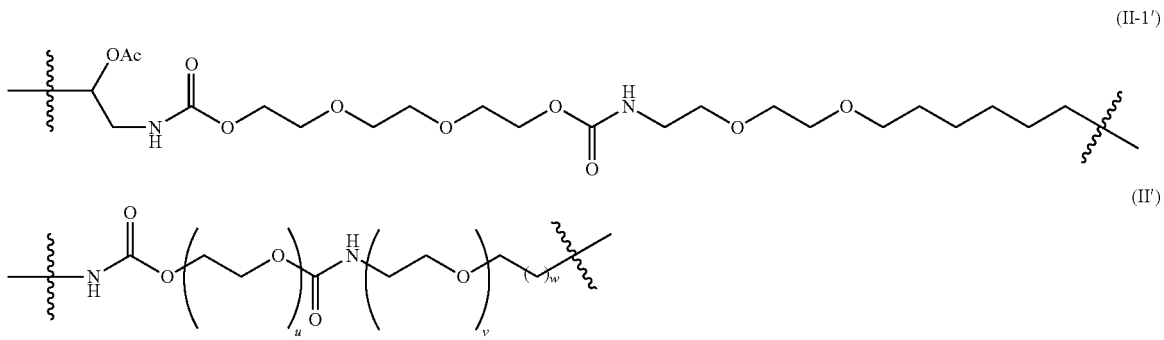

wherein u is an integer of 1-20, v is an integer of 0-20, and w is an integer of 1 to 19;

HaloTag is a Halo tag (haloalkane dehalogenase polypeptide), covalently bound to the linker;

Ligase is a ligase polypeptide;

wherein one or more "-Linker-HaloTag-Ligase" moieties are bound to the same Support.

In some embodiments, an immobilized ligase comprising the linker moiety of Formula (II-1') is obtained from the following reactions: 1) reaction of one or more chloroalkyl substrates with the support, forming a chloroalkyl linker-modified support; and 2) the subsequent reaction of the chloroalkyl linker-modified support with HaloTag (for example, the Halo tag comprised in the ligase fusion protein), obtaining the immobilized ligase.

Use of the Ligase Fusion Protein and the Immobilized Ligase

Also provided is use of the ligase fusion protein or the immobilized ligase according to the present disclosure in the preparation of a conjugate. The type of the conjugate is not limited. The conjugate can be obtained by contacting the ligase fusion protein or the immobilized ligase with a first moiety and a second moiety, wherein one of the first moiety and second moiety comprises the recognition motif of the ligase donor substrate, and the other comprises the recognition motif of the ligase acceptor substrate.

In some embodiments, the conjugate is a bioconjugate. Examples of bioconjugates may include, but are not limited to, siRNA conjugates, peptide-hormone conjugates, peptide-peptide conjugates, peptide-drug conjugates, antibody-drug conjugates and multispecific antibodies. In some embodiments, the conjugate comprises a receptor, an antibody or an antibody fragment. In some embodiments, the conjugate is an antibody-drug conjugate.

In some embodiments, the pI of the conjugate is about 1.0 to about 4.0 pH units higher than that of the ligase fusion protein, such as about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 or 4.0 pH units higher than that of the ligase fusion protein. In some preferred embodiments, the pI of the conjugate is about 2.0 to about 4.0 pH units higher than that of the ligase fusion protein.

In some embodiments, the pI of the conjugate is about 5.5 to about 10.5, such as about 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.0. In some preferred embodiments, the pI of the conjugate is about 7.5 to about 10.0. In some particular embodiments, the pI of the conjugate is about 8.0 to about 9.0.

In some embodiments, the pI of the conjugate is about 5.5 to about 10.5, and the pI of the ligase fusion protein is about 4.5 to about 6.5. In some particular embodiments, the pI of the conjugate is about 8.0 to about 9.0, and the pI of the ligase fusion protein is about 5.0 to about 6.0.

In some embodiments, the ligase fusion protein and the conjugate are separable from each other using ion exchange chromatography (IEX). The IEX can be anion exchange chromatography (AEX), cation exchange chromatography (CEX) or a combination thereof. In some other embodiments, the ligase fusion protein and the conjugate are separable from each other using isoelectric focusing, such as iCIEF or CIEF.

In some particular embodiments, the ligase is a sortase, preferably a sortase A, and the conjugate is an antibody-drug conjugate.

The Process According to the Present Disclosure

In another aspect, provided is a process for the preparation of a conjugate comprising a first moiety and a second moiety, comprising the steps of:

(a) providing System 1 comprising the first moiety and providing System 2 comprising the second moiety; and (b) contacting a ligase unit with System 1 and System 2 in step (a) to catalyze the conjugation reaction between the first moiety and second moiety to obtain the conjugate, wherein the ligase unit comprises a ligase, the first moiety and the second moiety each independently comprises a biomolecule, a protein, an antibody, an antibody fragment, a receptor, a signal transduction factor, a cell growth factor, a nucleic acid or a nucleic acid analogue, a small molecule compound, a glycan, a PEG moiety, a radionuclide, a cytokine, an immunomodulator, a tracer molecule, a fluorophore, a fluorescent molecule, a peptide, a polypeptide, or a peptidomimetic; and one of the first moiety and the second moiety further comprises the recognition motif of the ligase donor substrate, and the other one of the first moiety and the second moiety comprises the recognition motif of the ligase acceptor substrate.

In one embodiment, the first moiety and the second moiety are connected with each other through the coupling of the recognition motif of the ligase donor substrate and the recognition motif of the ligase acceptor substrate.

In one embodiment, at least one of the first moiety and the second moiety comprises a linker, and preferably the ligase recognition motif (i.e., the recognition motif of the ligase donor substrate, or the recognition motif of the ligase acceptor substrate) comprised by the said first moiety or the second moiety is a part of the linker. In one embodiment, the said first moiety or the second moiety comprises a payload and a linker, and the linker may comprise the ligase recognition motif and one or more structural moieties which are connected to the payload. In other embodiment, the said first moiety or the second moiety comprises a biomolecule and a linker, and the linker may comprise the ligase recognition motif and one or more structural moieties which are connected to the biomolecule. In yet another embodiment, the biomolecule and/or the payload are independently modified to comprise one or more additional moieties, such as active groups, spacers and labels.

The terms "first moiety" and "second moiety" of the conjugate are used herein to refer to various moieties of the conjugate. For example, for a bioconjugate, the first moiety can be the biomolecule moiety of the conjugate, and the second moiety can be another functional moiety or the rest part of the conjugate. It should be understood that the phase "first" and "second" are only used to designate different moieties for the purpose of clarity but do not constitute any limitation.

The terms "System 1" and "System 2" are only used to designate different portions containing the moiety to be conjugated but do not constitute any limitation. System 1 and System 2 can each independently be in any form, such as aqueous form, solid form or semi-solid form. Preferably, at least one of System 1 and System 2 is aqueous form, such as (aqueous) solution or a fluid. System 1 and System 2 can each independently be selected from a culture (such as a tissue culture, a mammalian cell culture, a yeast cell culture, a bacterial cell culture and a bacteriophage culture), a harvested cell culture fluid, a solution containing an antibody, a solution containing a linker-payload intermediate, etc. "System 1" and "System 2" can be identical or different, preferably they are different.

Ligase Unit

The ligase unit may comprise any ligase without limitation. Particularly, it can recognize the recognition motifs on the two moieties and catalyze the conjugation between the two moieties. In some embodiments, the ligase is a transpeptidase. In some embodiments, the ligase is a sortase. The sortase can be selected from the group consisting of SrtA, SrtB, SrtC, SrtD, SrtE, SrtF and a combination thereof. In some embodiments, the ligase is a SrtA as described above. In some embodiments, the ligase is further modified by comprising one or more additional elements, such as a protein tag or a label as described above, or by comprising one or more amino acid substitutions, deletions or insertions.

The ligase can be a free ligase or immobilized to a support. Preferably, the ligase is immobilized to a support, such that higher operational stability and reusability, lower enzyme contamination, less area occupancy, and continuous production can be achieved. The support may be in solid form or semi-solid form made of any material. Non-limiting examples of the support may include, but are not limited to, a resin (e.g., an agarose resin, silicone resin, polymethyl methacrylate resin, epoxy resin or cellulose resin), gel (such as an alginate hydrogel), a bead/microsphere/particle (e.g., a polystyrene bead, a magnetic particle), a plate, a well, a tube, a film, a membrane, a matrix and glass (e.g., a glass slide).

Methods for enzyme immobilization are known in the art, such as adsorption, covalent or non-covalent binding, entrapment, encapsulation, and cross linking. It is desirable that a maximum enzymatic activity of the ligase is preserved after immobilization and a minimum amount of free ligase is present in the conjugate product after the conjugation reaction. Selection of the support and immobilization method is subjected to the discretion of those of skills in the art.

More preferably, the ligase is covalently immobilized to a support to reduce the amount of free ligase that falls off from the support. Methods for non-specific covalent immobilization of proteins are known in the art. In some embodiments, the support comprises chemically active functional groups that can form covalent bond with reactive groups (such as amines, thiols and carboxylates) on the ligase. Such functional groups can be selected from the group consisting of isothiocyanates, isocyanates, carbodiimides, N-Hydroxysuccinimide (NHS) esters, carbonates, epoxides, maleimides, haloacetyls, aziridines, ethyl chloroformate and aliphatic aldehydes.

Most preferably, the ligase is covalently immobilized to a support through a self-labeling protein tag such that a maximum enzymatic activity is preserved. A self-labeling protein tag is able to form covalent interaction with its substrate. Such protein tags may include, but are not limited to, SNAP tag, CLIP tag, Halo tag and variants thereof. Accordingly, the support may comprise the corresponding substrate of the protein tag. The correspondence relationship of the protein tags and their substrates are well known in the art.

In some particular embodiments, the ligase unit comprises the ligase fusion protein according to the present disclosure. In some particular embodiments, the ligase unit comprises the immobilized ligase according to the present disclosure.

Conjugate

The process can be used to prepare various kinds of conjugates. In some embodiments, the conjugate is a bioconjugate as described above.

In some embodiments, the conjugate has the structure of formula (III), the first moiety comprises T, and the second moiety comprises a linker-payload intermediate of formula (IV).

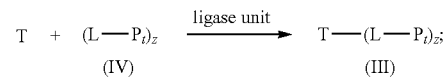

wherein

T comprises a biomolecule, which is optionally modified to have one of the recognition motif of the ligase donor substrate and the recognition motif of the ligase acceptor substrate;

L comprises a linker, which comprises the other of the recognition motif of the ligase donor substrate and the recognition motif of the ligase acceptor substrate;

P comprises a payload;

z is an integer of 1-20;

t is an integer of 1-20.

t denotes the number of payloads coupled with a single linker to form the linker-payload intermediate of formula (IV). z denotes the number of formula (IV) compounds coupled with a single T to form the compound of formula (III).

In one embodiment, z is selected from the following values: an integer of 1 to 10, 1 to 8, 1 to 6 or 1 to 4. In another embodiment, z is 1 or 2. In a very special embodiment, z is 2.

Biomolecule

In the present disclosure, the biomolecule may be selected from the group consisting of proteins, peptides, antibodies, antibody fragments, receptors, signal transduction factors, cell growth factors and nucleic acids and analogues. In one embodiment, T optionally comprises one of the recognition motif of the ligase donor substrate and the recognition motif of the ligase acceptor substrate, or is optionally modified to have one of such motifs.

In one embodiment, T is a molecule comprising a receptor, an antibody or an antibody fragment, which is optionally modified to have one of the recognition motif of the ligase donor substrate and the recognition motif of the ligase acceptor substrate. In another embodiment, T is a receptor, an antibody or an antibody fragment, which is optionally modified to have one of the recognition motif of the ligase donor substrate and the recognition motif of the ligase acceptor substrate. In a preferable embodiment, T is a molecule comprising an Fc fragment and an antigen-binding fragment of antibody, which is optionally modified to have one of the recognition motif of the ligase donor substrate and the recognition motif of the ligase acceptor substrate. In another embodiment, T is a soluble receptor, which is optionally modified to have one of the recognition motif of the ligase donor substrate and the recognition motif of the ligase acceptor substrate.

In some embodiments, T is a targeting molecule, which is optionally modified to have one of the recognition motif of the ligase donor substrate and the recognition motif of the ligase acceptor substrate. Targets recognized by the targeting molecules (such as antibodies or antigen-binding fragments thereof) include but are not limited to CD19, CD22, CD25, CD30/TNFRSF8, CD33, CD37, CD44v6, CD56, CD70, CD71, CD74, CD79b, CD117/KIT, CD123, CD138, CD142, CD174, CD227/MUC1, CD352, CLDN18.2, DLL3, ErbB2/HER2, CN33, GPNMB, ENPP3, Nectin-4, EGFRvIII, SLC44A4/AGS-5, mesothelin, CEACAM5, PSMA, TIM1, LY6E, LIV1, Nectin4, SLITRK6, HGFR/cMet, SLAMF7/CS1, EGFR, BCMA, AXL, NaPi2B, GCC, STEAP1, MUC16, Mesothelin, ETBR, EphA2, 5T4, FOLR1, LAMP1, Cadherin 6, FGFR2, FGFR3, CA6, CanAg, Integrin αV, TDGF1, Ephrin A4, Trop2, PTK7, NOTCH3, C4.4A, FLT3.

In one embodiment, the targeting molecule is an anti-human HER2 antibody or antigen-binding fragment thereof, which is optionally modified to have one of the recognition motif of the ligase donor substrate and the recognition motif of the ligase acceptor substrate. Examples of anti-human HER2 antibodies include but are not limited to Pertuzumab and Trastuzumab.

In one embodiment, the targeting molecule is one or more selected from anti-human TROP2 antibodies or antigen-binding fragment thereof, which is optionally modified to have one of the recognition motif of the ligase donor substrate and the recognition motif of the ligase acceptor substrate. In a particular embodiment, the anti-human TROP2 antibody is one or more selected from engineered anti-TROP2 antibodies based on hrS7 (US20140120035). In another particular embodiment, the anti-human TROP2 antibody is one or more selected from engineered anti-TROP2 antibodies based on MAAA1181a (US20160297890).

In a preferred embodiment, the anti-human HER2 or TROP2 antibody is a recombinant antibody selected from the group consisting of monoclonal antibody, chimeric antibody, humanized antibody, antibody fragment, and antibody mimic. In one embodiment, the antibody mimic is selected from the group consisting of scFv, minibody, diabody, nanobody. For the coupling with the compound of formula (IV), the targeting molecule of the present disclosure may comprise a modified moiety to connect with D1 or D2 in the compound of formula (V), namely the moiety in the linker which comprises a recognition motif of the ligase acceptor or donor substrate, cf. below. The introduction position of such modified moiety is not limited, for example, when the targeting molecule is an antibody, its introduction position can be, but not limited to, located at the C-terminal or the N-terminal of the heavy chain or light chain of the antibody.

In an alternative embodiment, a modified moiety for the coupling with D1 or D2 in the compound of formula (V) can be introduced at a non-terminal position of the heavy chain or light chain of the antibody using, for example, chemical modification methods.

In one embodiment, the targeting molecule of the present disclosure is an antibody or antigen-binding fragment thereof, which may comprise terminal modification. A terminal modification refers to a modification at the C-terminal or N-terminal of the heavy chain or light chain of the antibody, which for example comprises a ligase recognition motif. In another embodiment, the terminal modification may further comprise spacer Sp2 comprising 2-100 amino acids, wherein the antibody, Sp2 and the ligase recognition motif are sequentially linked. In a preferred embodiment, Sp2 is a spacer sequence containing 2-20 amino acids. In a particular embodiment, Sp2 is a spacer sequence selected from the group consisting of GA, GGGS and GGGGSGGGGS, especially GA.

In a preferred embodiment, the light chain of the antibody or antigen-binding fragment thereof includes 3 types: wild-type (LC); the C-terminus modified light chain (LCCT), which is modified by direct introduction of an ligase recognition motif LPXTG and C-terminus modified light chain (LCCT$_L$), which is modified by introduction of short peptide spacers plus the ligase donor substrate recognition motif LPXTG. The heavy chain of the antibody or antigen-binding fragment thereof includes 3 types: wild-type (HC); the C-terminus modified heavy chain (HCCT), which is modified by direct introduction of an ligase recognition motif LPXTG; and C-terminus modified heavy chain (HCCT$_L$), which is modified by introduction of short peptide spacers plus the ligase donor substrate recognition motif LPXTG. X can be any natural or non-natural single amino acid. When z in the compound of formula (IV) is 1 or 2, the combination of the above heavy and light chains can form 8 preferred antibody molecules, see the amino acid sequence table.

In a preferred embodiment, the light chain of the antibody or antigen-binding fragment thereof includes 3 types: wild-type (LC); the N-terminus modified light chain (LCNT), which is modified by direct introduction of an ligase recognition motif GGG; and N-terminus modified light chain (LCNT$_L$), which is modified by introduction of short peptide spacers plus the ligase acceptor substrate recognition motif GGG. The heavy chain of the antibody or antigen-binding fragment thereof includes 3 types: wild-type (HC); the N-terminus modified heavy chain (HCNT), which is modified by direct introduction of an ligase recognition motif GGG; and N-terminus modified heavy chain (HCNT$_L$), which is modified by introduction of short peptide spacers plus the ligase acceptor substrate recognition motif GGG.

The conjugates of the present disclosure can further comprise a payload. The payload is as described in the present disclosure.

Linker

In one embodiment, the linker, namely L in formula (III) and formula (V), is a compound of formula (V):

$$(A1_F\text{-}D1_q\text{-}Y)_i\text{-}Lk\text{-}(W\text{-}A2_q\text{-}D2_p)_i \qquad (V)$$

wherein,
D1 and D2 are independently a moiety comprising a recognition motif of the ligase acceptor or donor substrate;
A1 and A2 independently represents a bond connecting to the payload, or a moiety comprising a reactive group which can be coupled with a payload;
Lk is a chemical bond, $L_1$-$L_2$-$L_3$, or $L_1$-$L_2$-$L_3$-$L_4$, or $L_4$-$L_1$-$L_2$-$L_3$, or $L_4$;
$L_1$ and $L_3$ are each independently selected from the group consisting of:
—$CH_2$—, —NH—, —(CO)—, —NH(CO)—, —(CO)NH—; and combination of a $C_{1-4}$ alkylene with one of the following groups: —$CH_2$—, —NH—, —(CO)—, —NH(CO)—, —(CO)NH—;
$L_2$ is absent or is a $C_{7-34}$ alkylene, and wherein one or more (—$CH_2$—) structures in the alkylene is optionally replaced by —O—;
$L_1$, $L_2$ and $L_3$ are each optionally and independently substituted with 1, 2 or 3 substituents selected from —$OR_1$ and —$NR_1R_2$;
$R_1$ and $R_2$ are each independently selected from the group consisting of hydrogen, —$C_{1-6}$ alkyl, —(CO)—$C_{1-6}$ alkyl and —S(=O)$_2$—$C_{1-6}$ alkyl;
$L_4$ is a peptide sequence (amide bond is formed by the condensation reaction of α-amino and carboxyl groups), wherein it contains an optionally derivatized Lys (Lysine) (number 1-100), or contains an optionally derivatized Cys (Cysteine) (number 1-100);
Y and W are each independently absent or selected from the group consisting of a cleavable sequence, spacer Sp1, and the combination thereof;
the cleavable sequence comprises an amino acid sequence which can be cleaved by enzyme, and the cleavable sequence comprises 1-10 amino acids;
Sp1 is selected from the group consisting of a spacer sequence containing 1-20 amino acids, PAB, and the combination thereof;
p is 0 or 1, q is 0 or 1, provided that p and q are different, t is as defined in formula (III).

In one embodiment, the linker of formula (V) is connected to the payload through A1 or A2, and is connected to the biomolecule T through the coupling of D1 or D2 with the ligase acceptor substrate recognition motif comprised by the biomolecule T. Optionally, the ligase recognition motif in the biomolecule T exits in the form of a modified moiety, which is introduced to the biomolecule through, for example, recombinant methods or chemical modification methods.

In one embodiment, formula (V) is comprised by the first moiety in System 1, or comprised by the second moiety in System 2.

In one embodiment, $L_1$, $L_2$ and $L_3$ are independently substituted with 1, 2, or 3 substituents selected from —$OR_1$ and —$NR_1R_2$. Substitutions occur, for example, on (—$CH_3$), (—$CH_2$—) or

structure, especially on (—$CH_2$—).

In one embodiment, $L_2$ is a $C_{7-34}$ alkylene, wherein the alkylene is a straight or a branched alkylene group, and optionally one or more of the (—$CH_2$—) structures in the alkylene can be replaced by —O—, and the alkylene is optionally substituted with 1, 2 or 3 substituents selected from —$OR_1$ and —$NR_1R_2$. In yet another embodiment, $L_2$ is selected from groups optionally substituted with 1, 2 or 3 substituents selected from —$OR_1$ and —$NR_1R_2$, wherein the said groups are as follows: methylene, ethylene, propylene, butylene, pentylene, hexylene, 1-methylethylene, 2-methylethylene, 2-methylpropylene and 2-ethylpropylene.

In another embodiment, $L_2$ is —($C_2H_4$—O)$_i$—$C_{1-4}$ alkylene; i is an integer of 2 to 10. "—($C_2H_4$—O)$_i$—" represents a structure formed by polymerization of PEG units, wherein i indicates the number of PEG units. In another embodiment, $L_2$ is —($C_2H_4$—O)$_i$—$C_{1-2}$ alkylene. In a particular embodiment, $L_2$ is —($C_2H_4$—O)$_i$—$C_2H_4$—. In another embodiment, $L_2$ is $C_{1-4}$ alkylene-(O—$C_2H_4$)$_i$. In another embodiment, $L_2$ is $C_{1-2}$ alkylene-(O—$C_2H_4$)$_i$. In a particular embodiment, $L_2$ is —$C_2H_4$—(O—$C_2H_4$)$_i$—. In one embodiment, i is selected from the following values: 2-10, 2-8, 2-6, 2-4 or 4-6. In a particular embodiment, i is 4.

In another embodiment of $L_4$, based on the desired number of couplings, the ε-amino of lysine can either be used to introduce a maleimide functional group in A1 or A2 moieties by a suitable bifunctional crosslinking agent, or be used to form an amido bond with the α-carboxyl group of another lysine to form a branched chain, and then the α- and ε-aminos of the lysine in the branched chain can be used to introduce maleimide groups by a suitable bifunctional cross-linker. And so on, by increasing the number of the lysine in the main chain and/or branched side chain, the number of A1 or A2 moieties introduced by such a moiety $L_4$ can achieve 1-1000.

In another embodiment of $L_4$, based on the desired number of couplings, the mercapto group of each cysteine can be used to react with a maleimide functional group in A1 or A2. A1 or A2 can thus be connected to Lk. A1 and A2 each further comprises a reactive group which can be coupled with a payload. By increasing the number of the cysteine in $L_4$, for example in the main chain and/or branched side chain of $L_4$, the number of A1 or A2 moieties introduced by such a moiety $L_4$ can achieve 1-1000.

In an embodiment, $L_4$ is optionally derivatized lysine.

In a preferred embodiment, the derivatization of lysine is selected from the group consisting of: 1) amidation of the carboxyl group, the resulting amide $NH_2$ being optionally substituted with a $C_{1-6}$ alkyl group; 2) linkage of the carboxyl group and/or the amino group to an amino acid fragment comprising 1-10 amino acids or a nucleotide fragment comprising 1-10 nucleotides, wherein the amino acid fragment is preferably Gly.

In one embodiment, Y and W are each independently absent or selected from the group consisting of a cleavable sequence, spacer Sp1, and the combination thereof. In a particular embodiment, Y is absent. In another particular embodiment, W is absent. In yet another particular embodiment, Y and W are both absent. In one embodiment, the cleavable sequence comprises an amino acid sequence that can be recognized as enzyme substrate and can be cleaved by the enzyme. In a particular embodiment, the cleavable sequence can be enzymatically cleaved in the lysosomal of the cell. In another particular embodiment, the cleavable sequence can be cleaved by protease, in particular by cathepsins. In yet another particular embodiment, the cleavable sequence can be cleaved by glutaminase. In one embodiment, the cleavable sequence is selected from the group consisting of a cathepsin restriction site, a glutaminase restriction site, and combinations thereof. In one embodiment, the cleavable sequence is selected from Phe-Lys, Val-Cit, Val-Lys, Gly-Phe-Leu-Gly, Ala-Leu-Ala-Leu and the combination thereof.

In one embodiment, Y and W are each independently absent or selected from spacer Sp1. In another embodiment, Sp1 is a spacer sequence comprising 1-10, preferably 1-6, more preferably 1-4 amino acids. In a particular embodiment, Sp1 is Leu. In another particular embodiment, Sp1 is Gln. In one embodiment, Sp1 is PAB. In yet another embodiment, Y and W are each independently selected from the group consisting of Phe-Lys-PAB, Val-Cit-PAB, and Val-Lys-PAB.

In one embodiment, the amino acids comprised by Y and/or W may be natural or unnatural. In a particular embodiment, Y is absent, or is amino acid fragment 1 Amino acid fragment 1 comprises 1-30 natural or unnatural amino acids, which are each independently the same or different. And amino acid fragment 1 is selected from the group consisting of: a cleavable sequence comprising 1-10 amino acids, a spacer sequence comprising 1-20 amino acids, and the combination thereof. In another particular embodiment, W is absent, or is amino acid fragment 2. Amino acid fragment 2 comprises 1-30 natural or unnatural amino acids, which are each independently the same or different. And amino acid fragment 2 is selected from the group consisting of: a cleavable sequence comprising 1-10 amino acids, a spacer sequence comprising 1-20 amino acids, and the combination thereof.

In one embodiment, p=0, q=1, the structure of the compound of formula (V) is as shown in the following formula (V-1):

D1-Y-Lk-(W-A2)$_t$     (V-1)

wherein, A2, D1, Y, Lk, and W are as defined in formula (V), respectively.

In another embodiment, p=1, q=0, the structure of the compound of formula (III) is as shown in the following formula (V-2):

(A1-Y)$_t$-Lk-W-D2     (V-2)

wherein, A1, D2, Y, Lk and W are as defined in formula (V), respectively.

In an embodiment, suitable linker can be selected from those in any one of FIGS. 13 to 16 in WO2014177042A. In yet another embodiment, suitable linker can be selected from those in any one of FIGS. 7 to 10 in WO2015165413A.

In an embodiment, suitable linker can be selected from those in any one of FIGS. 1 to 12 in WO2014177042A. In yet another embodiment, suitable linker can be selected from those in any one of FIGS. 3 to 6 in WO2015165413A.

Moiety Comprising Recognition Motif of the Ligase Acceptor or Donor Substrate

In one embodiment, the ligase is a transpeptidase. In one embodiment, the ligase is selected from the group consisting of a natural transpeptidase, an unnatural transpeptidase, variants thereof, and the combination thereof. Unnatural transpeptidase enzymes can be, but are not limited to, those obtained by engineering of natural transpeptidase.

In a preferred embodiment, the ligase is selected from the group consisting of a natural Sortase, an unnatural Sortase, and the combination thereof. The species of natural Sortase include SrtA, Srt B, SrtC, SrtD, SrtE, SrtF, etc. (see, e.g., US20110321183A1 and EP3647419A1). The type of ligase corresponds to the ligase recognition motif and is thereby used to achieve specific coupling between different molecules or structural fragments.

In one embodiment, the recognition motif of the ligase acceptor substrate is selected from the group consisting of oligomeric glycine, oligomeric alanine, and a mixture of oligomeric glycine/alanine having a degree of polymerization of 3-10. In a particular embodiment, the recognition motif of the ligase acceptor substrate is $G_n$, wherein G is glycine (Gly), and n is an integer of 3 to 10.

In some embodiments, the ligase is a SrtA, and the donor recognition motif can be LPXTG, wherein X is any natural or unnatural amino acid. In some embodiments, the ligase is a SrtB, and the donor recognition motif can be NPXTG, wherein X is any natural or unnatural amino acid. In some embodiments, the ligase is a SrtC, and the donor recognition motif can be LPXTG, wherein X is any natural or unnatural amino acid. In some other embodiments, the ligase is a SrtD, and the donor recognition motif can be LPXTA, wherein X is any natural or unnatural amino acid. In yet some other embodiments, the ligase is a SrtE, and the donor recognition motif can be LAXTG, wherein X is any natural or unnatural amino acid. In some other embodiments, the ligase is a SrtF, and the donor recognition motif can be LPXTG, wherein X is selected from the group consisting of A, R, N, D, Q, I, L and K.

In another particular embodiment, the ligase is a SrtA from *Staphylococcus aureus*. Accordingly, the ligase recognition motif may be the typical recognition motif LPXTG of the enzyme. In yet another particular embodiment, the recognition motif of the ligase donor substrate is LPXTGJ, and the recognition motif of the ligase acceptor substrate is $G_n$, wherein X can be any single amino acid that is natural or unnatural; J is absent, or is an amino acid fragment comprising 1-10 amino acids, optionally labeled. In one embodiment, J is absent. In yet another embodiment, J is an amino acid fragment comprising 1-10 amino acids, wherein each amino acid is independently any natural or unnatural amino acid. In another embodiment, J is $G_m$, wherein m is an integer of 1 to 10. In yet another particular embodiment, the recognition motif of the ligase donor substrate is LPETG. In another particular embodiment, the recognition motif of the ligase donor substrate is LPETGG. In one embodiment, the ligase is SrtB from *Staphylococcus aureus* and the corresponding donor substrate recognition motif can be NPQTN. In another embodiment, the ligase is SrtB from *Bacillus anthracis* and the corresponding donor substrate recognition motif can be NPKTG. In yet another embodiment, the ligase is SrtA from *Streptococcus pyogenes* and the corresponding donor substrate recognition motif can be LPXTGJ, wherein J is as defined above. In another embodiment, the ligase is SrtE from *Streptomyces coelicolor*, and the corresponding donor substrate recognition motif can be LAXTG. In yet another embodiment, the ligase is SrtA from *Lactobacillus plantarum* and the corresponding donor substrate recognition motif can be LPQTSEQ. The ligase recognition motif can also be other totally new recognition sequence for transpeptidase optimized by manual screening.

When coupling LPXTGJ with $G_n$, the upstream peptide bond of the glycine in the LPXTGJ sequence is cleaved by Sortase A, and the resulting intermediate is linked to the free N-terminal of $G_n$ to generate a new peptide bond. The resulting amino acid sequence is $LPXTG_n$. The sequences $G_n$ and LPXTGJ are as defined above.

In some particular embodiments, the ligase is a SrtA from *Staphylococcus aureus*, the donor recognition motif is LPETGG, the acceptor recognition motif is GGG.

Moiety Comprising Reactive Group

In one embodiment, A1 and A2 in formula (V) are each independently selected from the group consisting of amino compound, maleimide and derivative thereof, thiol compound, pyridyldithiol compound, haloacetic acid (haloacetylic acid), isocyanate. In another embodiment, the reactive groups in A1 and A2 are each independently selected from the group consisting of amino group, maleimide group, thiol group, pyridyldithio group, haloacetyl group, and isocyanate group.

In an embodiment, according to the structure of the reactive group therein, A1 and A2 can each independently covalently couple with a Michael acceptor (the acceptor molecule of Michael addition) through a disulfide bond, a thioether bond, a thioester bond, or a urethane bond. In a particular embodiment, A1 and A2 are each independently selected from optionally derivatized cysteines.

In another particular embodiment, A1 and A2 are each independently selected from optionally derivatized cysteines. In a preferred embodiment, the derivatization of cysteine is selected from the group consisting of: 1) amidation of the carboxyl group, the resulting amide $NH_2$ being optionally substituted with a $C_{1-6}$ alkyl group; 2) acylation of the amino group; and 3) linkage of the carboxyl group and/or the amino group to an amino acid fragment comprising 1-10 amino acids or a nucleotide fragment comprising 1-10 nucleotides, wherein the amino acid fragment is preferably Gly. In a particular embodiment, the derivatization of cysteine refers to amidation or linkage to glycine for the carboxyl group of cysteine.

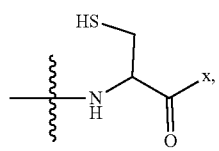

In one embodiment, A2 is wherein x is selected from the group consisting of hydrogen, OH, $NH_2$, an amino acid fragment comprising 1-10 amino acids, and a nucleotide fragment comprising 1-10 nucleotides. In one embodiment, A1 is

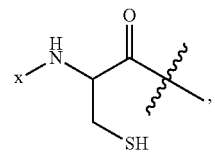

wherein x is selected from the group consisting of hydrogen, an amino acid fragment comprising 1-10 amino acids, and a nucleotide fragment comprising 1-10 nucleotides. In one embodiment, acylation of the amino group refers to the substitution with a $C_{1-6}$ alkylcarbonyl group for the amino group of cysteine.

In some embodiments of the linking unit of formula (V-1), wherein t is 1, D1 is $G_n$, G is glycine, A2 is

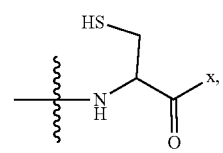

and the structure of the compound of formula (V-1) is as shown in the following formula (V-1-1):

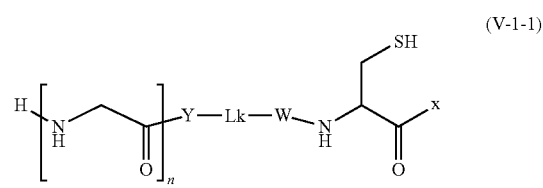

(V-1-1)

wherein n is an integer of 3 to 10;
x is selected from the group consisting of hydrogen, OH, $NH_2$, an amino acid fragment comprising 1-10 amino acids, a nucleotide fragment comprising 1-10 nucleotides;
Lk is $L_1$-$L_2$-$L_3$;
$L_1$, $L_2$, $L_3$, t, Y and W are as defined in formula (V), respectively.

In a preferred embodiment, in formula (V-1-1), x is selected from OH, $NH_2$ and Gly.

In a particular embodiment, in formula (V-1-1), both Y and W are absent, Lk is $L_1$-$L_2$-$L_3$, $L_1$ is —NH—, $L_3$ is —(CO)—, $L_2$ is —$(C_2H_4$—O$)_i$—$C_2H_4$—, i=4, and the structure of the compound of formula (V-1-1) is as shown in the following formula (V-1-1-1):

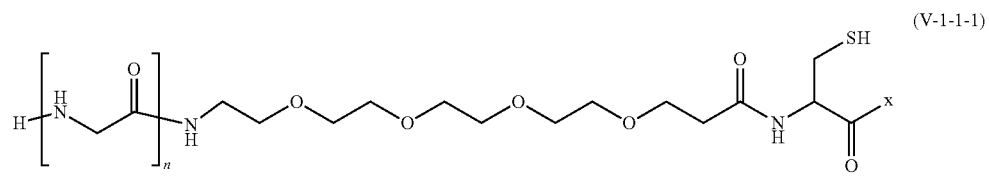

(V-1-1-1)

In a particular embodiment, in formula (V-1-1), W is absent, Y is L, L is leucine (Leu), Lk is $L_1$-$L_2$-$L_3$, $L_1$ is —NH—, $L_3$ is —(CO)—, $L_2$ is —($C_2H_4$—O)$_i$—$C_2H_4$—, i=4, and the structure of the linking unit is as follows (V-1-1-2):

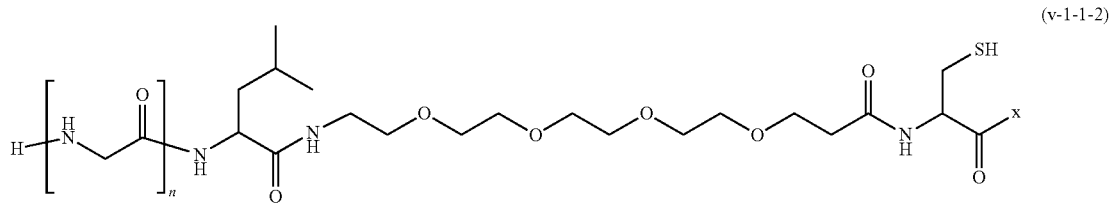

In yet a particular embodiment, in formula (V-1-1), W is absent, Y is Q, Q is glutamine (Gln), Lk is $L_1$-$L_2$-$L_3$, $L_1$ is —NH—, $L_3$ is —(CO)—, $L_2$ is —($C_2H_4$—O)$_i$—$C_2H_4$—, i=4, and the structure of the linking unit is as follows (V-1-1-3):

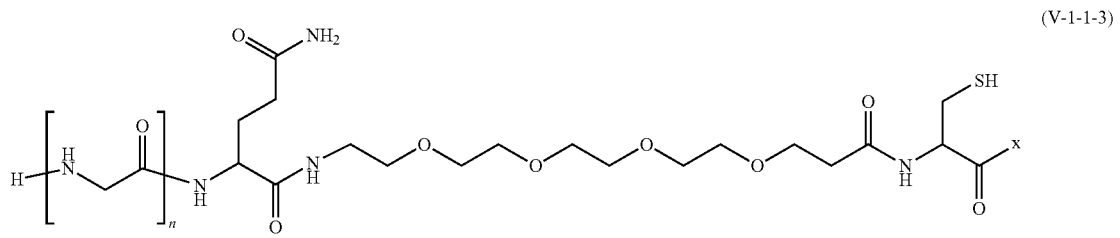

In a particular embodiment, in formula (V-1-1), both Y and W are absent, Lk is $L_1$-$L_2$-$L_3$, $L_1$ is —NH—, $L_3$ is —(CO)—, $L_2$ is —$C_5H_{10}$—, and the structure of the linking unit is as follows (V-1-1-4):

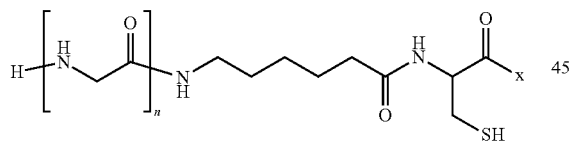

In yet a particular embodiment, in formula (V-1-1), both Y and W are absent, Lk is $L_1$-$L_2$-$L_3$, $L_1$ is —NH—, $L_3$ is —(CO)—, $L_2$ is —$C_5H_{10}$— group substituted with one —$NR_1R_2$ group, $R_1$ is hydrogen, $R_2$ is —(CO)$CH_3$, and the structure of the linking unit is as follows (V-1-1-5):

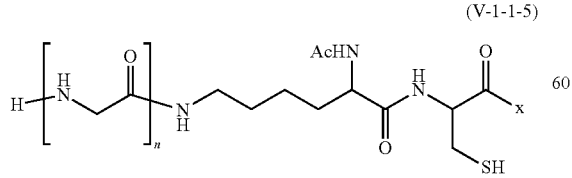

In some embodiments of the linking unit of formula (V-2), when t is 1, D2 is LPXTG and A1 is the structure of the compound of formula (V-2) is as shown in the following formula (V-2-1):

$$\text{(V-2-1)}$$

wherein x is selected from hydrogen, an amino acid fragment comprising 1-10 amino acids, a nucleotide fragment comprising 1-10 nucleotides;
Lk is $L_1$-$L_2$-$L_3$;
$L_1$, $L_2$, $L_3$, Y and W are as defined in formula (V), respectively.
In one embodiment, x is hydrogen.
In one embodiment, A1 and A2 are each independently a maleimide functional group. The maleimide functional group is introduced into the molecule of formula (V) by a suitable bifunctional cross-linking agent.
In a preferred embodiment, the bifunctional cross-linking agent for introducing maleimide functional group include, but are not limited to, N-succinimidyl 4-(N-maleimidomethyl) cyclohexane-1-carboxylate (SMCC), the "long chain" SMCC analogue N-[alpha-maleimidoacetoxy] succinimide ester (AMAS), N-gamma-Maleimidobutyryl-oxysuccinimide ester (GMBS), 3-MaleiMidobenzoic acid N-hydroxysucciniMide ester (MBS), 6- maleimidohexanoic acid N-hydroxysuccinimide ester (EMCS), N-succinimidyl 4-(4-maleimidophenyl) butyrate (SMPB), Succinimidyl 6-[(beta-maleimidopropionamido) hexanoate (SMPH), Succinimidyl 4-(N-maleimidomethyl) cyclohexane-1-carboxy-(6-amido-caproate) (LC-SMCC), N-succinimidyl 11-(maleimido) undecanoate (KMUS), and a bifunctional crosslinking agent comprising N-hydroxy succinimide-(polyethyleneglycol alcohol)$_n$ (SM (PEG)$_n$), wherein n indicated there are 2, 4, 6, 8, 12 or 24 polyethylene glycol (PEG) units. The exemplary maleimide functional groups introduced to A1 or A2 immediately after reacting with bifunctional cross-linking agent may be those listed in the following table:

| Bifunctional cross-linking agent | Exemplary maleimide functional group introduced to A1 or A2 |
|---|---|
| SMCC | mcc |
| AMAS | |
| GMBS | |
| MBS | |
| EMCS | mc |
| SMPB | |
| SMPH | |
| LC-SMCC | |
| KMUS | |
| a bifunctional crosslinking agent comprising SM (PEG)$_n$ | a maleimide functional group comprising (PEG)$_n$ |

In one embodiment, A1 and A2 are each independently selected from mc and mcc.

In some embodiments of the linker of formula (V-1), wherein t is 1, D1 is G$_n$, G is glycine, A2 is mcc, W is absent, Lk is L$_4$, L$_4$ is an optionally derivatized lysine, and the structure of the compound of formula (V-1) is as shown in the following formula (V-1-2):

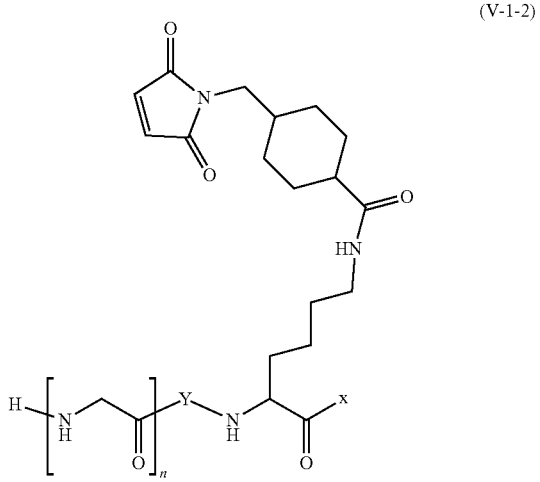

(V-1-2)

wherein n is an integer of 3 to 10;

x is selected from the group consisting of hydrogen, OH, $NH_2$, an amino acid fragment comprising 1-10 amino acids, a nucleotide fragment comprising 1-10 nucleotides;

Y is as defined in formula (V).

In a particular embodiment, in formula (V-1-2), Y is absent, n=3, x is OH, and the structure of the linker is as follows (linker LU104):

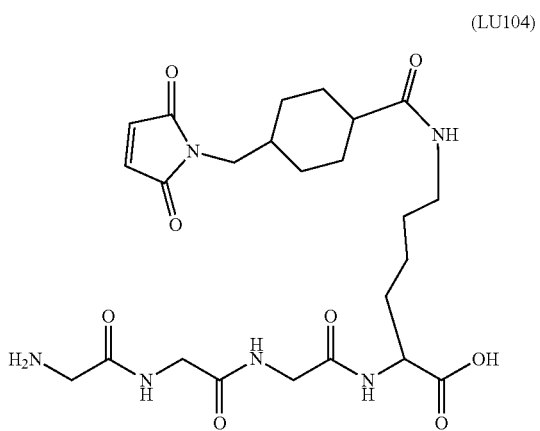 [SMILES: NCC(=O)NCC(=O)NCC(=O)NC(CCCCNC(=O)C1CCC(CN2C(=O)C=CC2=O)CC1)C(=O)O]

(LU104)

Payload

In the present disclosure, the payload may be selected from the group consisting of hydrogen, small molecule compounds (e.g., inhibitors and toxins (such as cytotoxins)), glycans, PEG moieties, radionuclides, cytokines, immunomodulators, nucleic acids and analogues (e.g., interfering RNAs), tracer molecules (e.g., fluorophores and fluorescent molecules), polypeptides (e.g., protein tags, bioactive peptides, protein toxins and enzymes), peptidomimetics, antibodies and antibody fragments.

In some embodiments, the payload is selected from the group consisting of small molecule compounds, immunomodulators, nucleic acids and analogues, tracer molecules, radionuclides, peptidomimetics, glycans, and PEG moieties.

In some embodiments, the payload is selected from the group consisting of bioactive peptides, cytokines, antibodies, antibody fragments and protein receptors.

In one embodiment, the payload is selected from the group consisting of small molecule compounds, nucleic acid molecules, and tracer molecules. In a preferred embodiment, the payload is selected from small molecule compounds. In a more preferred embodiment, the payload is selected from the group consisting of cytotoxin and fragments thereof. In an embodiment, the payload is one or more radionuclides. In another embodiment, the payload is one or more cytokines. In an embodiment, the payload is one or more immunomodulators.

In one embodiment, the cytotoxin is selected from the group consisting of drugs that target microtubule cytoskeleton. In a preferred embodiment, the cytotoxin is selected from the group consisting of taxanes, maytansinoids, auristatins, epothilones, combretastatin A-4 phosphate, combretastatin A-4 and derivatives thereof, indol-sulfonamides, vinblastines such as vinblastine, vincristine, vindesine, vinorelbine, vinflunine, vinglycinate, anhy-drovinblastine, dolastatin 10 and analogues, halichondrin B and eribulin, indole-3-oxo acetamide, podophyllotoxins, 7-diethylamino-3-(2'-benzoxazolyl)-coumarin (DBC), discodermolide, laulimalide. In another embodiment, the cytotoxin is selected from the group consisting of DNA topoisomerase inhibitors such as camptothecins and derivatives thereof, mitoxantrone, mitoguazone. In a preferred embodiment, the cytotoxin is selected from the group consisting of nitrogen mustards such as chlorambucil, chlornaphazine, cholophosphamide, estramustine, ifosfamide, mechlorethamine, mechlorethamine oxide hydrochloride, melphalan, novembichin, phenamet, phenesterine, prednimustine, trofosfamide, uracil mustard. In yet another preferred embodiment, the cytotoxin is selected from the group consisting of nitrosoureas such as carmustine, flubenzuron, formoterol, lomustine, nimustine, ramustine. In one embodiment, the cytotoxin is selected from the group consisting of aziridines. In a preferred embodiment, the cytotoxin is selected from the group consisting of benzodopa, carboquone, meturedepa, and uredepa. In one embodiment, the cytotoxin is selected from the group consisting of an anti-tumor antibiotic. In a preferred embodiment, the cytotoxin is selected from the group consisting of enediyne antibiotics. In a more preferred embodiment, the cytotoxin is selected from the group consisting of dynemicin, esperamicin, neocarzinostatin, and aclacinomycin. In another preferred embodiment, the cytotoxin is selected from the group consisting of actinomycin, antramycin, bleomycins, actinomycin C, carabicin, carminomycin, and cardinophyllin, carminomycin, actinomycin D, daunorubicin, detorubicin, adriamycin, epirubicin, esorubicin, idarubicin, marcellomycin, mitomycins, nogalamycin, olivomycin, peplomycin, porfiromycin, puromycin, ferric adriamycin, rodorubicin, rufocromomycin, streptozocin, zinostatin, zorubicin. In yet another preferred embodiment, the cytotoxin is selected from the group consisting of trichothecene. In a more preferred embodiment, the cytotoxin is selected from the group consisting of T-2 toxin, verracurin A, bacillocporin A, and anguidine. In one embodiment, the cytotoxin is an anti-tumor amino acid derivative. In a preferred embodiment, the cytotoxin is selected from the group consisting of ubenimex, azaserine, 6-diazo-5-oxo-L-norleucine. In another embodiment, the cytotoxin is selected from the group consisting of folic acid analogues. In a preferred embodiment, the cytotoxin is selected from the group consisting of dimethyl folic acid, methotrexate, pteropterin, trimetrexate, and edatrexate. In one embodiment, the cytotoxin is selected from the group consisting of purine analogues. In a preferred embodiment, the cytotoxin is selected from the group consisting of fludarabine, 6-mercaptopurine, tiamiprine, thioguanine. In yet another embodiment, the cytotoxin is selected from pyrimidine analogues. In a preferred embodiment, the cytotoxin is selected from the group consisting of ancitabine, gemcitabine, enocitabine, azacitidine, 6-azauridine, carmofur, cytarabine, dideoxyuridine, doxifluridine, floxuridine. In one embodiment, the cytotoxin is selected from the group consisting of androgens. In a preferred embodiment, the cytotoxin is selected from the group consisting of calusterone, dromostanolone propionate, epitiostanol, mepitiostane, testolactone. In another embodiment, the cytotoxin is selected from the group consisting of anti-adrenals. In a preferred embodiment, the cytotoxin is selected from the group consisting of aminoglutethimide, mitotane, and trilostane. In one embodiment, the cytotoxin is selected from the group consisting of anti-androgens. In a preferred embodiment, the cytotoxin is selected from the group consisting of flutamide, nilutamide, bicalutamide, leuprorelin acetate, and goserelin. In yet another embodiment, the cytotoxin is selected from the group consisting of a protein kinase inhibitor and a proteasome inhibitor. In a particularly embodiment, the cytotoxin is selected from the group consisting of vinblastines, colchicines, taxanes, auristatins, and maytansinoids. In a particular embodiment, the cytotoxin is an auristatin, such as MMAE (monomethyl auristatin E), MMAF (monomethyl auristatin F), MMAD (monomethyl auristatin D) and the like. The synthesis and structure of auristatin compounds are described in US20060229253, the entire disclosure of which is incorporated herein by reference.

The payload contains a reactive group which can react with the reactive group in the compound of formula (V) and thus covalently couple the payload with the compound of formula (V). Compounds that do not contain reactive groups require appropriate derivatization to give the payload. In one embodiment, the reactive group in the payload is maleimide, and the compound without maleimide may be subjected to suitable reaction(s) to give a maleimide derivative. For example, MMAF is derivatized to give mc-MMAF (mc is maleimidocaproyl). MMAE is derivatized to give mc-Val-Cit-PAB-MMAE. mc in the above structures can be replaced by mcc (4-(maleimidomethyl)cyclohexane-1-carbonyl) or maleimide-R structure, wherein R is a $C_{1-20}$ alkylene, and optionally one or more (—$CH_2$—) structures in the alkylene can be replaced by —O—;

In an embodiment, step (a) comprises: obtaining System 2 through reacting the linker of formula (V) with the payload. Preferably, the compound of formula (V) is each independently covalently linked via a reactive group comprised by moiety A1 or A2 to another reactive group comprised by the payload, forming the linker-payload intermediate of formula (IV).

The reactive groups comprised by moiety A1 or A2 are as described above.

In a particular embodiment, the covalently link formed between the compound of formula (V) and the payload is one or more bonds selected from amide bonds, disulfide bonds, thioether bonds, thioester bonds, peptide bonds, hydrazone bonds, ester bonds, ether bonds and urethane bonds.

In an embodiment, the reactive group in A1 or A2 in the compound of formula (V) is a maleimide or maleimide derivative, and the other reactive group in the payload is a Michael acceptor. And after the reaction with the payload, the maleimide or maleimide derivative turns into a succinimide or succinimide derivative.

In an embodiment, p=0, q=1, the intermediate of formula (IV) is as shown in the following formula (IV-1):

D1-Y-Lk-(W-A2-P)$_t$      (IV-1)

In another embodiment, p=1, q=0, the structure of the compound of formula (IV) is as shown in the following formula (IV-2):

(P-A1-Y)$_t$-Lk-W-D2      (IV-2)

In an embodiment, the linker-payload intermediate of formula (IV) which contains a succinimide or succinimide derivative may be subjected to ring-opening reaction, so as to obtain a "ring-open" intermediate. The ring-opening reaction could be performed through a method similar to that described in WO2015165413A. The ring-open intermediates are also included in the scope of formula (IV).

In an embodiment, the ring-opening reaction of the succinimide in the linker-payload intermediate of formula (IV) forms ring-open intermediate as shown in the following formula (IV-1-2). Formula (IV-1-2) falls in the scope of formula (IV-1).

D1-Y-Lk-(W-A2open-P)$_t$      (IV-1-2)

In another embodiment, the ring-opening reaction of the succinimide ring in the linker-payload intermediate of formula (IV) forms ring-open intermediate as shown in the following formula (IV-2-2). Formula (IV-2-2) falls in the scope of formula (IV-2).

(P-A1open-Y)$_t$-Lk-W-D2      (IV-2-2)

Wherein, "-A1open-" and "-A2open-" has a structure selected from

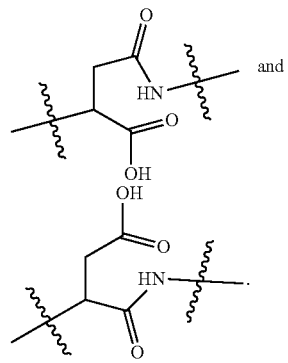

Specific Embodiments for the Linker-Payload Intermediate

In one embodiment, A1 and A2 are each independently selected from mc and mcc, and the maleimide functional group contained therein is linked to a thiol group in the payload (P), and the linker and the payload are thereby connected to each other through a thiosuccinimide structure (thiosuccinimide linkage). The succinimide ring in the thiosuccinimide linkage may be subjected to ring-opening reaction as described above, and obtain a ring-open thiosuccinimide structure

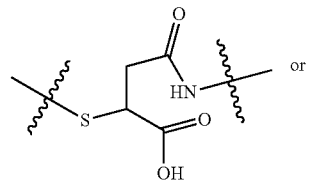

-continued

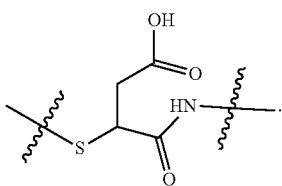

In an embodiment, the structure of L is as defined in formula (V-1-1), and the linker-payload intermediate of formula (IV-1) has the structure of formula (IV-1-1). The linker-payload intermediate of formula (IV-1-1) may be prepared through reaction of the corresponding linker of formula (V-1-1) with the payload (P).

In a specific embodiment, in formula (IV-1), D1 is $G_n$, G is glycine, A2 is

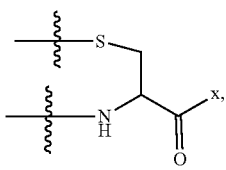

Lk is $L_4$, $L_4$ is an optionally derivatized lysine, D2 is $G_n$, G is glycine, and the linker-payload intermediate has the structure as shown in the following formula (IV-1-1):

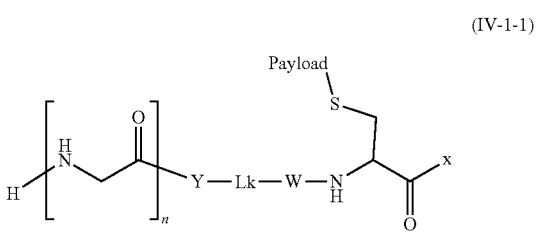

(IV-1-1)

In a preferred embodiment, in formula (IV-1-1), Y and W are both absent, the payload is mc(ring open)-Toxin, and the linker-payload intermediate has the structure as shown in the following formula (IV-1-2) or formula (IV-1-2'):

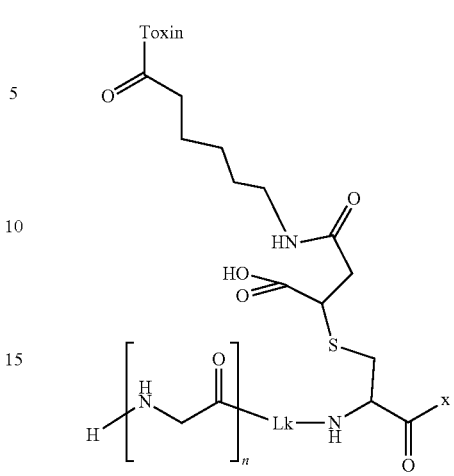

(IV-1-2)

(IV-1-2')

wherein Toxin represents a cytotoxin as defined in formula (III); n, Lk and x are as defined in formula (IV-1-1), respectively.

In a more preferred embodiment, in formula (IV-1-2) and formula (IV-1-2'), the cytotoxin is MMAF, i.e., the payload is mc(ring open)-MMAF, and the linker-payload intermediate has the structure as shown in the following formula (IV-1-3) or formula (IV-1-3'):

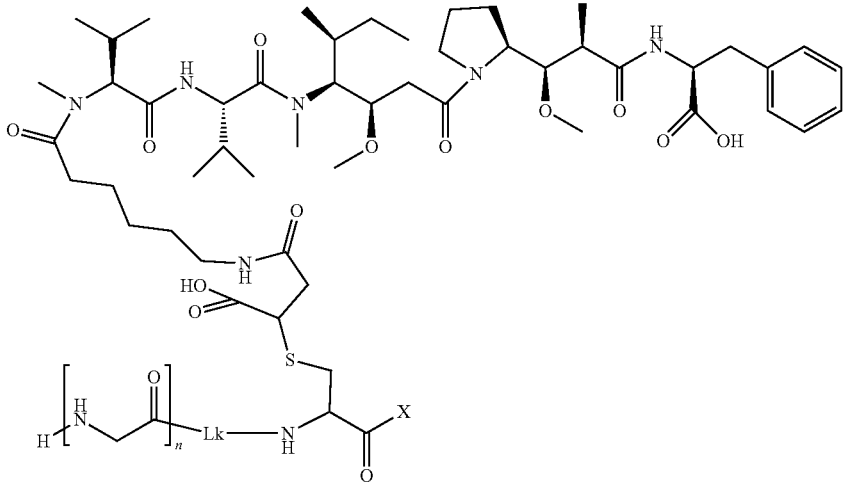

(IV-1-3)

(IV-1-3′)
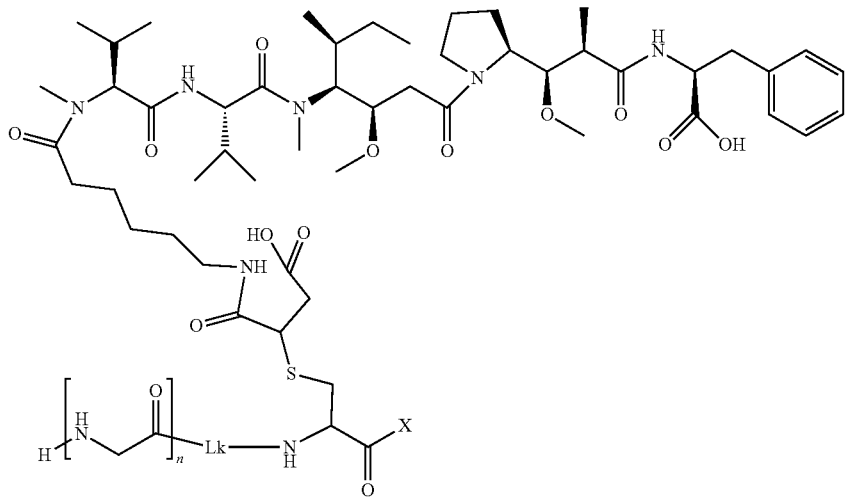
Formulae (IV-1-3) and (IV-1-3′) are isomers, wherein:
T, n, Lk and x are as defined in formula (IV-1-1), respectively.
In another specific embodiment, in formulae (IV-1-3) and (IV-1-3′), Lk is $L_1$-$L_2$-$L_3$, $L_1$ is —NH—, and $L_3$ is —(CO)—, $L_2$ is —($C_2H_4$—O)$_i$—$C_2H_4$—, i=4, and the linker-payload intermediate has the structure as shown in the following formula (IV-1-4) and (IV-1-4′):
(IV-1-4)
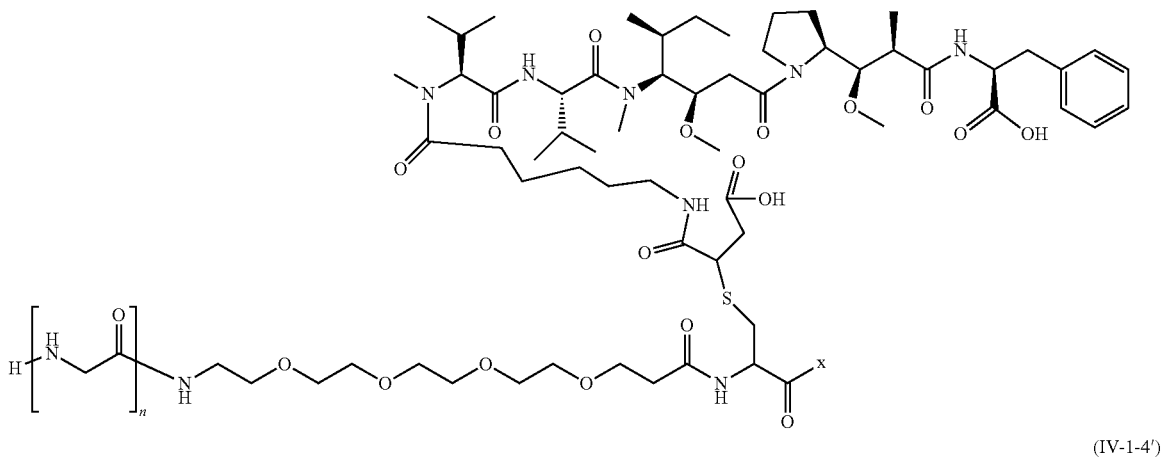
(IV-1-4′)
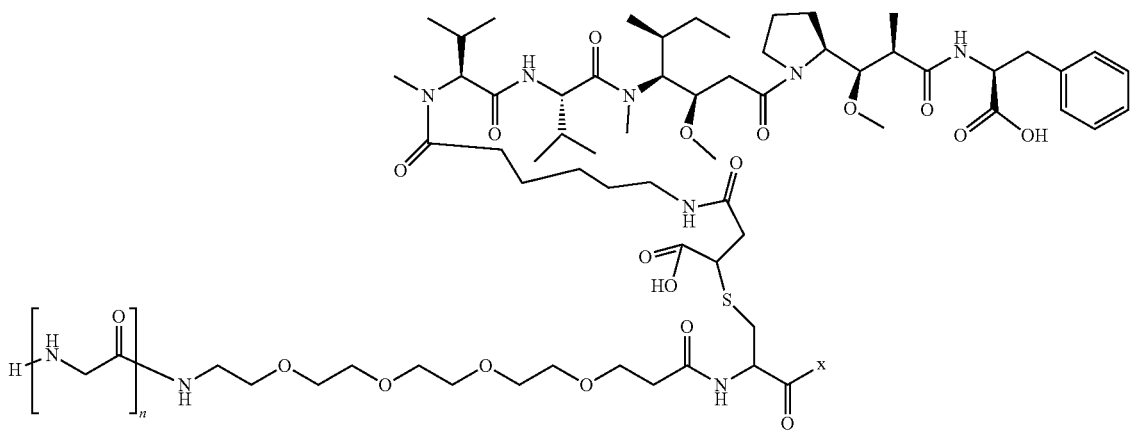

Formulae (IV-1-4) and (IV-1-4') are isomers, wherein:

n and x are as defined in formula (IV-1-1), respectively.

In a specific embodiment, in formula (IV-1), W does not exist, t is 1, the payload is Toxin, A1 is mcc, Lk is $L_4$, $L_4$ is an optionally derivatized lysine, D2 is $G_n$, G is glycine, and the linker-payload intermediate has the structure as shown in the following formula (IV-1-5-1):

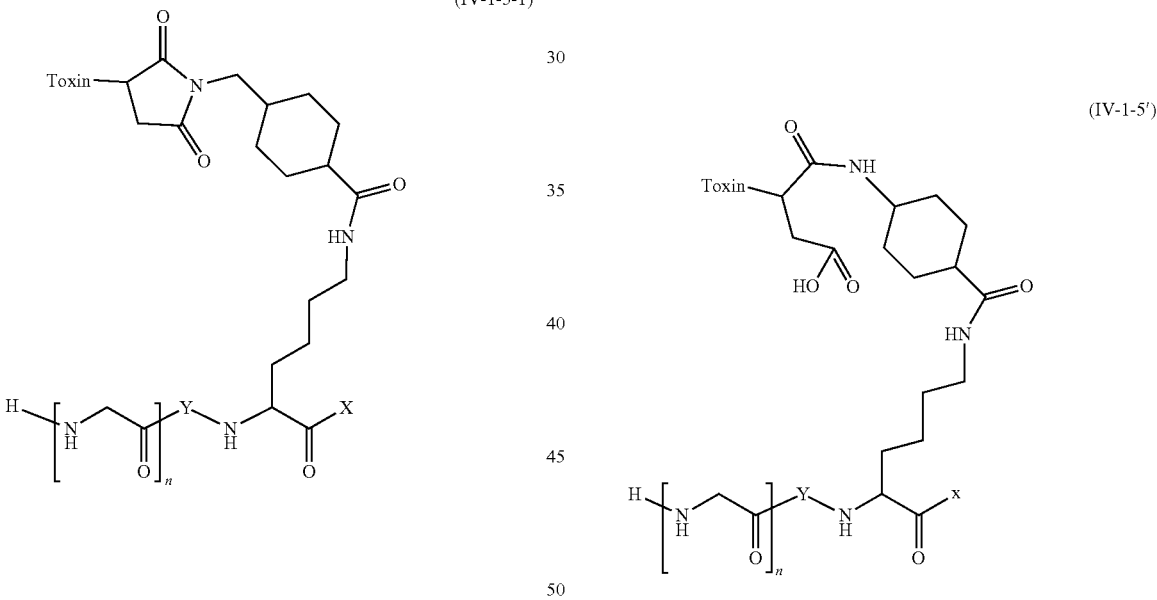

wherein Toxin, n, Y and x are as defined above.

In one embodiment, the linker-payload intermediate has the structure as shown in the following formula (IV-1-5) or (IV-1-5'):

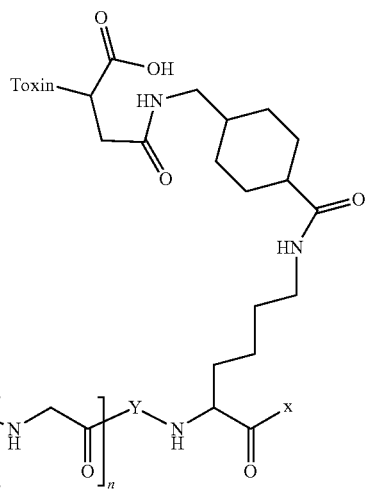

wherein Toxin, n, Y and x are as defined above.

The linker-payload intermediate of formulae (IV-1-5) and (IV-1-5') may be prepared through ring-opening reaction of formula (IV-1-5-1).

In a preferred embodiment, the Toxin is a maytansinoid, preferably DM1.

In a specific embodiment, in formulae (IV-1-5) and (IV-1-5'), the cytotoxin is DM1, Y does not exist, and the linker-payload intermediate has the structure as shown in the following formula (IV-1-6) or (IV-1-6'). Formula (IV-1-6) falls in the scope of formula (IV-1-5), and formula (IV-1-6') falls in the scope of formula (IV-1-5').

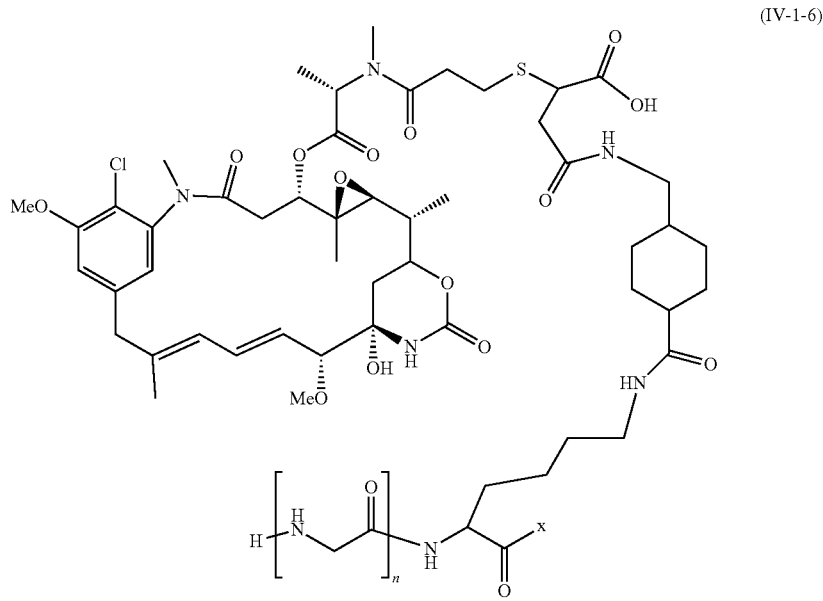

(IV-1-6)

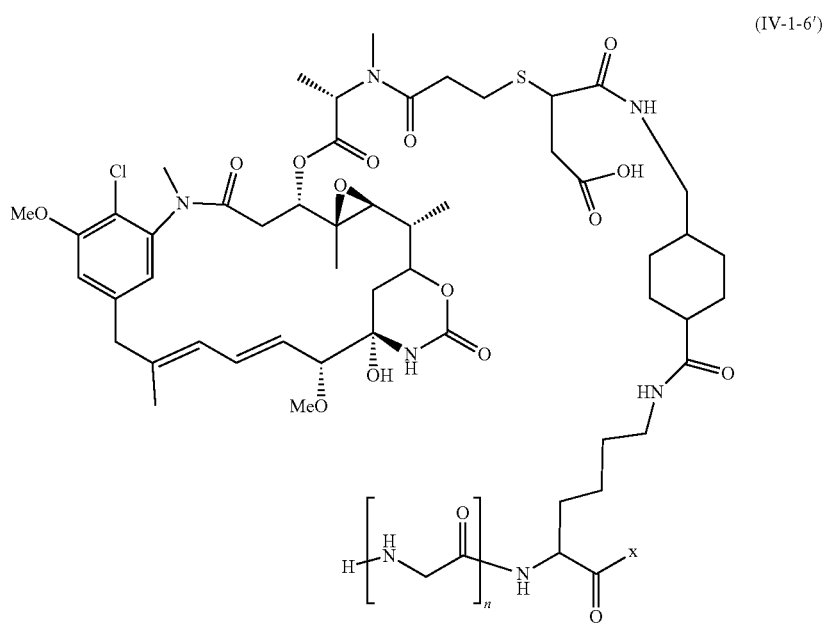

(IV-1-6')

wherein n and x are as defined above.

Specific Embodiments for the Conjugate

In an embodiment, t is 1, and the conjugate has the structure selected from the following formulas (1), (2), (2'), (3), (3'), (4), (4'), (5), (5'), (6), (6').

In an embodiment, the structure of L-P is as defined in formula (V-1-1), and the conjugate of formula (III) has the structure of formula (1). The conjugate of formula (1) may be prepared through conjugation reaction of the corresponding linker-payload intermediate of formula (V-1-1) with the biomolecule (T).

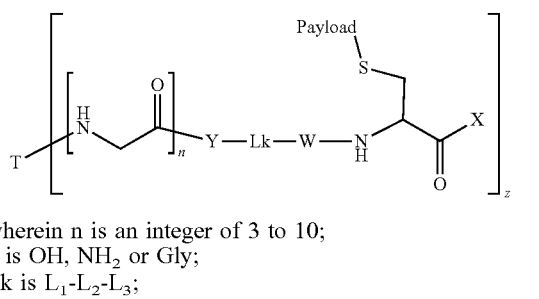

Formula (1)

wherein n is an integer of 3 to 10;
x is OH, $NH_2$ or Gly;
Lk is $L_1$-$L_2$-$L_3$;

T, Payload and z are as defined in formula (III), respectively; $L_1$, $L_2$, $L_3$, Y and W are as defined in formula (V), respectively.

In an embodiment, the structure of L-P is as defined in formulae (IV-1-2) or (IV-1-2'), and the conjugate of formula (III) has the structure selected from the following formulae (2) and (2'). In a specific embodiment, the structure of L-P is as defined in formulae (IV-1-3) or (IV-1-3'), and the conjugate of formula (III) has the structure selected from the following formulae (3) and (3'). In a more specific embodiment, the structure of L-P is as defined in formulae (IV-1-4) or (IV-1-4'), and the conjugate of formula (III) has the structure selected from the following formulae (4) and (4'). Formula (4) falls in the scope of formula (3), formula (3) falls in the scope of formula (2), and formula (2) falls in the scope of formula (1). Formula (4') falls in the scope of formula (3'), formula (3') falls in the scope of formula (2'), and formula (2') falls in the scope of formula (1').

In a preferred embodiment, Y and W are both absent, the payload in formula (1) is mc(ring open)-toxin, and the structure of the conjugate is as shown in the following formula (2) or formula (2'):

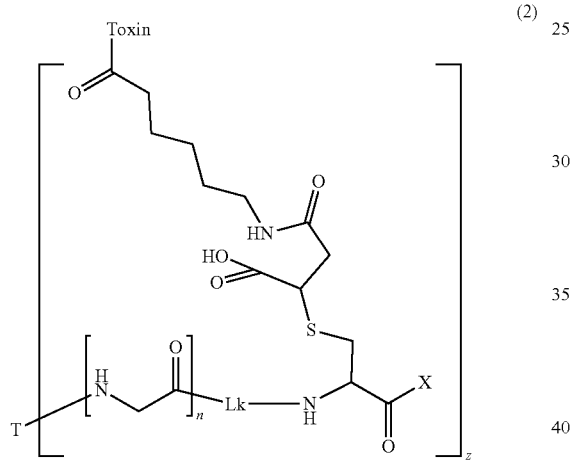

(2)

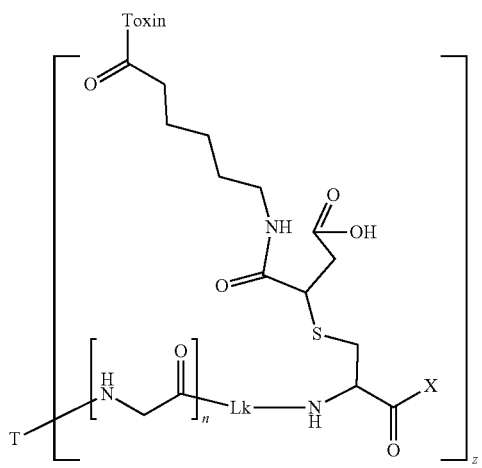

(2')

wherein Toxin represents a cytotoxin as defined in formula (III); T, n, Lk, x and z are as defined in formula (1), respectively.

In a more preferred embodiment, the cytotoxin in formula (2) and formula (2') is MMAF, i.e., the payload is mc(ring open)-MMAF, and the structure of the conjugate is as shown in the following formula (3) or formula (3'):

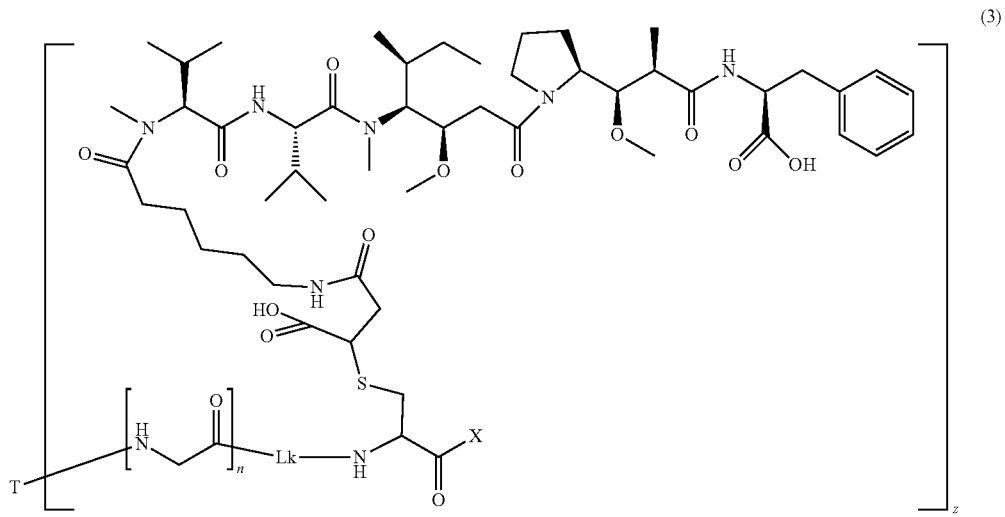

(3)

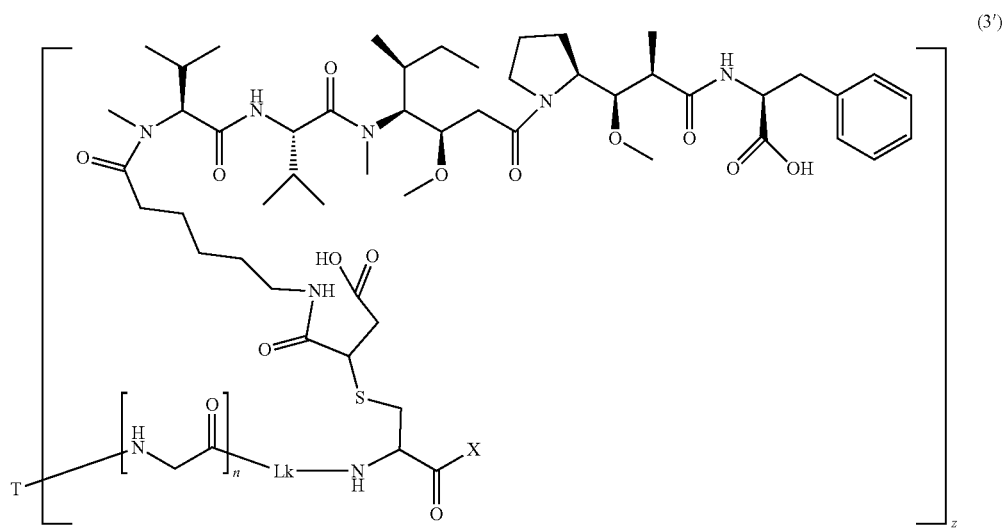
(3')
Formulae (3) and (3') are isomers, wherein:
T, n, Lk, x and z are as defined in formula (1), respectively.
In another specific embodiment, Lk is $L_1$-$L_2$-$L_3$, $L_1$ is —NH—, and $L_3$ is —(CO)—, $L_2$ is —($C_2H_4$—O)$_i$—$C_2H_4$—, i=4. The structure of the conjugate is as shown in the following formula (4) and (4'):
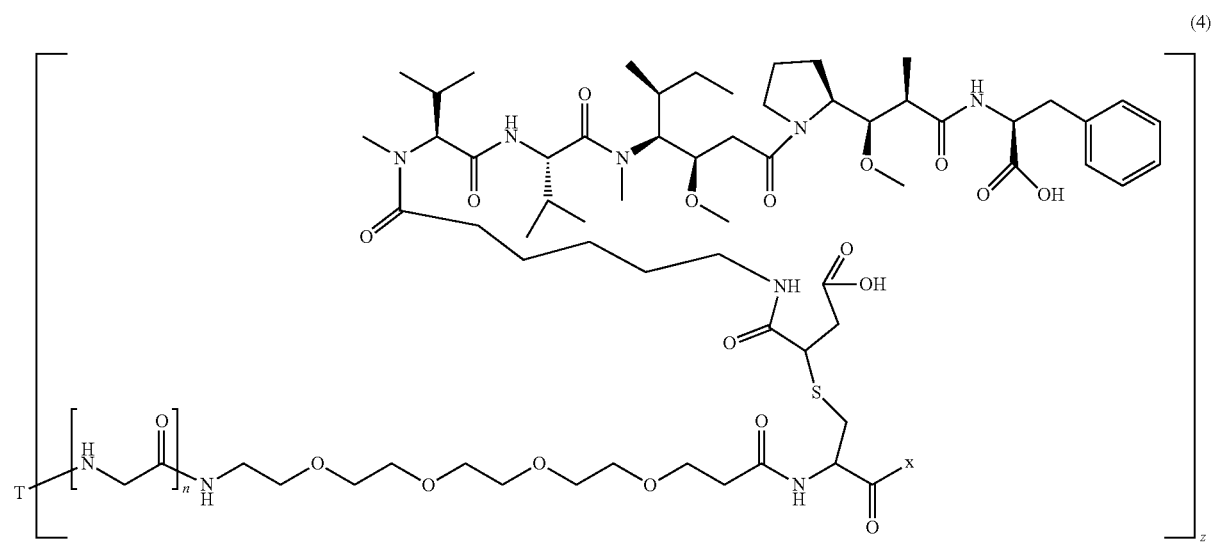
(4)

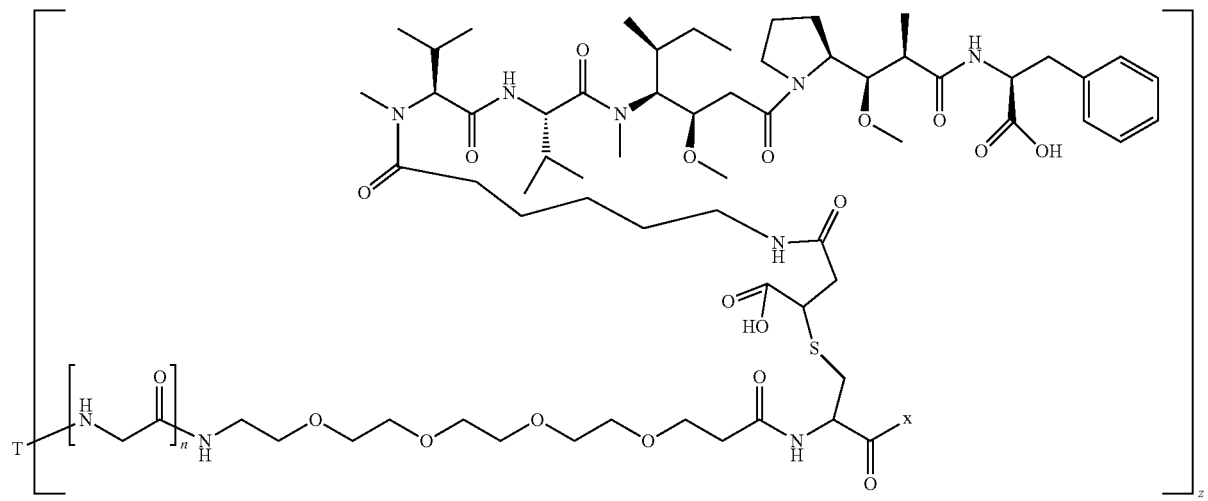
(4')

Formulae (4) and (4') are isomers, wherein:

T, n, x and z are as defined in formula (1), respectively.

In a particular embodiment, the targeting molecule is the antibody Pertuzumab, hrS7, or MAAA1181a.

In an embodiment, t is 1, the structure of L-P is as defined in formulae (IV-1-5) or (IV-1-5'), and the conjugate of formula (III) has the structure selected from the following formulae (5) and (5'). The conjugate of (5) or (5') may be prepared through conjugation reaction of the corresponding linker-payload intermediate of formula (IV-1-5) or (IV-1-5') with the biomolecule (T). In a specific embodiment, the conjugate of formula (III) has the structure selected from the following formulae (6) and (6'). The conjugate of (6) or (6') may be prepared through conjugation reaction of the corresponding linker-payload intermediate of formula (IV-1-6) or (IV-1-6') with the biomolecule (T). Formula (6) falls in the scope of formula (5), and formula (6') falls in the scope of formula (5').

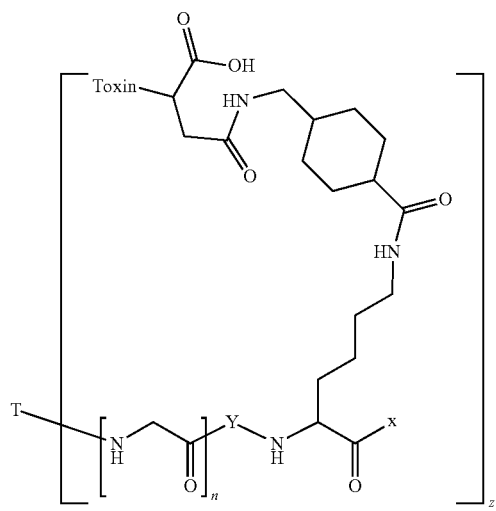
(5)

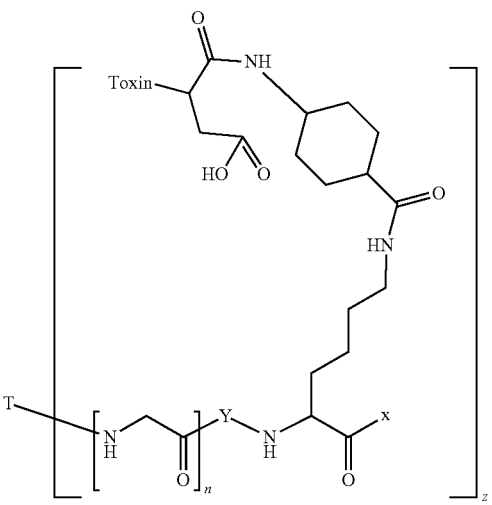
(5')

In a specific embodiment, Y does not exist. The structure of the conjugate is as shown in the following formula (6) and (6'):

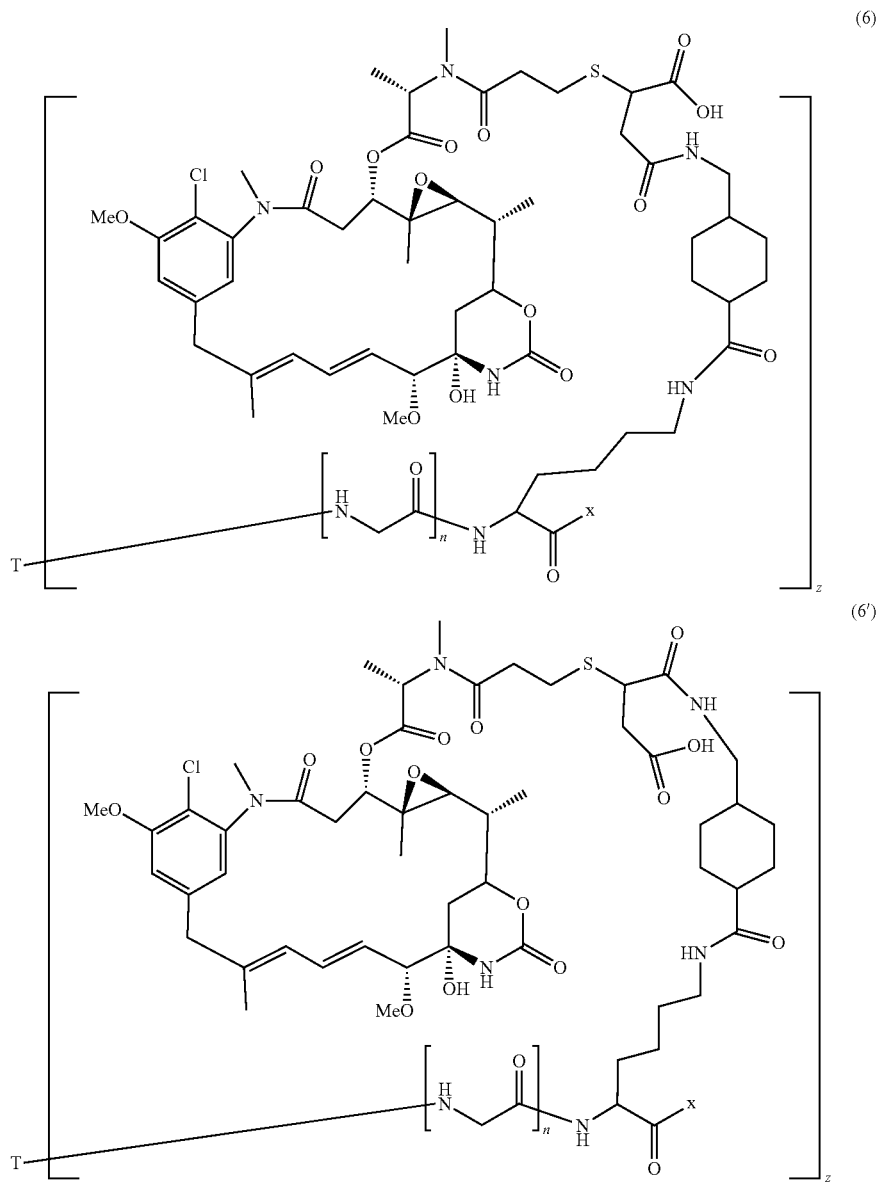

Formulae (6) and (6') are isomers. In one embodiment, T is an anti-human HER2 antibody. In another embodiment, T is a modified Trastuzumab.

Specific Embodiments for the Process

The process described herein is different from conventional chemical coupling processes in the art in that the conjugation step is catalyzed by a ligase in a site-specific manner, in which the ligase specifically recognizes the recognition motifs on the moieties to be conjugated. While in a conventional chemical coupling reaction, it is desirable to purify the moieties to be conjugated prior to the coupling reaction to avoid undesirable by-products resulted from non-specific coupling.

Therefore, in one aspect, the process according to the present disclosure obviates the need to purify the moieties to be conjugated prior to the conjugation step, thereby reducing the overall operational time and steps while increasing the final yield. Accordingly, in some embodiments, System 1 and/or System 2 in step (a) further comprise one or more impurities.

In another aspect, the process is particularly beneficial for conjugates comprising chemically labile molecules, such as biomolecules (such as proteins). In a specific aspect, the process is suitable for the preparation of a bioconjugate, wherein at least one of the first moiety and second moiety comprises a biomolecule.

Typically, processes for the manufacture of biomolecules involves cell culture methods, e.g., using either mammalian or bacterial host cell lines to produce a target protein, such as an antibody or an antibody fragment. In most cases, the harvest collection is subjected to clarification to remove cells and cellular debris, obtaining the harvested clarified cell culture fluid (HCCF), which contains impurities such as, e.g., host cell proteins (HCP), media components and nucleic acids. In a conventional chemical coupling based process, the HCCF is further subjected to a series of purification steps to obtain a high purity biomolecule for the downstream conjugation reaction. In some other cases, the harvest collection is subjected to extraction, clarification, concentration to precipitate the target protein, and the pellets are re-dissolved then subjected to purification. As the ligase in the process according to the present disclosure can specifically catalyze conjugation between the first moiety and second moiety, impurities in System 1 and/or System 2 can hardly affect the conjugation efficiency and/or specificity in step (b), a high purity of System 1 and System 2 is no longer a prerequisite for step (b). In one embodiment, at least one of System 1 and System 2 according to step (a) is a harvested clarified cell culture fluid (HCCF). The HCCF can be obtained from a tissue culture, a mammalian cell culture, a yeast cell culture, a bacterial cell culture, a bacteriophage culture, etc. In some embodiments, other samples other than HCCF can also be used.

In another preferable aspect, the process according to the present disclosure can be flexibly integrated with the production process of a biomolecule to obtain a bioconjugate comprising the same. For examples, the process can be easily integrated with the production procedure of monoclonal antibodies or antibody fragments to produce bioconjugates comprising the same. The bioconjugate can be manufactured by the same manufacturing facility, in the same product cycle of the biomolecule comprised therein, with a similar overall yield, while the original manufacturing facility and pipeline may remain largely unchanged.

In another embodiment, the process further comprises the steps of
(1) subjecting System 1 in step (a) before step (b), and/or
(2) subjecting System 2 in step (a) before step (b), and/or
(3) subjecting the conjugate obtained in step (b),
to one or more chromatography steps to remove one or more impurities.

The chromatography step can be independently selected from the group consisting of affinity chromatography, hydrophobic interaction chromatography, ion exchange chromatography, mixed mode chromatography, hydroxyapatite chromatography and a combination thereof. The ion exchange chromatography can be selected from the group consisting of anion exchange chromatography, cation exchange chromatography, mixed mode ion exchange chromatography and a combination thereof. In a preferable embodiment, the ion exchange chromatography is a combination of anion exchange chromatography and cation exchange chromatography. In some embodiments, the chromatography steps in step (3) are also referred to as polishing steps. A polishing step may comprise affinity chromatography, hydrophobic interaction chromatography, anion exchange chromatography, cation exchange chromatography, mixed mode chromatography and hydroxyapatite chromatography.

In one embodiment, at least one of the first moiety and second moiety comprises an antibody or an antibody fragment, and at least one of steps (1)-(3) comprises an affinity chromatography. The antibody can be a conventional antibody, a recombinant antibody, a multispecific antibody, a fully human antibody, a non-human antibody, a humanized antibody, a chimeric antibody, an intrabody or a nanobody. The antibody can be any type (e.g., IgG, IgM, IgD, IgE, IgA and IgY), any class (e.g. IgG1, IgG2, IgG3, IgG4, IgA1 and IgA2) or any subclass (e.g., IgG2a and IgG2b), or any derivatives thereof. The antibody fragment can be an Fv fragment, an scFv fragment, a dsFv fragment, an scdsFv fragment, an Fd fragment, an Fab fragment, an scFab fragment, an Fab' fragment, an F(ab')$_2$ fragment, an Fc fragment or a diabody. Depending on the nature of the antibody or the antibody fragment, the affinity chromatography can be Protein A affinity chromatography, Protein G affinity chromatography, Protein L affinity chromatography (such as Capto™L affinity chromatography), KappaSelect affinity chromatography, LamdaFabSelect affinity chromatography or Mabselect™ affinity chromatography. In some embodiments, at least one of the first moiety and second moiety comprises an Fc fragment, and the affinity chromatography is Protein A affinity chromatography. In some embodiments, the first moiety comprises an Fc fragment. Preferably, the Fc fragment is an Fc fragment of IgG-type antibodies, such as IgG1, IgG2, IgG3 and IgG4. In a particular embodiment, T is an antibody, and the affinity chromatography is Protein A affinity chromatography. Those of skills in the art are able to select a suitable affinity chromatography approach based on the nature of the moieties to be conjugated.

In a preferable embodiment, the chromatography steps in steps (1), (2) and (3) are selected from affinity chromatography, ion exchange chromatography, and a combination thereof.

In one embodiment, steps (1) and (2) do not exist; and step (3) is a combination of affinity chromatography and ion exchange chromatography (Process 1). In another embodiment, at least one of step (1) and step (2) comprises an affinity chromatography, and step (3) comprises an ion exchange chromatography (Process 2). In yet another embodiment, at least one of step (1) and step (2) comprises an affinity chromatography, and step (3) comprises a combination of affinity chromatography and ion exchange chromatography (Process 3). In yet another embodiment, at least one of step (1) and step (2) comprises an affinity chromatography and/or an ion exchange chromatography, and step (3) comprises a combination of affinity chromatography, hydrophobic interaction chromatography and ion exchange chromatography (Process 4).

In a particular embodiment, steps (1) and (2) do not exist; and step (3) comprises the steps in any order:
(3a-1): Protein A affinity chromatography;
(3a-2): anion exchange chromatography; and
(3a-3): cation exchange chromatography.

In another particular embodiment, at least one of steps (1) and (2) comprises a Protein A affinity chromatography, and step (3) comprises the steps in any order:
(3b-1): anion exchange chromatography; and
(3b-2): cation exchange chromatography.

In yet another particular embodiment, at least one of steps (1) and (2) comprises a Protein A affinity chromatography, and step (3) comprises the steps in any order:
(3c-1): Protein A affinity chromatography;
(3c-2): anion exchange chromatography; and
(3c-3): cation exchange chromatography.

In a particular embodiment, the first moiety and/or the second moiety comprises an Fc fragment, steps (1) and (2) do not exist, and step (3) comprises the steps in any order:
(3a-1): Protein A affinity chromatography;
(3a-2): anion exchange chromatography; and
(3a-3): cation exchange chromatography.

In another particular embodiment, the first moiety comprises an Fc fragment, step (1) comprises a Protein A affinity chromatography, and step (3) comprises the steps in any order:
(3b-1): anion exchange chromatography; and
(3b-2): cation exchange chromatography.

In yet another particular embodiment, the first moiety comprises an Fc fragment, step (1) comprises a Protein A affinity chromatography, and step (3) comprises the steps in any order:

(3c-1): Protein A affinity chromatography;
(3c-2): anion exchange chromatography; and
(3c-3): cation exchange chromatography.

In yet another particular embodiment, the second moiety comprises an Fc fragment, step (2) comprises a Protein A affinity chromatography, and step (3) comprises the steps in any order:
(3b-1): anion exchange chromatography; and
(3b-2): cation exchange chromatography.

In yet another particular embodiment, the second moiety comprises an Fc fragment, step (2) comprises a Protein A affinity chromatography, and step (3) comprises the steps in any order:
(3c-1): Protein A affinity chromatography;
(3c-2): anion exchange chromatography; and
(3c-3): cation exchange chromatography.

In yet another particular embodiment, step (1) or step (2) comprises a Protein A affinity chromatography and an anion exchange chromatography, and step (3) comprises the steps in any order:
(3d-1): Protein A affinity chromatography;
(3d-2): cation exchange chromatography; and
(3d-3): hydrophobic interaction chromatography.

In one embodiment, the affinity chromatography is performed in bind-and-elute mode. In another embodiment, the ion exchange chromatography is performed in bind-and-elute mode or flow-through mode.

In a preferable embodiment, the anion exchange chromatography is performed in flow-through mode. In one embodiment, the sample obtained in a flow-through purification process step flows continuously into the next process step. In another preferable embodiment, the cation exchange chromatography is performed in bind-and-elute mode. In one embodiment, the sample obtained in a bind-and-elute purification process step flows continuously into the next process step.

In one embodiment, step (b) is performed in batch mode, semi-continuous mode or continuous mode. In another embodiment, at least one of steps (a), (b) and (1) to (3) is performed in semi-continuous mode or continuous mode; preferably, steps (a), (b) and (1) to (3) are performed in continuous mode.

In a particular embodiment, the process of the present disclosure is performed in continuous mode; the process comprising:
(a'): providing System 1 in fluid; and providing System 2 in fluid;
(b'): subjecting System 1 and/or System 2 independently to chromatography step to obtain an eluate of System 1 and/or an eluate of System 2, wherein the eluate of System 1 and/or the eluate of System 2 has reduced level of impurities;
(c'): mixing System 1 and System 2 in step (a') or (b') to form a reaction fluid, and applying the ligase unit to the reaction fluid to catalyze the conjugation reaction of T and the linker-payload intermediate of formula (IV) and thereby obtaining a crude conjugate mixture, wherein the crude conjugate mixture comprises the target conjugate and one or more impurities;
(d'): subjecting the crude conjugate mixture of step (c') to chromatography step to remove the impurities, and obtaining the target conjugate with desired purity; wherein
steps (a') to (d') are connected to be in fluid communication with each other, such that a sample can flow continuously from one process step to the next.

The process according to the present disclosure can be adapted for the preparation of a particular conjugate, for example, by further comprising additional steps selected from the group consisting of fermentation, clarification, chromatography, pH adjustment, virus inactivation, virus filtration, ultrafiltration, diafiltration, sterile filtration, formulation and a combination thereof. Those of skills in the art will be able to combine such additional steps with the process according to the present disclosure, as well as arrange the sequential orders of the steps for the preparation of a certain conjugate.

In an embodiment, the process of the present disclosure further comprises steps of virus inactivation, virus filtration, UF/DF and/or formulation. In an embodiment, the virus inactivation is done through low-pH treatment, for example, after Protein A affinity chromatography. Virus filtration can be performed after or before the conjugation step, i.e., step (b). Preferably, virus filtration is performed after at least one chromatography step. In some embodiments, virus filtration is performed after the conjugation step, for example, after the polishing steps (for example, ADC Processes 1-3). In some other embodiments, virus filtration is performed before the conjugation step, for example, after an ion exchange chromatography (for example, ADC Process 4). In one embodiment, UF/DF is performed after the conjugation step and before step (3) (for example, ADC Processes 3-4).

In a particular embodiment, step (1) or step (2) comprises a Protein A affinity chromatography, UF/DF is performed after the conjugation step and before step (3), wherein step (3) comprises the steps in any order:
(3e-1): anion exchange chromatography; and
(3e-2): cation exchange chromatography.

In another particular embodiment, step (1) or step (2) comprises a Protein A affinity chromatography and an anion exchange chromatography, UF/DF is performed after the conjugation step and before step (3), wherein step (3) comprises cation exchange chromatography or hydrophobic interaction chromatography.

Figure 15:
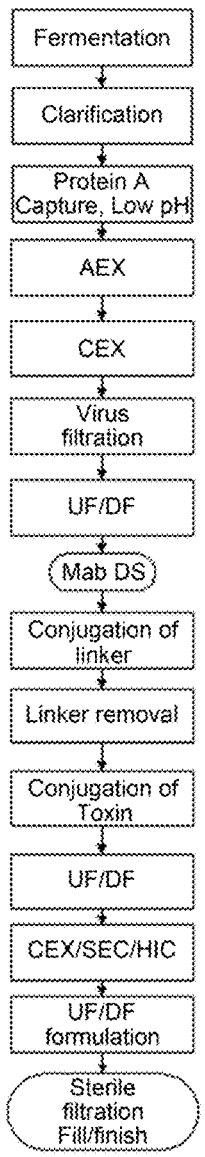
FIG. 15 shows flowcharts illustrating the steps of ADC preparation using conventional process (Conventional ADC process) and the processes according to the present disclosure (ADC Process 1, ADC Process 2, ADC Process 3 and ADC Process 4): Protein A, Protein A chromatography; low pH, low-pH treatment; UF/DF, ultrafiltration/diafiltration; AEX, anion exchange chromatography; CEX, cation exchange chromatography; HIC, hydrophobic interaction chromatography; Mab DS, monoclonal antibody downstream processes.
Figure 15:
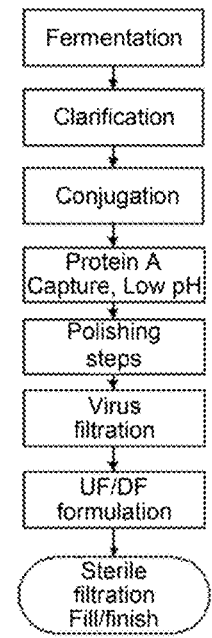
Figure 15:
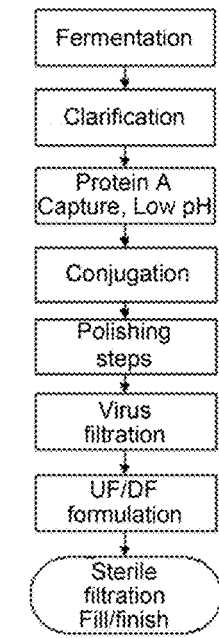
Figure 15:
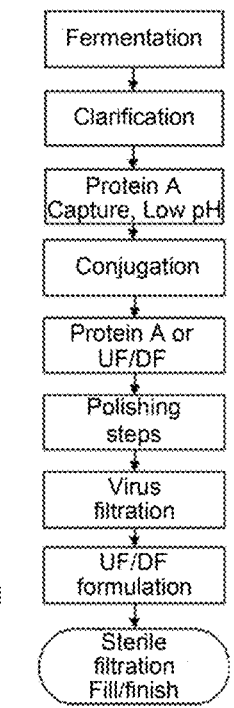
Figure 15:
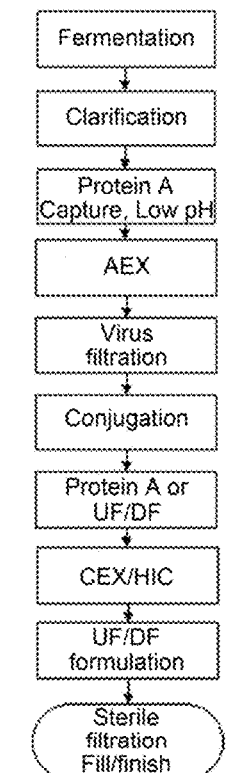

In a particular embodiment, the conjugate is an ADC, and the process is as illustrated in FIG. 15, including ADC Process 1, ADC Process 2, ADC Process 3 and ADC Process 4. Comparing to the conventional ADC process, the process according to the present disclosure involves fewer steps, thereby reducing the operational time, materials and space for the process. Furthermore, in the conventional ADC process, conjugation is typically conducted after virus filtration; while in the processes according to the present disclosure, conjugation can be performed before (Processes 1-3) or after (Process 4) virus filtration, giving more manufacturing flexibility.

In an embodiment, the disclosure provides a ligase fusion protein (the present ligase fusion protein) comprising a ligase and a Halo tag. For example, the disclosure provides
1.1. The present ligase fusion protein wherein the ligase is a transpeptidase, preferably a sortase.
1.2. The present ligase fusion protein wherein the ligase is a sortase A.
1.3. Any foregoing ligase fusion protein wherein the ligase is a sortase, preferably a sortase A; and/or the recognition motif of the ligase donor substrate is LPXTGJ; preferably LPXTG or LPETGG; and/or the recognition motif of the ligase acceptor substrate is $G_n$, wherein G is glycine (Gly), and n is an integer of 3-10; X is any natural or unnatural amino acid; J is absent, or is an amino acid fragment comprising 1-10 amino acids, wherein each amino acid is independently any natural or unnatural amino acid; preferably, J is absent or is $G_m$, wherein m is an integer of 1-10.

1.4. Any foregoing ligase fusion protein wherein the ligase is capable of catalyzing the conjugation between a first moiety comprising the recognition motif of the ligase donor substrate (e.g. comprising the terminal sequence LPXTG or LPXTGG, wherein X is any natural amino acid) and a second moiety comprising the recognition motif of the ligase acceptor substrate (e.g., comprising a terminal polyglycine sequence, e.g., GGG) to produce a conjugate of the first moiety and the second moiety.

1.5. Any foregoing ligase fusion protein wherein the ligase comprises an amino acid sequence selected from the group consisting of
   a. any of SEQ ID NOs: 1-26;
   b. any of SEQ ID NOs: 1-26 wherein the amino acid residues at positions 34, 100, 105 and 136 are optionally substituted with Ser, Asn, Ala and Thr (i.e., [Ser34][Asn100][Ala105][Thr136], SNAT), Tyr, Asn, Ala and Thr (i.e., [Tyr34][Asn100][Ala105][Thr136], YNAT), Trp, Asn, Asp and Thr (i.e., [Trp34][Asn100][Asp105][Thr136], WNDT), or Val, Asn, Asn and Ser (i.e., [Val34][Asn100][Asn105][Ser136], VNNS), respectively; for example wherein the ligase comprises the amino acid sequence of SEQ ID NO: 27 (i.e., the SNAT counterpart of SEQ ID NO: 1); and
   c. an amino acid sequence having sortase activity and a sequence identity of at least about 85%, at least about 90%, at least about 95%, or at least about 99%, to any of (a) or (b).

1.6. Any foregoing ligase fusion protein wherein the Halo tag is a polypeptide that catalyzes a removal of the halogen from a haloalkyl moiety to form a covalent bond with the dehalogenated alkyl moiety.

1.7. Any foregoing ligase fusion protein wherein the Halo tag is derived from a bacterial haloalkane dehalogenase that catalyzes a removal of the halogen from a haloalkyl moiety to form a covalent bond with the dehalogenated alkyl moiety and which is mutated to prevent hydrolysis of the covalent bond thus formed, e.g., a haloalkane dehalogenase from *Xanthobacter autotrophicus* or *Rhodococcus rhodochrous* wherein a residue involved in hydrolysis is mutated, e.g., wherein a histidine residue at a position corresponding to amino acid residue 272 of a *Rhodococcus rhodochrous* dehalogenase is mutated.

1.8. Any foregoing ligase fusion protein wherein the Halo tag comprises the amino acid sequence of SEQ ID NO: 28; or an amino acid sequence having dehalogenase activity and a sequence identity of at least about 85%, at least about 90%, at least about 95%, or at least about 99% to SEQ ID NO: 28.

1.9. Any foregoing ligase fusion protein wherein the ligase has an isoelectric point (pI) of about 7.5 to about 10.0; the Halo tag has an isoelectric point of about 4.5 to about 5.0, and the isoelectric point (pI) of the ligase fusion protein is about 2.0 to about 4.5 pH units lower than that of the ligase.

1.10. Any foregoing ligase fusion protein comprising the sequence of SEQ ID NO: 29; or an amino acid sequence having dehalogenase activity, sortase activity, and a sequence identity of at least about 85%, at least about 90%, at least about 95%, or at least about 99% to SEQ ID NO: 29.

In another embodiment, the disclosure provides an immobilized ligase (the present immobilized ligase), comprising a ligase linked via a Halo tag to a support, e.g., wherein the ligase is immobilized by the reaction of a ligase fusion protein comprising a ligase and a Halo tag, e.g., any of the present ligase fusion proteins, with a support comprising haloalkyl linkers, preferably chloroalkyl linkers, on its surface, such that the ligase fusion protein is immobilized on the support through covalent interaction between the haloalkyl linker and the Halo tag; for example, 1.1. The present immobilized ligase wherein the ligase is immobilized by the reaction of a ligase fusion protein comprising a ligase and a Halo tag with a support comprising haloalkyl linkers, wherein the ligase fusion protein is any of the present ligase fusion proteins.

1.2. Any foregoing immobilized ligase wherein the ligase is immobilized by the reaction of a ligase fusion protein comprising a ligase and a Halo tag with a support comprising a haloalkyl linker, wherein the haloalkyl linker is produced by a haloalkyl substrate having the structure of formula (I-1-1) or (I-1):

(I-1-1)

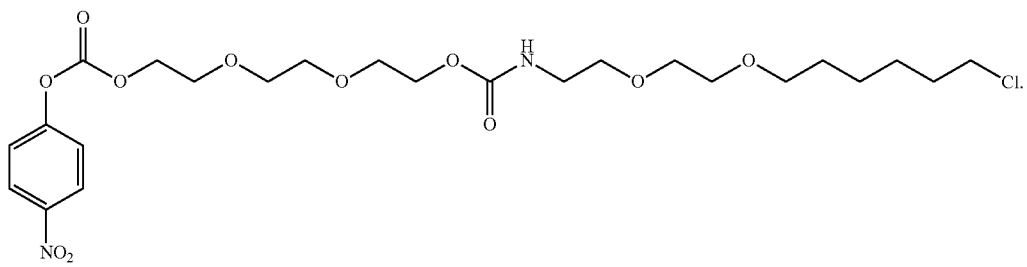

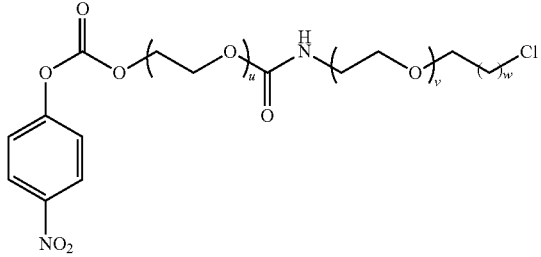

(I-1)

wherein u is an integer of 1-20, v is an integer of 0-20, and w is an integer of 1 to 19.

1.3. Any foregoing immobilized ligase, wherein the ligase is immobilized by the reaction of a ligase fusion protein comprising a ligase and a Halo tag with a support comprising a haloalkyl linker, e.g., wherein the support has the structure of formula (II-1) or (II):

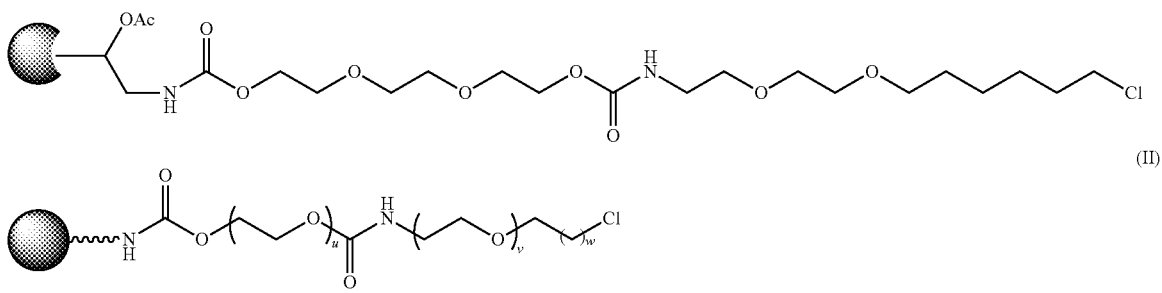

wherein the

is a support, e.g. selected from resin, a bead, a membrane, a gel, a matrix, a film, a plate, a well, a tube, a glass slide or a surface, preferably a resin, more preferable an agarose resin, a silicone resin, a polymethyl methacrylate resin or cellulose resin, most preferably a highly crosslinked agarose resin; and wherein u is an integer of 1-20, v is an integer of 0-20, and w is an integer of 1 to 19.

[Note that for the sake of clarity, only a single chloroalkyl-linker moiety is depicted attached to the support, but it is understood that there would be many such chloroalkyl-linker moieties attached to the support.]

1.4. Any foregoing immobilized ligase having the following structure:

Support-Linker-HaloTag-Ligase wherein

Support is a solid support, e.g. selected from resin, a bead, a membrane, a gel, a matrix, a film, a plate, a well, a tube, a glass slide or a surface, preferably a resin, more preferable an agarose resin, a silicone resin, a polymethyl methacrylate resin or cellulose resin, most preferably a highly crosslinked agarose resin;

Linker is a linker moiety, covalently bound to the Support, e.g., comprising a chain of 10 to 60 carbon atoms, optionally comprising one or more ether, ester, carbamate, and/or amide bonds, e.g., a linker moiety of Formula (II-1') or (II')

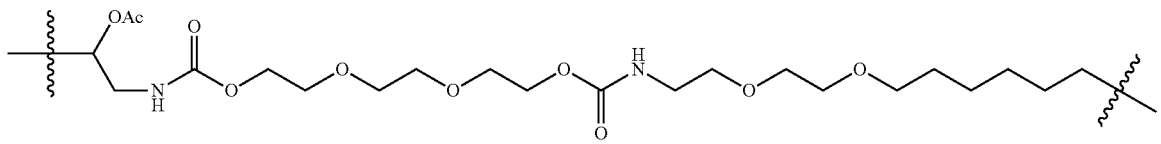

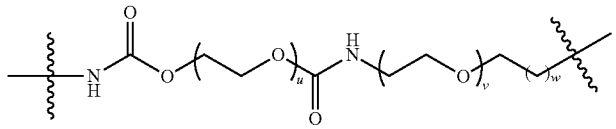

(II')

wherein u is an integer of 1-20, v is an integer of 0-20, and w is an integer of 1 to 19;
HaloTag is a Halo tag (haloalkane dehalogenase polypeptide), covalently bound to the linker;
Ligase is a ligase polypeptide;
wherein one or more "-Linker-HaloTag-Ligase" moieties are bound to the same Support.

1.5. Any foregoing immobilized ligase wherein the ligase is a sortase, preferably a sortase A; and/or the recognition motif of the ligase donor substrate is LPXTGJ; preferably LPXTG or LPETGG; and/or the recognition motif of the ligase acceptor substrate is $G_n$, wherein G is glycine (Gly), and n is an integer of 3-10; X is any natural or unnatural amino acid; J is absent, or is an amino acid fragment comprising 1-10 amino acids, wherein each amino acid is independently any natural or unnatural amino acid; preferably, J is absent or is $G_m$, wherein m is an integer of 1-10.

1.6. Any foregoing immobilized ligase wherein the ligase is capable of catalyzing the conjugation between a first moiety comprising the recognition motif of the ligase donor substrate (e.g. comprising the terminal sequence LPXTG or LPXTGG, wherein X is any natural amino acid) and a second moiety comprising the recognition motif of the ligase acceptor substrate (e.g., comprising a terminal polyglycine sequence, e.g., GGG) to produce a conjugate of the first moiety and the second moiety.

1.7. Any foregoing immobilized ligase wherein the ligase comprises an amino acid sequence selected from the group consisting of
 a. any of SEQ ID NOs: 1-26;
 b. any of SEQ ID NOs: 1-26 wherein the amino acid residues at positions 34, 100, 105 and 136 are optionally substituted with Ser, Asn, Ala and Thr (i.e., [Ser34][Asn100][Ala105][Thr136], SNAT), Tyr, Asn, Ala and Thr (i.e., [Tyr34][Asn100][Ala105][Thr136], YNAT), Trp, Asn, Asp and Thr (i.e., [Trp34][Asn100][Asp105][Thr136], WNDT), or Val, Asn, Asn and Ser (i.e., [Val34][Asn100][Asn105][Ser136], VNNS), respectively; for example wherein the ligase comprises the amino acid sequence of SEQ ID NO: 27 (i.e., the SNAT counterpart of SEQ ID NO: 1); and
 c. an amino acid sequence having sortase activity and a sequence identity of at least about 85%, at least about 90%, at least about 95%, or at least about 99%, to any of (a) or (b).

1.8. Any foregoing immobilized ligase wherein the Halo tag is a polypeptide that catalyzes a removal of the halogen from a haloalkyl moiety to form a covalent bond with the dehalogenated alkyl moiety.

1.9. Any foregoing immobilized ligase wherein the Halo tag is derived from a bacterial haloalkane dehalogenase that catalyzes a removal of the halogen from a haloalkyl moiety to form a covalent bond with the dehalogenated alkyl moiety and which is mutated to prevent hydrolysis of the covalent bond thus formed, e.g., a haloalkane dehalogenase from *Xanthobacter* or *Rhodococcus* wherein a residue involved in hydrolysis is mutated, e.g., wherein a histidine residue at a position corresponding to amino acid residue 272 of a *Rhodococcus* dehalogenase is mutated.

1.10. Any foregoing immobilized ligase wherein the Halo tag comprises the amino acid sequence of SEQ ID NO: 28; or an amino acid sequence having dehalogenase activity and a sequence identity of at least about 85%, at least about 90%, at least about 95%, or at least about 99% to SEQ ID NO: 28.

1.11. Any foregoing immobilized ligase wherein the ligase has an isoelectric point (pI) of about 7.5 to about 10.0; the Halo tag has an isoelectric point of about 4.5 to about 5.0, and the isoelectric point (pI) of the ligase fusion protein is about 2.0 to about 4.5 pH units lower than that of the ligase.

1.12. Any foregoing immobilized ligase comprising the sequence of SEQ ID NO: 29; or an amino acid sequence having dehalogenase activity, sortase activity, and a sequence identity of at least about 85%, at least about 90%, at least about 95%, or at least about 99% to SEQ ID NO: 29.

1.13. Any foregoing immobilized ligase comprising the sequence of SEQ ID NO: 29; or an amino acid sequence having dehalogenase activity, sortase activity, and a sequence identity of at least about 85%, at least about 90%, at least about 95%, or at least about 99% to SEQ ID NO: 29, bound via a linker to a support.

In another embodiment, the disclosure provides a process (the present process) for the preparation of a conjugate comprising a first moiety and a second moiety, e.g., a drug-antibody conjugate, wherein one of the first moiety and the second moiety comprises a recognition motif of the ligase donor substrate, and the other one of the first moiety and the second moiety comprises the recognition motif of the ligase acceptor substrate, the process comprising contacting the first moiety with the second moiety in the presence of a ligase unit which is an immobilized ligase or a ligase fusion protein comprising a ligase and a Halo tag; for example, 1.1. The present process wherein the ligase unit is an immobilized ligase comprising a ligase linked via a Halo tag to a support, e.g., wherein the immobilized ligase is any of the present immobilized ligases.

1.2. The present process wherein the ligase unit is any of the present ligase fusion proteins.

1.3. Any foregoing process comprising the steps of:
 (a) providing System 1 comprising the first moiety and providing System 2 comprising the second moiety; and
 (b) contacting the ligase unit with System 1 and System 2 in step (a) to catalyze the conjugation reaction between the first moiety and the second moiety to obtain the conjugate;
 wherein the first moiety and the second moiety each independently comprises a biomolecule, a protein, an antibody, an antibody fragment, a receptor, a signal transduction factor, a cell growth factor, a nucleic acid or a nucleic acid analogue, a small molecule compound, a glycan, a PEG moiety, a radionuclide, a cytokine, an immunomodulator, a tracer molecule, a fluorophore, a fluorescent molecule, a peptide, a polypeptide, or a peptidomimetic; and wherein one of the first moiety and the second moiety further comprises the recognition motif of the ligase donor substrate, and the other one of the first moiety and the second moiety comprises the recognition motif of the ligase acceptor substrate, such that the ligase unit will catalyze conjugation between the recognition motif of the ligase donor substrate and the recognition motif of the ligase acceptor substrate;

for example, wherein step (b) is performed in batch mode, semi-continuous mode or continuous mode.

1.4. The foregoing process further comprising the steps of
(1) subjecting System 1 in step (a) before step (b), and/or
(2) subjecting System 2 in step (a) before step (b), and/or
(3) subjecting the conjugate obtained in step (b),
to one or more chromatography steps to remove one or more impurities;
for example, wherein the chromatography step is independently selected from affinity chromatography, hydrophobic interaction chromatography, ion exchange chromatography, and a combination thereof; wherein the ion exchange chromatography is selected from anion exchange chromatography, cation exchange chromatography, and a combination thereof;
preferably, the chromatography step is selected from affinity chromatography, ion exchange chromatography, and a combination thereof;
for example, wherein at least one of steps (a), (b) and (1)-(3) is performed in semi-continuous mode or continuous mode; e.g., wherein, steps (a), (b) and (1)-(3) are performed in continuous mode;
for example, wherein at least one of the first moiety and the second moiety comprises an antibody or an antibody fragment, and at least one of steps (1)-(3) comprises an affinity chromatography; e.g., wherein the antibody or antibody fragment comprises an Fc fragment, and the affinity chromatography is Protein A affinity chromatography;
for example, wherein the first moiety or the second moiety comprises an Fc fragment,
steps (1) and (2) do not exist, and step (3) comprises the steps in any order:
(3a-1): Protein A affinity chromatography;
(3a-2): anion exchange chromatography; and
(3a-3): cation exchange chromatography; or
step (1) or step (2) comprises a Protein A affinity chromatography, and step (3) comprises the steps in any order:
(3b-1): anion exchange chromatography; and
(3b-2): cation exchange chromatography; or
step (1) or step (2) comprises a Protein A affinity chromatography, and step (3) comprises the steps in any order:
(3c-1): Protein A affinity chromatography;
(3c-2): anion exchange chromatography; and
(3c-3): cation exchange chromatography; or
step (1) or step (2) comprises a Protein A affinity chromatography and an anion exchange chromatography, and step (3) comprises the steps in any order:
(3d-1): Protein A affinity chromatography;
(3d-2): cation exchange chromatography; and
(3d-3): hydrophobic interaction chromatography;

for example, wherein the affinity chromatography is performed in bind-and-elute mode; and/or the ion exchange chromatography is performed in bind-and-elute mode or flow-through mode; e.g., wherein, the anion exchange chromatography is performed in flow-through mode; and/or the cation exchange chromatography is performed in bind-and-elute mode.

1.5. Any foregoing process wherein one or more impurities are present in the reaction between the first moiety and the second moiety.

1.6. Any foregoing process wherein the first moiety or the second moiety is comprised in a harvested clarified cell culture fluid (HCCF).

1.7. Any foregoing process wherein the ligase unit is a ligase fusion protein comprising a ligase and a Halo tag, further comprising the step of reacting the ligase unit with a support comprising haloalkyl linkers and, after the reaction between the first moiety and the second moiety is substantially completed, removing the immobilized ligase, e.g., any of the present immobilized ligases, thus formed.

1.8. Any foregoing process wherein the ligase unit is an immobilized ligase, e.g., any of the present immobilized ligases, further comprising removing the immobilized ligase after the reaction between the first moiety and the second moiety is substantially completed.

1.9. Any foregoing process wherein the conjugate has the structure of formula (III), the first moiety comprises T, and the second moiety comprises a linker-payload intermediate of formula (IV):

$$T \; + \; (L-P_t)_z \; \xrightarrow{\text{ligase unit}} \; T-(L-P_t)_z$$
$$(IV) \hspace{4em} (III)$$

wherein
T comprises a biomolecule, which is optionally modified to have one of the recognition motif of the ligase donor substrate and the recognition motif of the ligase acceptor substrate;
L comprises a linker, which comprises the other of the recognition motif of the ligase donor substrate and the recognition motif of the ligase acceptor substrate;
P comprises a payload;
z is an integer of 1-20;
t is an integer of 1-20.

1.10. The foregoing process, wherein
T comprises a protein, a peptide, an antibody, an antibody fragment, a receptor, a signal transduction factor, a cell growth factor and a nucleic acid or analogue; and/or P comprises hydrogen, a small molecule compound, preferably a toxin, a glycan, a PEG moiety, a radionuclide, a cytokine, an immunomodulator, a nucleic acid or analogue, a tracer molecule, a fluorophore, a fluorescent molecule, a peptide, a polypeptide, a peptidomimetic, an antibody, an antibody fragment, or a protein.

1.11. Any foregoing process wherein the ligase is a sortase, preferably a sortase A; and/or the recognition motif of the ligase donor substrate is LPXTGJ; preferably LPXTG or LPETGG; and/or the recognition motif of the ligase acceptor substrate is $G_n$, wherein
G is glycine (Gly), and n is an integer of 3-10;
X is any natural or unnatural amino acid;

J is absent, or is an amino acid fragment comprising 1-10 amino acids, wherein each amino acid is independently any natural or unnatural amino acid; preferably, J is absent or is $G_m$, wherein m is an integer of 1-10.

Beneficial Effects

In an aspect, the present disclosure provides a ligase fusion protein having at least one of the following advantageous features:

(1) the ligase fusion protein is highly expressible and soluble, thereby lowing the cost for enzyme purification;

(2) the ligase fusion protein can be easily purified with a high purity and activity in large amount, therefore is particularly suitable for industrial applications; and (3) the ligase fusion protein can be easily immobilized at a physiological condition, which not only benefits the storage and shipping of the ligase but also helps in preserving the maximum enzymatic activity and improving the manufacturing scalability.

In another aspect, provided is an immobilized ligase comprising the ligase fusion protein. The immobilized ligase has at least one of the following advantageous features:

(1) high stability;

(2) high reusability, the immobilized ligase can easily be retrieved and separated from the reaction system after the reaction completes, while the enzymatic activity is substantially uncompromised;

(3) good alkali resistance, making alkali-based cleansing of the immobilized ligase possible; and (4) high enzyme capacity and high enzymatic activity, therefore, the immobilized ligase can catalyze conjugation reactions with highly concentrated enzyme activity in a confined space, thereby saving working and storage space and cost of regents comparing to the free ligase.

Therefore, the immobilized ligase according to the present disclosure is controllable, reusable, cost-efficient and easy to scale up, and thus is particularly advantageous for industrial applications.

In a particular aspect, the ligase fusion protein has an altered isoelectric point compared to the ligase from which the ligase fusion protein is derived, allowing effective removal of carryover enzyme contaminants from the final conjugate products. This feature is especially important for conjugates that do not comprise affinity moieties for efficient affinity purification. For example, for a conjugate with a pI of about 8 to about 9, a ligase fusion protein with a pI of about 5 to about 6 can be used, and the conjugate and the ligase fusion protein can be separated with anion exchange chromatography, in which the ligase fusion protein binds to the chromatography media while the conjugate flows through, or with a cation exchange chromatography, in which the conjugate binds to the chromatography media while the ligase fusion protein flows through. More importantly, owing to the altered pI of the ligase fusion protein, possible trace amounts of free enzymes (e.g., those non-specifically adsorbed on the support may fall off during catalysis) can be easily removed.

In another aspect, the present disclosure provides a process for preparing a conjugate using the ligase fusion protein or the immobilized ligase according to the present disclosure.

Conventional processes for the preparation of conjugates containing protein moieties include at least two sets of purification processes: the upstream and downstream purification of the protein before the conjugation step, and the downstream purification of the conjugation product after the conjugation step, each including several chromatography steps. For the preparation of ADC (antibody-drug conjugate), the current mainstream conjugation technology is chemistry based, wherein the drug is chemically conjugated to lysine or cysteine residue in the antibody via a linker. Before the conjugation step, antibodies with a high purity is prepared through upstream and downstream processes, since antibody with a lower purity would result in unpredictable outcomes, such as by-products resulting from the coupling of the payload and the lysine/cysteine in the impurities in the antibody feed. Impurities in the antibody feed decrease the conjugation step yield, and thereby put pressure on the process productivity, causing requirements to increase the input, which in turn aggravates the complexity of the whole process. After the conjugation step, another downstream purification process is required to remove the aggregates, solvents, by-products and impurities from ADC. The dual downstream steps in the conventional process significantly increase cost and time, and simultaneously lower the yield. Moreover, the conjugation reaction has to be conducted in chemical isolators for safety reasons, making the process difficult to scale up. Overall, the conventional processes involve multiple upstream and downstream purification steps, which are time-consuming, uneconomic, inflexible and lack of scalability.

The process of the present disclosure achieves at least one of the following technical effects:

(1) owing to the substrate specificity of the ligase, the process can be carried out without a prior purification procedure of the moieties to be conjugated from raw materials, thereby leading to reduced overall operational time and steps, reduced cost (e.g., pure water or water for injection, reagents for various buffers, chromatography media and the like), and improved yield;

(2) the process can be flexibly integrated with the procedures of the biomolecule moieties like antibodies to be conjugated, that is, the target conjugate can be manufactured by the same manufacturing facility, in the same product cycle of the biomolecule moieties comprised therein, with a similar overall yield, while the original manufacturing facility and pipeline may remain largely unchanged;

(3) the process can be easily scaled up to meet industrial needs, especially when an immobilized ligase is used;

(4) simplified in-process product quality analysis is achieved;

(5) efficient removal of impurities such as excess reaction material, and residual enzyme contaminants carried over from the upstream catalytic reaction is realized; and (6) improved space-time economy is achieved, etc.

In addition to the above advantages, the process of the present disclosure is particularly advantageous for the preparation of a bioconjugate over the conventional process at least in the following aspects:

(1) formation of aggregates (such as antibody and ADC aggregates) is minimum, thereby increasing the final yield while lessening the workload for aggregate removal; and (2) the DAR ratio and conjugation site on the bioconjugate can be easily manipulated, thereby producing bioconjugates with a higher homogeneity and well-defined physicochemical characteristics.

EXAMPLES

In order to illustrate the objects and technical solutions more clearly, the present disclosure is further described below with reference to specific examples. It is to be understood that the examples are not intended to limit the scope of the disclosure. The specific experimental methods which are not mentioned in the following examples are carried out according to conventional experimental methods.

Instruments, Materials and Reagents

Unless otherwise stated, the instruments and reagents are commercially available or can be prepared according to conventional means in the art.

MabSelect Sure ProA is obtained from GE; Q Sepharose FF/Capto S impact are obtained from GE. CHO cells for antibody expression are obtained from Thermo fisher Scientific. pcDNA3.3 are obtained from Life Technology.

HIC-HPLC: Butyl-HIC; mobile phase A: 25 mM PB, 2M $(NH_4)_2SO_4$, pH 7.0; mobile phase B: 25 mM PB, pH 7.0; flow rate: 0.8 ml/min; acquisition time: 25 mM; injection amount: 20 µg; column temperature: 25° C.; detection wavelength: 280 nm; sample chamber temperature: 8° C.

General Procedures

General Procedures for Antibody Production

The processes for antibody preparation can be found in e.g. US20170112944A1, which are fully incorporated by reference in its entirety. Briefly, a plasmid construct encoding the anti-human HER2 antibody Trastuzumab is transfected into CHO cells, wherein the antibody is modified at the C-terminus of the light chain by comprising a donor recognition motif LPETGG to obtain the antibody T-LCCT$_L$-HC. Transfected CHO cells are screened for a highly expressed cell population, which is cultured with reference to the culture process of Trastuzumab in a 5-10 L reactor. The cell culture is centrifuged to obtain a harvested clarified cell culture fluid (HCCF).

The HCCF can be used as the antibody feed for conjugation reaction (Process 1) or further subjected to downstream processing to provide a purified antibody for conjugation reaction (Processes 2 and 3).

General Procedures for Antibody Purification

The processes for antibody purification can be found in e.g. US20170112944A1, which are fully incorporated by reference in its entirety. Briefly, the purification of T-LCCT$_L$-HC is carried out in a standard process using the combination of Protein A affinity chromatography (MabSelect Sure ProA) and Sepharose S cation exchange chromatography, the purified products are dissolved in the original Trastuzumab drug buffer (5 mM histidine-HCl, 2% Trehalose, 0.009% Polysorbate 20, pH 6.0).

General Procedures for the Linker-Payload Intermediate Preparation

The processes for the production of linker-payload intermediate can be found in e.g. US20170112944A1, which are fully incorporated by reference in its entirety. Briefly, the procedures are:

A solution of the linker having the structure of formula (V-1-2) is incubated with a solution of the payload to form a linker-payload intermediate having the formula of (IV-1-5-1), which is further subjected to ring-open reaction to obtain a ring-open linker-payload intermediate having the structure of formula (IV-1-5) or (IV-1-5'). In the Examples, the payload is DM1, and the linker-payload intermediate has the structure of formula (IV-1-6) or (IV-1-6'). The ring-open linker-payload intermediate is purified and analyzed by HPLC.

General Procedures for the Conjugation Reaction

The processes for the production of ADCs using antibodies purified from Protein A affinity chromatography can be found in e.g. US20170112944A1, which are fully incorporated by reference in its entirety. Briefly, the procedures are:

Prepare buffers containing the antibody T-LCCT$_L$-HC (1-100 mg/ml) and the linker-payload intermediate (0.1-50 mg/ml) having the structure of formula (IV-1-6) or (IV-1-6') separately as described above.

Fill the immobilized Halo-Sortase in a container in a desired amount. Treat the immobilized Halo-Sortase with 20 mM Tris-HCl, 1-3 M NaCl (pH 6.0-10.0), 0.1-1.0 M NaOH. Pre-warm the immobilized Halo-Sortase at 10-40° C. for about 30 min or above in an air bath or a water bath. Mix the antibody solution and the linker-payload intermediate solution according to the established ratio (antibody:linker-payload intermediate=1:1-1:100) to obtain a mixture, and then add the mixture to a container containing the treated immobilized Halo-Sortase (pull-down mode) or to the Halo-Sortase column (flow-through mode). Start the conjugation reaction. The reaction time is 5 minutes to 24 hours.

After the conjugation reaction is completed, collect the reaction solution or the flow-through from the immobilized Halo-Sortase column to obtain a crude conjugate mixture comprising the target conjugate, which has the structure of formula (6) or (6'). Subject the crude conjugate mixture to HIC-HPLC for analysis of DAR of the ADC to determine the conjugation efficiency of the reaction.

General Procedures for the Protein a Affinity Chromatography

Equilibrate the column with 20 mM Tris, 150 mM NaCl, pH 7.5, and load the crude conjugate mixture. Continue to flush with 20 mM Tris, 150 mM NaCl, pH 7.5, until the desired offset (baseline) is reached. Optionally, wash the impurities with citric acid-sodium citrate buffer, pH 5.0 (Wash step). Elute the desired ADC with citric acid-sodium citrate buffer, pH 3.3-3.7. Collect the eluate containing the desired ADC. Adjust the pH of the eluate to pH 5.0-6.0 using 1 M Tris-HCl, pH 9.0. Analyze the eluate for residual impurities, such as HCP, DNA, and Protein A, using ELISA analysis or qPCR.

General Procedures for the Anion Exchange Chromatography

Pack the column with Q Sepharose FF medium. Equilibrate the column with 20-100 mM Tris-HCl pH 6.5-8.0, and load the combined eluate collected from the Protein A affinity chromatography. Collect the flow-through containing the target ADCs. Continue to flush with 20 mM Tris-HCl pH 6.5-8.0, until the desired offset (baseline) is reached. Regenerate the column with 20-100 mM Tris-HCl, 1 M NaCl pH 6.5-8.0. Conduct clean-in-position (CIP) for 30 min using 1 M NaOH. Analyze the eluate for residual impurities, such as HCP, DNA, and Protein A.

General Procedures for the Cation Exchange Chromatography

Pack the column with Capto S ImpAct medium. Equilibrate the column with citric acid-sodium citrate buffer, pH 5.0-6.0, and load the eluate from the Protein A affinity chromatography. Continue to flush with citric acid-sodium citrate buffer, pH 5.0-6.0, until the desired offset (baseline) is reached. Elute the target ADCs with citrate-sodium citrate buffer, 100-500 mM NaCl, pH 5.0-6.0. Collect the eluate containing the target ADC. Regenerate the column with citrate-sodium citrate buffer, 1 M NaCl, pH 6.0. Conduct clean-in-position (CIP) for 30 min using 1 M NaOH. Analyze the eluate for residual impurities, such as HCP, DNA, and Protein A.

Example 1: Preparation of the Ligase Fusion Protein

1.1 Cloning and Purification of SrtAs

Nucleic acids encoding the SrtA having an amino acid sequence selected from SEQ ID NO: 1-26 and their variants ([Ser34][Asn100][Ala105][Thr136], SNAT; [Tyr34][Asn100] [Ala105][Thr136], YNAT; [Trp34][Asn100][Asp105][Thr136]; WNDT [Val34][Asn100] [Asn105][Ser136], VNNS) were synthesized by gene synthesis standard method and sub-cloned into the expression vector pET-21a(+) at NdeI and EcoRI by Gibson Assembly. And a $HiS_6$ tag was inserted at the N-terminal of the SrtA open reading frame.

SrtA expression plasmids were transformed into *E. coli* BL21(DE3). Until OD600=0.5-0.8 after culturing at 37° C. in LB with 50 μg/ml Ampicillin, IPTG was added to a final concentration of 0.2 mM and sortase expression was induced at 25° C. for 12 hours. The target cells were harvested by centrifugation and re-suspended in lysis buffer (50 mM Tris pH 8.0, 300 mM NaCl) and then lysed by sonication and the supernatant was purified on Ni-NTA agarose following the manufacturer's instructions. The purity as judged by SDS-PAGE of the sortases were >90%. SrtAs' concentration were calculated from the measured A280 using the extinction coefficient method.

1.2 Evaluation of Sortase Activities

Recombinant SrtAs as prepared in Example 1.1 were subjected to a fluorometric assay to measure their sortase activities. Reactions (total volume 100 μL, 0.085 mM Abz-LPETGK-Dnp, 18 mM tri-glycine in buffer A (buffer A: 5 mM $CaCl_2$, 150 mM NaCl, 50 mM Tris-HCl, pH 7.5) in 96-well plate were initiated at 37° C. by adding 0.625 μM purified SrtAs or variants. Abz-LPETGK-Dnp is an internally quenched peptide with 2-aminobenzimidazole (Abz) as the fluorophore and 2, 4-dinitrophenyl (Dnp) as the quencher. Upon cleavage of the peptide LPETGK by sortase, Dnp and Abz are separated and the fluorescent signal from Abz can be detected to indicate the sortase activity. The increase in fluorescence signal was continuously collected after 1 hr ($\lambda_{exe}/\lambda_{em}$=320 nm/420 nm, Gain=85, Biotek Cytation3 plate reader).

Activities of exemplary SrtAs, SrtA derived from *Staphylococcus warneri* (SEQ ID NO: 3) and its variant ([Ser34][Asn100][Ala105][Thr136], SNAT), are shown in bar graphs (FIG. 1). The result shows that the SNAT variant SrtA has about 1-fold higher activity than its wild type SrtA (SEQ ID NO: 3), while both of them have sortase activity.

1.3 Cloning of the Ligase Fusion Protein According to the Present Disclosure (Halo-Sortase)

Nucleic acids encoding the ligase fusion proteins according to the present disclosure, each comprises a SrtA having an amino acid sequence selected from SEQ ID NO: 1-26 and their variants ([Ser34][Asn100][Ala105] [Thr136], SNAT; [Tyr34][Asn100][Ala105][Thr136], YNAT; [Trp34][Asn100][Asp105][Thr136]; WNDT [Val34][Asn100][Asn105][Ser136], VNNS) and a Halo tag having the amino acid sequence of SEQ ID NO: 28 (Halo-Sortase), were cloned into a bacterial expression vector pET21a or pET24d. A Halo-Sortase having the amino acid sequence of SEQ ID NO: 29, which comprises a SrtA variant derived from *Staphylococcus aureus* (SEQ ID NO: 27) and a Halo tag (SEQ ID NO: 28), is used in the following examples.

1.4 Purification of Halo-Sortase

Halo-Sortase is expressed in *E. coli* BL21(DE3), purified and stored in 5%-10% glycerol at −80° C. His-Sortase with a $His_6$ tag and GB1-Sortase with a GB1 tag are prepared in a similar manner for comparison purposes.

1.5 Activity of Halo-Sortase

Procedures:

(1) Mix the purified antibody T-LCCT$_L$-HC with the linker-payload intermediate having the structure of formula (IV-1-6) or (IV-1-6') at an optimal molar ratio (Ab:linker-payload intermediate=1:1-1:100) in the conjugation buffer.

(2) Incubate Halo-Sortase, His-Sortase or GB1-Sortase prepared as in Example 1.4 with the mixture from step (1) at 4-40° C. for 0.5-20 h, respectively.

(3) Store the product from step (2) at 4° C. or −80° C.

(4) Subject the product to 12% SDS-PAGE electrophoresis to determine the conjugation efficiency.

Figure 2:
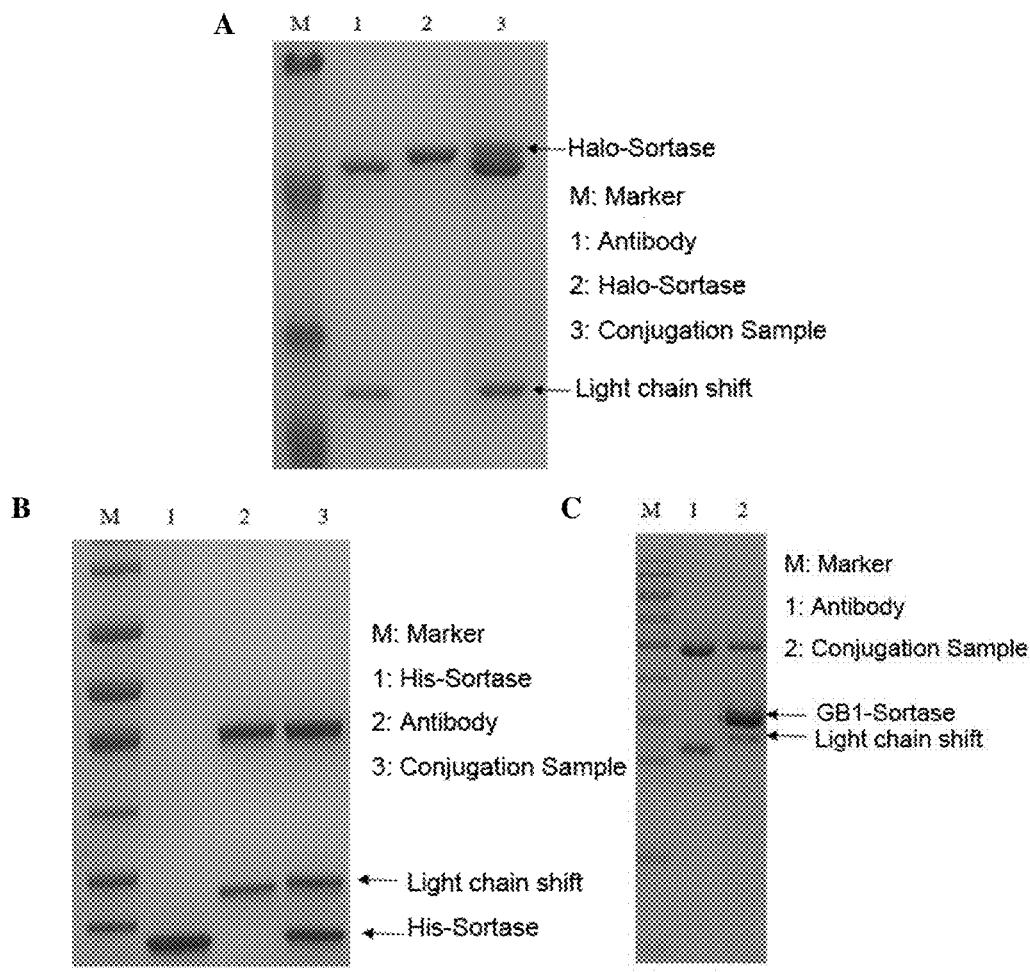
FIG. 2 depicts the activities of purified (A) Halo-Sortase, (B) His$_6$-Sortase and (C) GB1-Sortase.

The result is shown in FIG. 2, the conjugation efficiencies of Halo-Sortase, GB1-Sortase and His-Sortase are over 90%.

Example 2: Preparation of Immobilized Halo-Sortase

2.1 Preparation of the Chloroalkyl-Linker Modified Resin (Chloro Resin)

Methods of preparing Chloro Resin have been described in, for example, in U.S. Pat. Nos. 7,429,472, 7,888,086 and 8,202,700, which are incorporated by reference herein in their entirety. Resins used for Chloro Resin preparation are shown in Table 2.

TABLE 2

| | Resin | Code |
|---|---|---|
| 1 | NHS-activated Bestaresin 4FF (Highly crosslinked agarose, Bestchrom) | HX17091 |
| 2 | CNBr-activated Bestaresin (Highly crosslinked agarose, Bestchrom) | HX17092 |
| 3 | Epoxy-activated resin (Polymethyl methacrylate, Nano-Micro) | HX17093 |
| 4 | Epoxy-activated Bestaresin 4FF (Highly crosslinked agarose, Bestchrom) | HX17094 |

Procedures:

(1) Pre-Treatment

For NHS-activated resin (Bestchrom) and CNBr-activated resin (Bestchrom):

Filter resin in isopropyl alcohol and wash the filter cake once with DMF, and dry by suctioning. Transfer the filter cake to a flask using DMF and stir. Subsequently, add ethylenediamine to the mixture, and stir for 10 to 15 h. Filter and wash the filter cake with DMF. Then drain the liquid.

For epoxy-activated resins:

Filter resin in isopropyl alcohol and wash the filter cake once with $H_2O$, and dry by suctioning. Transfer the filter cake to a flask and stir. Subsequently, add 25% to 28% concentrated ammonia water to the mixture, slowly heat the system to 40-50° C. and react at 40-50° C. with stirring. Lower the temperature of the system to 20-30° C., and filter the mixture. Wash the filter cake with $H_2O$ until the filtrate pH reaches about 7-8. Subsequently, wash the filter cake with DMF and drain the liquid.

(2) Transfer the filter cake from the step (1) to a flask and stir. Sequentially add DMF containing chloroalkyl substrate having the structure of formula (I-1-1) as described above and triethylamine to the system. React with stirring. Subsequently, filter the system and wash the filter cake with DMF and finally drain the liquid.

(3) Transfer the filter cake from step (2) to a flask. Turn on the stirring. Sequentially add Ac2O and triethylamine to the mixture. React with stirring. Then, filter the mixture and wash the filter cake with DMF. Then wash the filter cake with $H_2O$ and drain the liquid. Finally, transfer the mixture to a container using 20% ethanol for storage.

Results: the Chloro Resin having the structure of formula (II-1) is obtained:

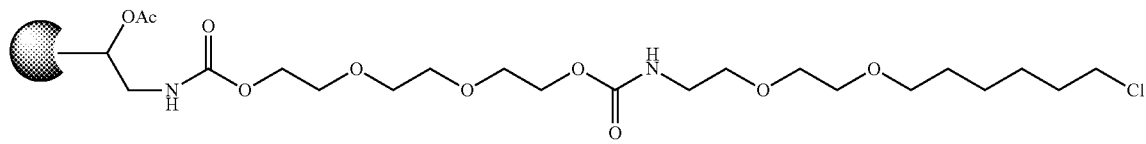

(II-1)

wherein the

is highly crosslinked agarose resin or polymethyl methacrylate resin.

2.2 Immobilization of Halo-Sortase to the Chloro Resin
Procedures:
(1) Incubate the purified Halo-Sortase prepared as in Example 1.4 and the Chloro resin prepared as in Example 2.1 at room temperature for 10 min-24 h;
(2) Wash the resin with 20 mM Tris-HCl, 150 mM NaCl (pH 6.0-10.0) for three times; (3) Determine the enzymatic activity of the immobilized Halo-Sortase;
(4) Optionally, pack the column with the immobilized Halo-Sortase to obtain a Halo-Sortase column;
(5) Wash the immobilized Halo-Sortase from step (3) or the Halo-Sortase column from step (4) with 20 mM Tris-HCl, 1-3 M NaCl (pH 6.0-10.0), 0.1-1.0 M NaOH and store at 4° C.

Example 3: Characterization of the Chloro Resin

Procedures:
(1) Take 250 μl of each Chloro Resin to be tested, add in an excessive amount of Halo-Sortase, place the tubes on a rotor, and incubate for 2 h at room temperature;
(2) At different time points (15 mM, 30 mM, 1 h and 2 h, respectively) of the immobilization reaction, take a drop of supernatant of each Chloro Resin by centrifuging the tube at 3000 g for 3 mM at room temperature, and determine the concentration of Halo-Sortase in the supernatant using a Nanodrop spectrophotometer;
(3) Calculate the concentration of Halo-Sortase at each time point, which is then subtracted from the initial concentration of Halo-Sortase to obtain the amount of immobilized Halo-Sortase at each time point, and plot a curve showing the amount of Halo-Sortase immobilized on the Chloro Resin as a function of the conjugation time.

Figure 3:
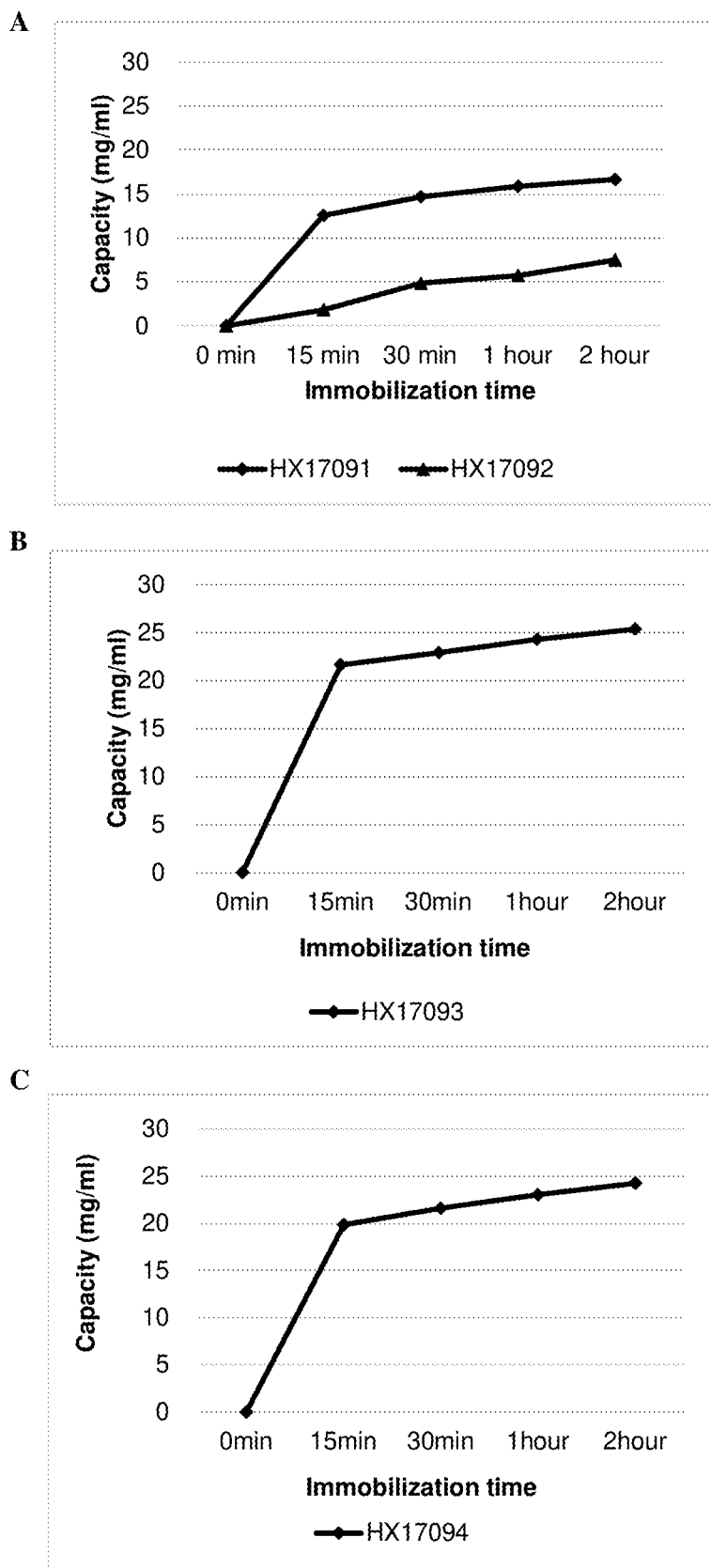
FIG. 3 depicts enzyme capacities of different Chloro Resins.

The results are shown in FIG. 3: the amount of Halo-Sortase immobilized on the Chloro Resin reaches to a plateau at the time point 2 h, showing the maximum capacity of each Chloro Resin.

Example 4: Characterization of Immobilized Halo-Sortase

Figure 4:
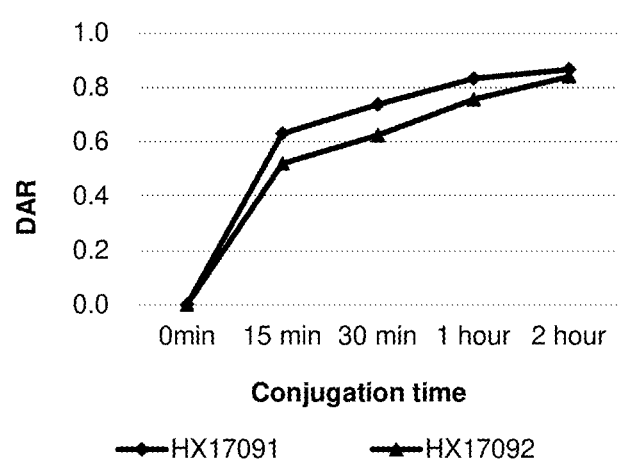
FIG. 4 depicts catalytic activities (expressed as DAR) of immobilized Halo-Sortase prepared from different Chloro Resins.
Figure 4:
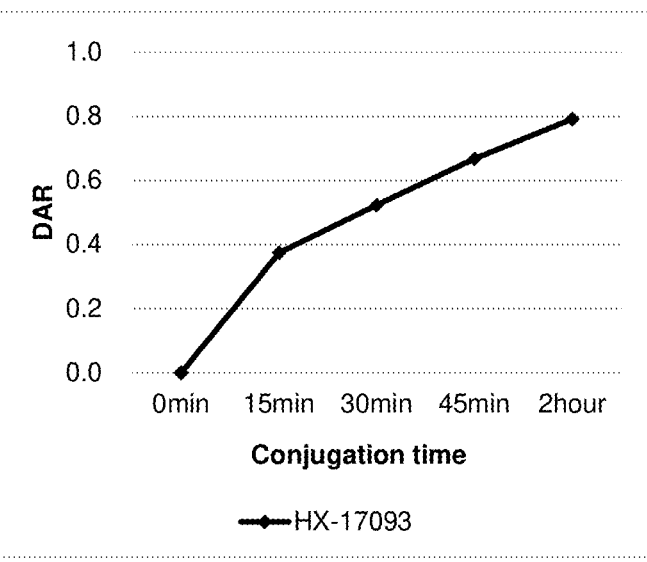
Figure 4:
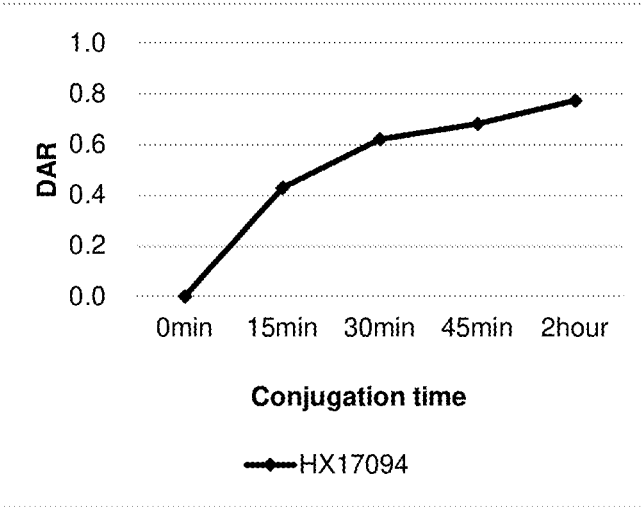

Procedures:
(1) Immobilize a fixed amount of Halo-sortase onto the Chloro Resin as in Example 2.2.
(2) Wash the immobilized enzyme with 5-10 resin volumes of 1× Storage Buffer for three times, each time centrifuging at 3000 g for 3 mM at room temperature to pellet the immobilized enzyme resin; resuspend the immobilized enzyme in conjugation buffer.
(3) Take 25 μl of each immobilized enzyme resin, add in 200 μl of GFP protein comprising a donor recognition motif LPETGG and small molecule reaction buffer containing the linker-payload intermediate, which comprises an acceptor recognition motif GGG coupled to a small molecule compound, to start the conjugation reaction.
(4) At different time points (15 mM, 30 min, 1 h and 2 h, respectively) of the conjugation reaction, take a sample of the supernatant for HIC-HPLC analysis.
(5) Determine the conjugation efficiency by HIC-HPLC. The results are shown in FIG. 4 (the conjugation activity is expressed as DAR over time).

Example 5: Solubility of the ADC Products Catalyzed by Halo-Sortase at Low Temperature Procedures:
(1) Prepare ADC samples using recombinant sortase proteins GB1-Sortase, His-Sortase or Halo-Sortase according to the method described in the "General procedures".
(2) Let the ADC samples stand on ice for 10 min.
(3) Centrifuge the ADC samples at 12000 g for 5 mM and transfer the supernatant to a new tube.
(4) Add 20 μl 1×SDS Loading Buffer to the precipitate of step (3) to dissolve the precipitate and take 5 μl for sample loading.
(5) Boil all the samples at 95° C. for 10 mM and load the samples to a 12% SDS-PAGE gel for analysis.

Figure 5:
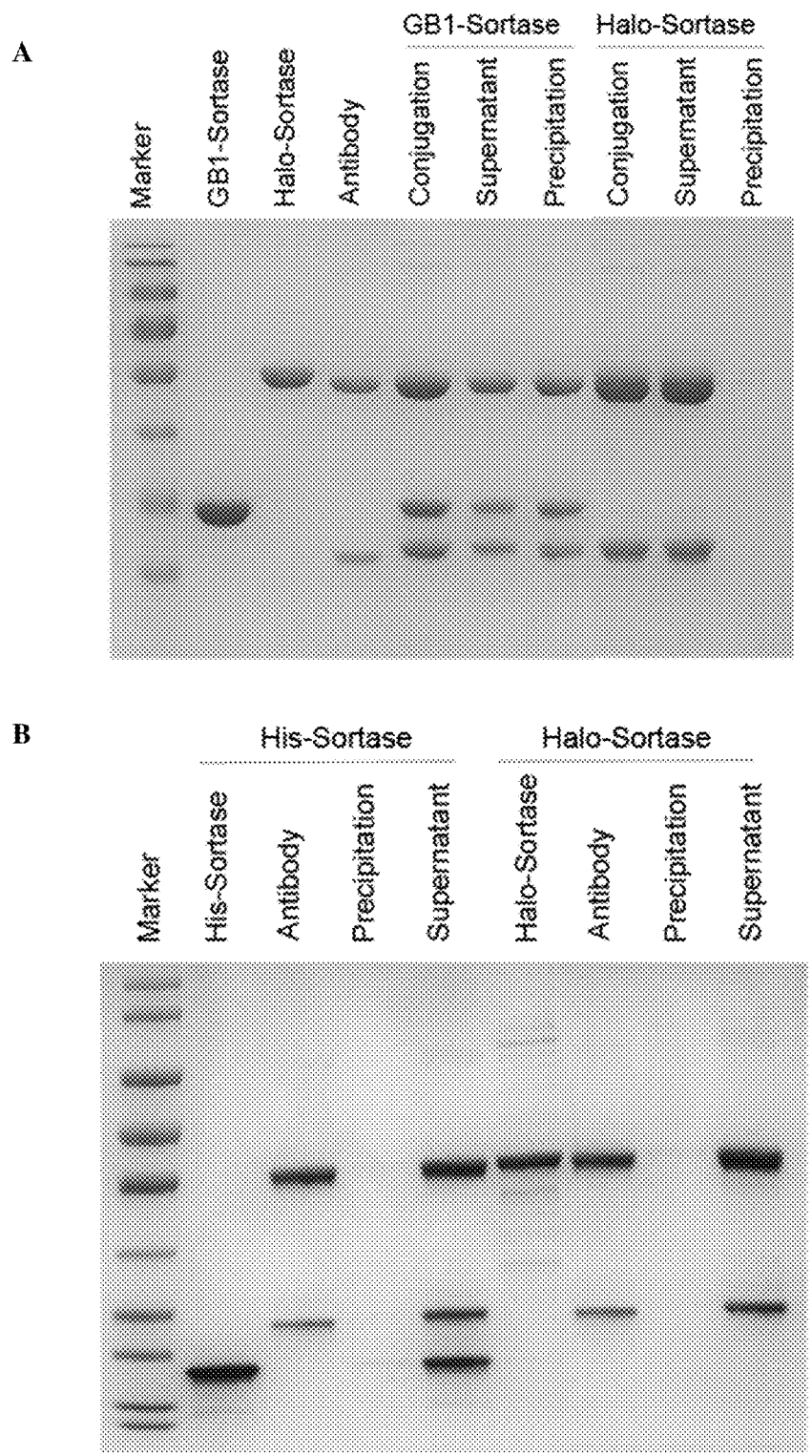
FIG. 5 shows the solubility of ADC products catalyzed by GB1-Sortase, His-Sortase or Halo-Sortase at low temperature.

The results are shown in FIG. 5: most of the GB1-Sortase catalyzed ADCs precipitate when placed on ice, while there is no precipitation from Halo-Sortase or His-Sortase catalyzed ADCs. The results suggest that ADCs catalyzed by Halo-Sortase or His-Sortase are more stable under cold conditions comparing to those catalyzed by GB1-Sortase and may survive in a conjugation process with a longer hold-time, which is typical for bioconjugate production. Therefore, His-Sortase and Halo-Sortase have an advantage over GB1-Sortase in terms of product solubility.

Example 6: Separation of Halo-Sortase and ADC

6.1 Separation of Halo-Sortase and ADC Using Anion Exchange Chromatography (AEX)

Procedures:
(1) Pack column with Q Sepharose FF medium.
(2) Equilibrate column with 20 mM Tris-HCl (pH 7.5) and apply the samples (A: ADCs, B: Halo-Sortase, and C: Mixture of ADCs and Halo-Sortase (the mass ratio of ADC:Halo-Sortase is about 100:1, respectively).
(3) Flush the column with 20 mM Tris-HCl (pH 7.5) until the baseline, eluent pH, and conductivity are stable.
(4) Regenerate the column with 20 mM Tris-HCl, 1 M NaCl (pH 7.5).
(5) Perform cleaning-in-place (CIP) with 1 M NaOH.

Figure 6:
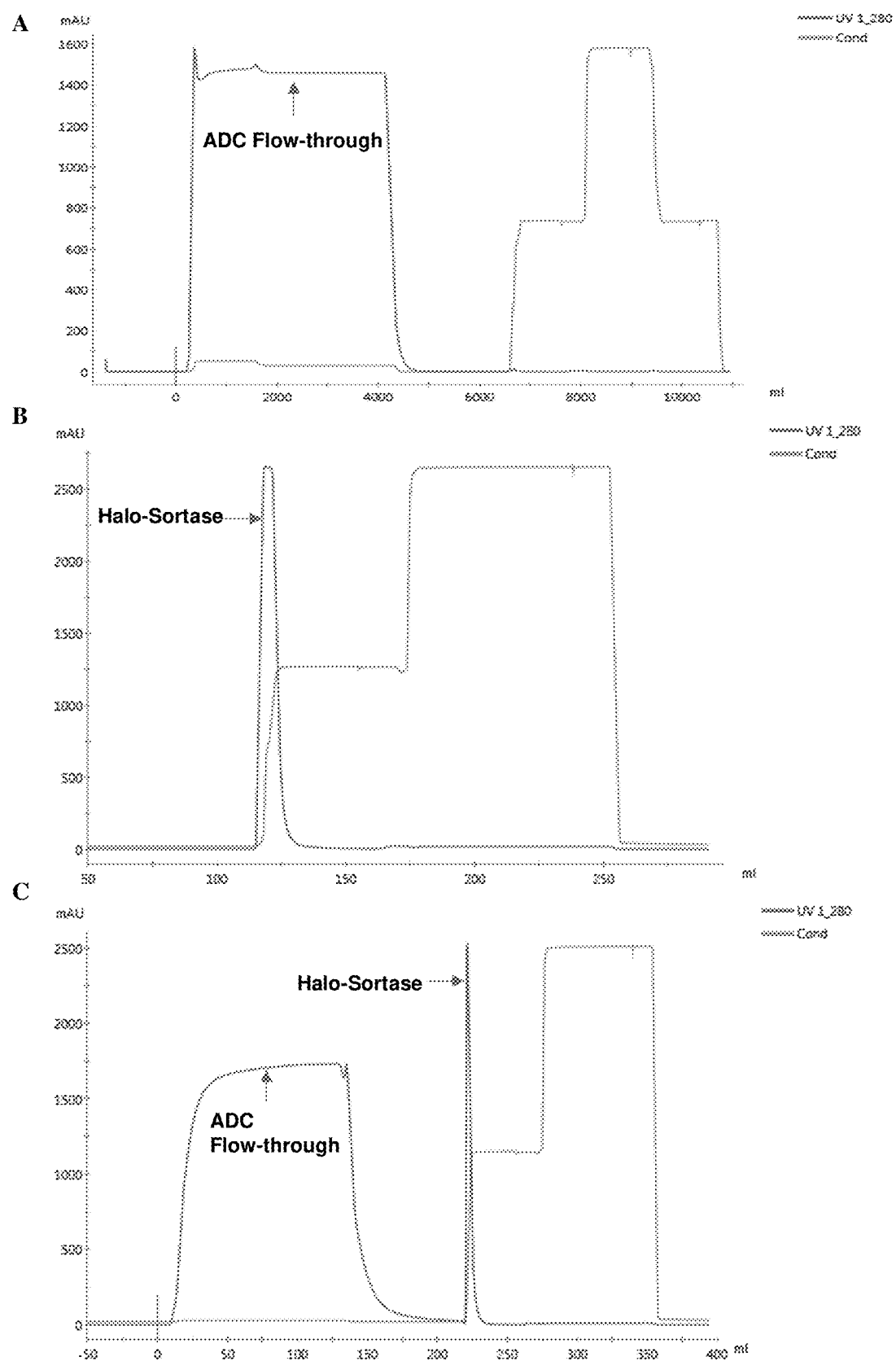
FIG. 6 depicts chromatography profiles of (A) ADC, (B) Halo-Sortase and (C) ADC+Halo-Sortase on AEX using Q Sepharose FF medium.

The results are shown in FIG. 6: at pH 7.5, ADCs pass through the Q FF column (flow-through [FT] mode), which is consistent with the conventional ADC&Ab purification procedure; Halo-Sortase binds to the Q FF column (bind/elute [B/E] mode) and is eluted by 20 mM Tris-HCl, 1 M NaCl pH 7.5; for the mixture of ADCs & Halo-Sortase, ADCs pass through the Q FF column, while Halo-Sortase binds the Q FF column, and the two are well-separated.

6.2 Separation of Halo-Sortase and ADC Using Cation Exchange Chromatography (CEX)

Procedures:
(1) Pack column with Capto S ImpAct medium.
(2) Equilibrate column with 20 mM citric acid-sodium citrate (pH 6.2) and apply the samples (A: ADCs and B: Halo-Sortase, and C: Mixture of ADCs and Halo-Sortase, respectively).
(3) Equilibrate column with 20 mM citric acid/sodium citrate (pH 6.2) until the baseline, eluent pH, and conductivity are stable.
(4) Elute the sample with 20 mM citric acid/sodium citrate, 160 mM NaCl, pH 6.2.
(5) Regenerate the column with 20 mM citric acid/sodium citrate, 1 M NaCl, pH 6.2 and perform cleaning-in-place (CIP) with 1 M NaOH.

Figure 7:
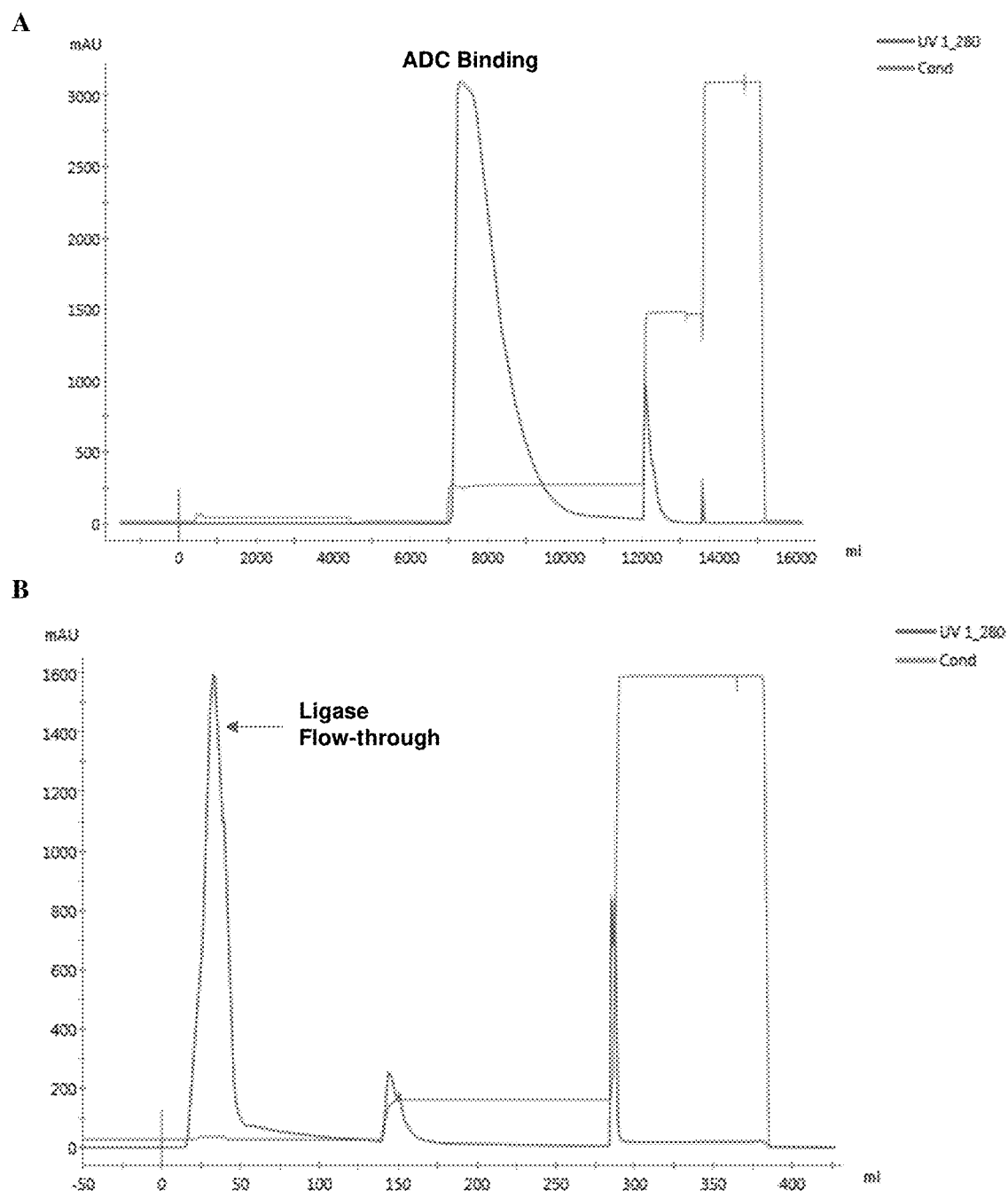
FIG. 7 depicts chromatography profiles of (A) ADC and (B) Halo-Sortase on CEX using Capto S impact medium.
Figure 8:
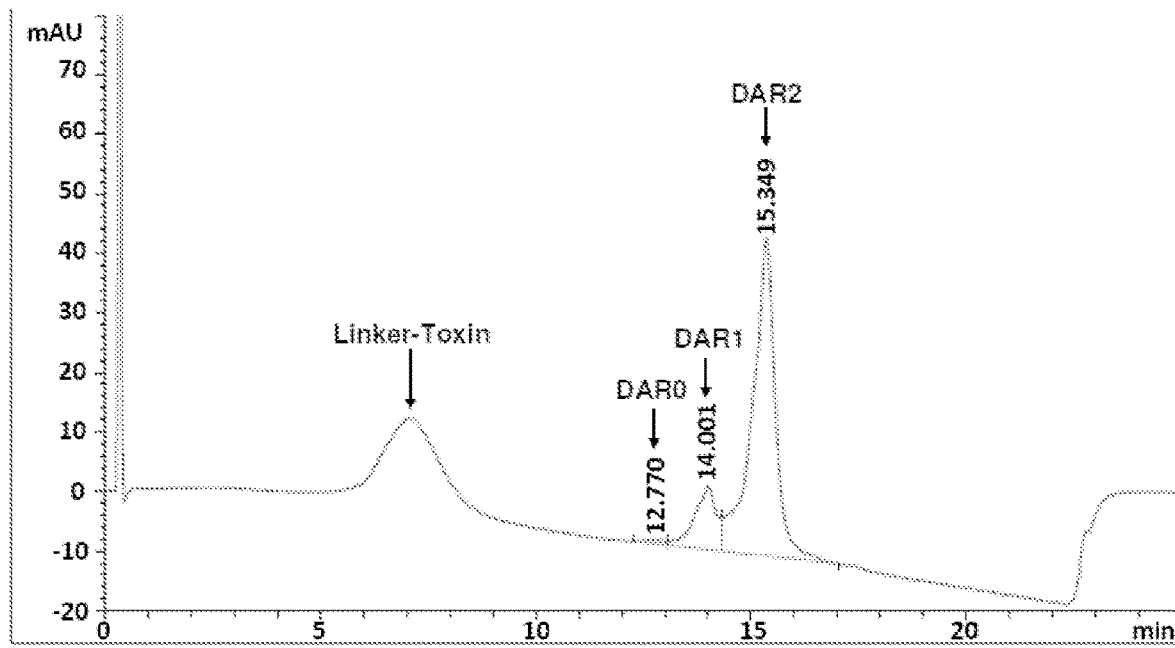
FIG. 8 depicts the DAR compositions of conjugates comprised in the crude conjugate mixture of Process 2 analyzed by HIC-HPLC.
Figure 9:
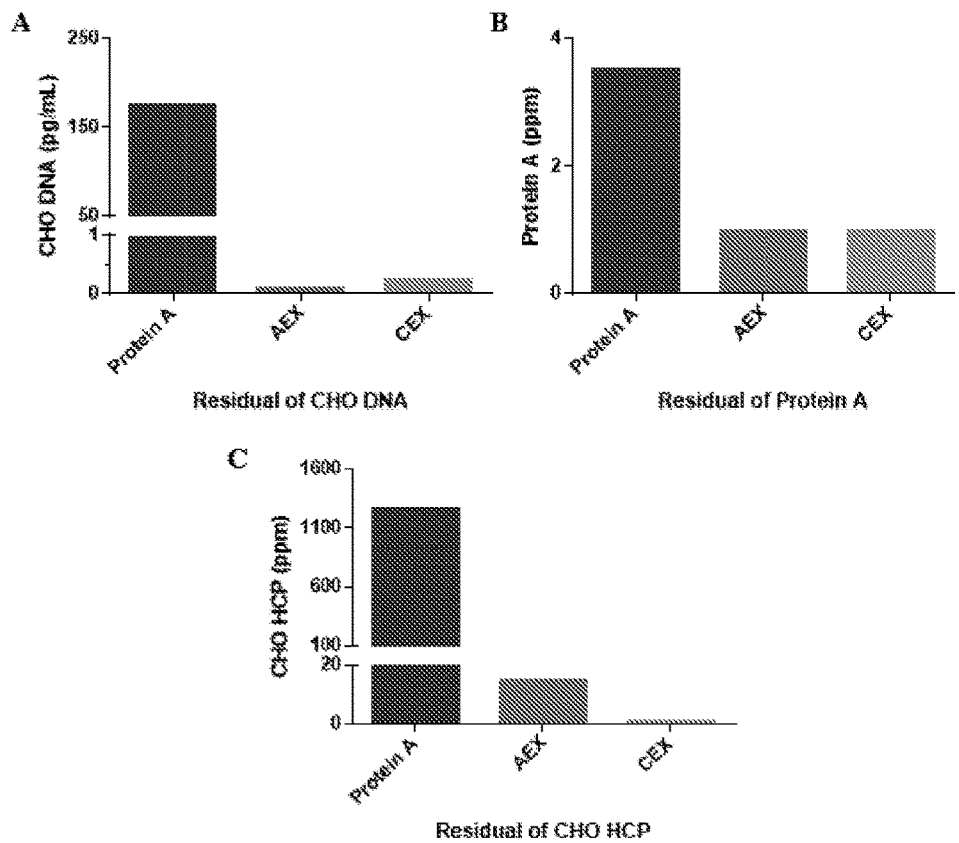
FIG. 9 shows the amount of residual impurities in samples containing the target ADCs after each chromatography step in Process 2: Protein A, mAb eluate from Protein A affinity chromatography; AEX, ADC flow-through from AEX; CEX, ADC eluate from CEX.
Figure 10:
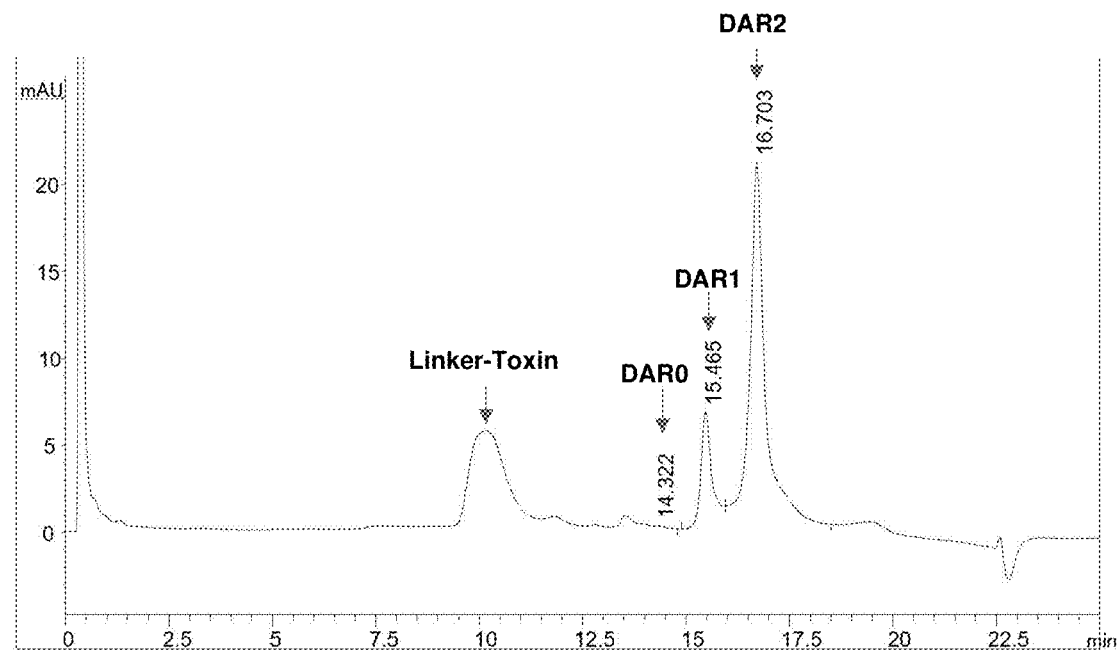
FIG. 10 depicts the DAR compositions of conjugates comprised in the crude conjugate mixture of Process 1 analyzed by HIC-HPLC.
Figure 11:
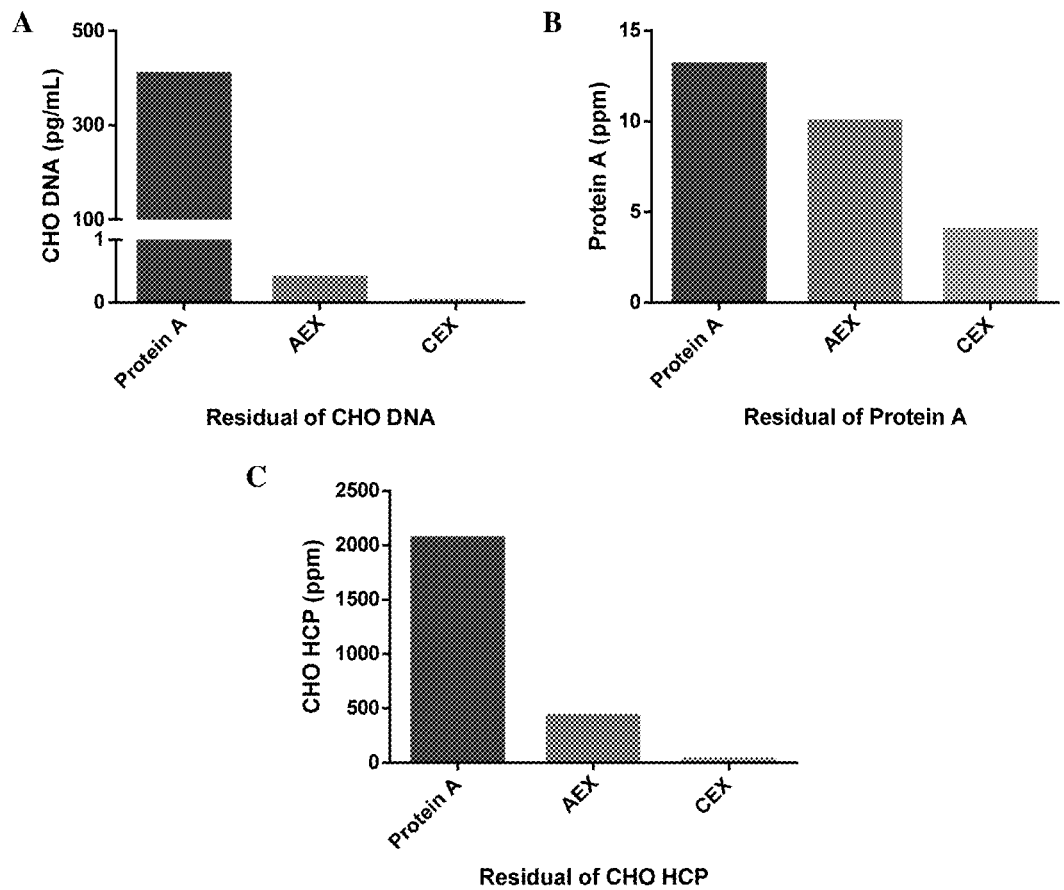
FIG. 11 shows the amount of residual impurities in samples containing the target ADCs after each chromatography step in Process 1: Protein A, ADC eluate from Protein A affinity chromatography; AEX, ADC flow-through from AEX; CEX, ADC eluate from CEX.
Figure 12:
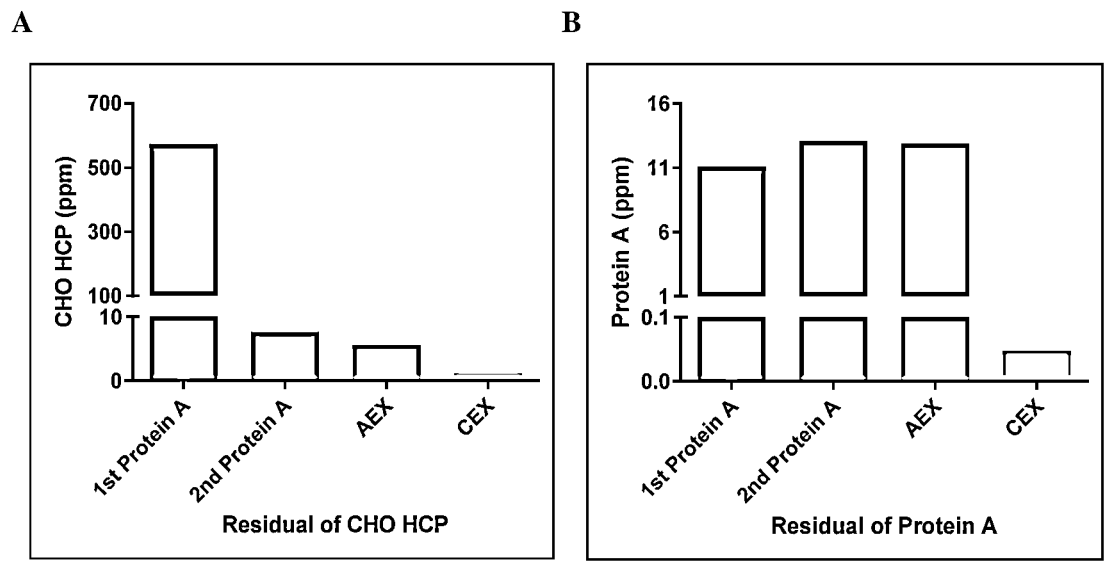
FIG. 12 shows the amount of residual impurities in samples containing the target ADCs after each chromatography step in Process 3: 1st Protein A, mAb eluate from Protein A affinity chromatography; 2nd Protein A, ADC eluate from Protein A affinity chromatography; AEX, ADC flow-through from AEX; CEX, ADC eluate from CEX.

The results are shown in FIG. 7: at pH 6.2, ADCs bind to the Capto S impact column (bind/elute [B/E] mode); at pH 7.5, Halo-Sortase flows through the Capto S impact column (flow-through [FT] mode); for the mixture of ADCs & Halo-Sortase, ADCs bind to the Capto S impact column, while Halo-Sortase passes through, and the two are well-separated.

6.3 Comparison on the Removal of His6-Sortase or Halo-Sortase from the Reaction Product The isoelectric points of His6-Sortase and Halo-Sortase and modes of chromatography (AEX and CEX) used for separating $His_6$-Sortase or Halo-Sortase and the reaction product ADC are shown in Table 3. $His_6$-Sortase has an isoelectric point of 8.92, which is close to that of ADC (8-9). $His_6$-Sortase and ADC both bind to the cation exchanger in CEX and both pass through the anion exchanger in AEX, making it difficult to separate the two. Halo-Sortase has an isoelectric point of 5.7. Halo-Sortase and ADC can be easily separated using either AEX or CEX.

TABLE 3

|  | $His_6$-Sortase | Halo-Sortase | ADC |
| --- | --- | --- | --- |
| Isoelectric point | 8.92 | 5.70 | 8-9 |
| Mode on AEX | Flow-though | Bind-and-elute | Flowt-hough |
| Mode on CEX | Bind-and-elute | Flow-though | Bind-and-elute |

Example 7: Preparation of ADCs Using Antibody Purified by the Protein a Affinity Chromatography (Process 2

7.1 Conjugation Reaction

The target ADCs are prepared according to the method described in the "General procedures", using the monoclonal antibody (mAb) obtained from Protein A affinity chromatography of the HCCF (i.e., mAb eluate from Protein A affinity chromatography). The content of HCP is 1000 to 2000 ppm in the antibody feed. The container used for conjugation reaction is the Halo-Sortase column prepared in Example 2.2. The crude conjugate mixture is collected as the flow-through from the Halo-Sortase column. According to the HIC-HPLC analysis (see FIG. 9), the DAR of ADCs prepared is 1.83. The conjugation efficiency is 91.6% (Table 4).

TABLE 4

| DAR0 Area (%) | DAR1 Area (%) | DAR2 Area (%) | DAR | Conjugation Efficiency |
| --- | --- | --- | --- | --- |
| 0.80 | 15.31 | 83.89 | 1.83 | 91.6% |

7.2 Removal of the Impurities

The crude conjugate mixture collected in 7.1 is subjected to AEX and CEX sequentially; and the samples containing the target ADCs from each step (ADC flow-through from AEX and ADC eluate from CEX, respectively) are collected. The mAb eluate from Protein A affinity chromatography, ADC flow-through from AEX and ADC eluate from CEX are analyzed using ELISA and qPCR to determine the amount of residual impurities.

An approximately one-log reduction (90%) of the HCP content is observed after the AEX chromatography. And the levels of HCP, DNA and Protein A are all reduced to below 1 ppm after the series of chromatography purification (see FIG. 10).

Example 8: Preparation of ADCs Using the Antibody Obtained from HCCF (Process 1

8.1 Conjugation Reaction

The target ADCs are prepared according to the method described in the "General procedures", using HCCF as the antibody feed. The content of CHO HCP is 100000 to 1000000 ppm in the antibody feed.

The container used for conjugation reaction is the Halo-Sortase column prepared in Example 2.2. The crude conjugate mixture is collected as the flow-through from the Halo-Sortase column. According to the HIC-HPLC analysis (see FIG. 11), the DAR of ADCs prepared is 1.81, and the conjugation efficiency is 90.5% (see Table 5).

TABLE 5

| DAR0 Area (%) | DAR1 Area (%) | DAR2 Area (%) | DAR | Conjugation Efficiency |
| --- | --- | --- | --- | --- |
| 0.33 | 18.51 | 81.16 | 1.81 | 90.5% |

8.2 Detection and Removal of the Impurities

The crude conjugate mixture collected in 8.1 is subjected to Protein A affinity chromatography, AEX and CEX sequentially; and the ADC-containing solutions from each step (ADC eluate from Protein A affinity chromatography, ADC flow-through from AEX and ADC eluate from CEX, respectively) are analyzed using ELISA and qPCR to determine the amount of residual impurities.

An approximately 80% reduction of the HCP content and an approximately three-log reduction (99.9%) of the DNA content are observed after the AEX chromatography. An approximately 93% reduction of the HCP content is observed after the CEX chromatography. And the levels of DNA and Protein A are reduced to below 5 ppm, the level of HCP is reduced to below 40 ppm, after the series of chromatography purification (see FIG. 11).

The process of the present disclosure is suitable for fast preparation of ADCs, especially at small scales, for example in a lab, or in the high through-put preparation of ADCs for the purposes such as investigation for bioactivities.

Example 9: Preparation of ADCs Using Antibody Purified by the Protein a Affinity Chromatography (Process 3

9.1 Conjugation Reaction

The target ADCs are prepared according to the method described in the "General procedures", using the monoclonal antibody obtained from the Protein A affinity chromatography of the HCCF (i.e., mAb eluate from Protein A affinity chromatography). The container used for conjugation reaction is the Halo-Sortase column prepared in Example 2.2. The crude conjugate mixture is collected as the flow-through from the Halo-Sortase column.

9.2 Removal of the Impurities

The crude conjugate mixture collected in 9.1 is subjected to Protein A affinity chromatography, AEX and CEX sequentially, in a manner similar to 8.2. The mAb eluate from Protein A affinity chromatography, ADC eluate from Protein A affinity chromatography, ADC flow-through from AEX and ADC eluate from CEX are analyzed using ELISA and qPCR to determine the amount of residual impurities. The result shows that the levels of HCP and Protein A are reduced to below 2 ppm after the series of chromatography purification (see FIG. 12). Therefore, applying two Protein A affinity chromatography steps would not influence the quality of the product in the aspect of possibly leached Protein A. And the low levels of impurities in the eluate of the second Protein A affinity chromatography step indicates that this method could tolerate higher loading amount/higher complexity of the loading sample. And thus the present example can be interpreted as a conceptual validation of purification process which is more complicated as compared to those described in Example 7 and Example 8.

9.3 Removal of Residual Enzyme Contaminants (i.e., Enzymes that Fall Off from the Halo-Sortase Column after Conjugation)

Crude conjugate mixture is collected as the flow-through from the Halo-Sortase column as described in Example 9.1 and then subjected to Protein A affinity chromatography, AEX and CEX sequentially. The crude conjugate mixture, ADC eluate from Protein A affinity chromatography, ADC flow-through from AEX and ADC eluate from CEX are subjected to ELISA analysis to determine the amount of residual enzyme contaminants.

Figure 13:
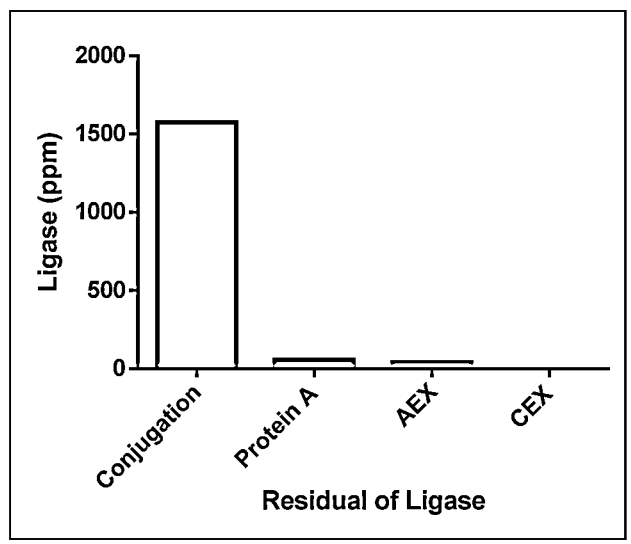
FIG. 13 depicts amounts of residual Halo-Sortase in samples containing the target ADCs: Conjugation, crude conjugate mixture collected as the flow-through from the Halo-Sortase column; Protein A, ADC eluate from Protein A affinity chromatography; AEX, ADC flow-through from AEX; CEX, ADC eluate from CEX.

As shown in FIG. 13, a three-log reduction (99.9%) of residual enzyme contaminants is achieved after a series of chromatography purification. In particular, comparing to one step purification using Protein A affinity chromatography only, anion exchange chromatography and cation exchange chromatography further reduce the amount of residual enzyme in the final products by about 78%.

Example 10: Separation of the Linker-Payload Intermediate and ADC

Conventional process for the removal of the linker-payload intermediate from the crude conjugate mixture containing the target ADCs typically involves ultrafiltration (UF). However, the shear force produced during the ultrafiltration process increases the risk of protein molecule aggregation. This is of particular concern in the case of removing small molecules (e.g., the linker-payload intermediate) from the product ADCs, because of the long ultrafiltration time and the enhanced hydrophobicity of ADCs as compared to the unconjugated protein molecules.

The present disclosure provides several choices of unit operations (process steps) to remove the linker-payload intermediate. Examples of the chromatography steps are provided hereinafter. In these examples, the ADC samples are prepared according to the method described in the "General procedures", using the antibody obtained from the Protein A affinity chromatography of the HCCF, or use HCCF as the antibody feed. The chromatography steps are performed according to the methods described in the "General procedures".

10.1 Protein a Affinity Chromatography

Figure 14:
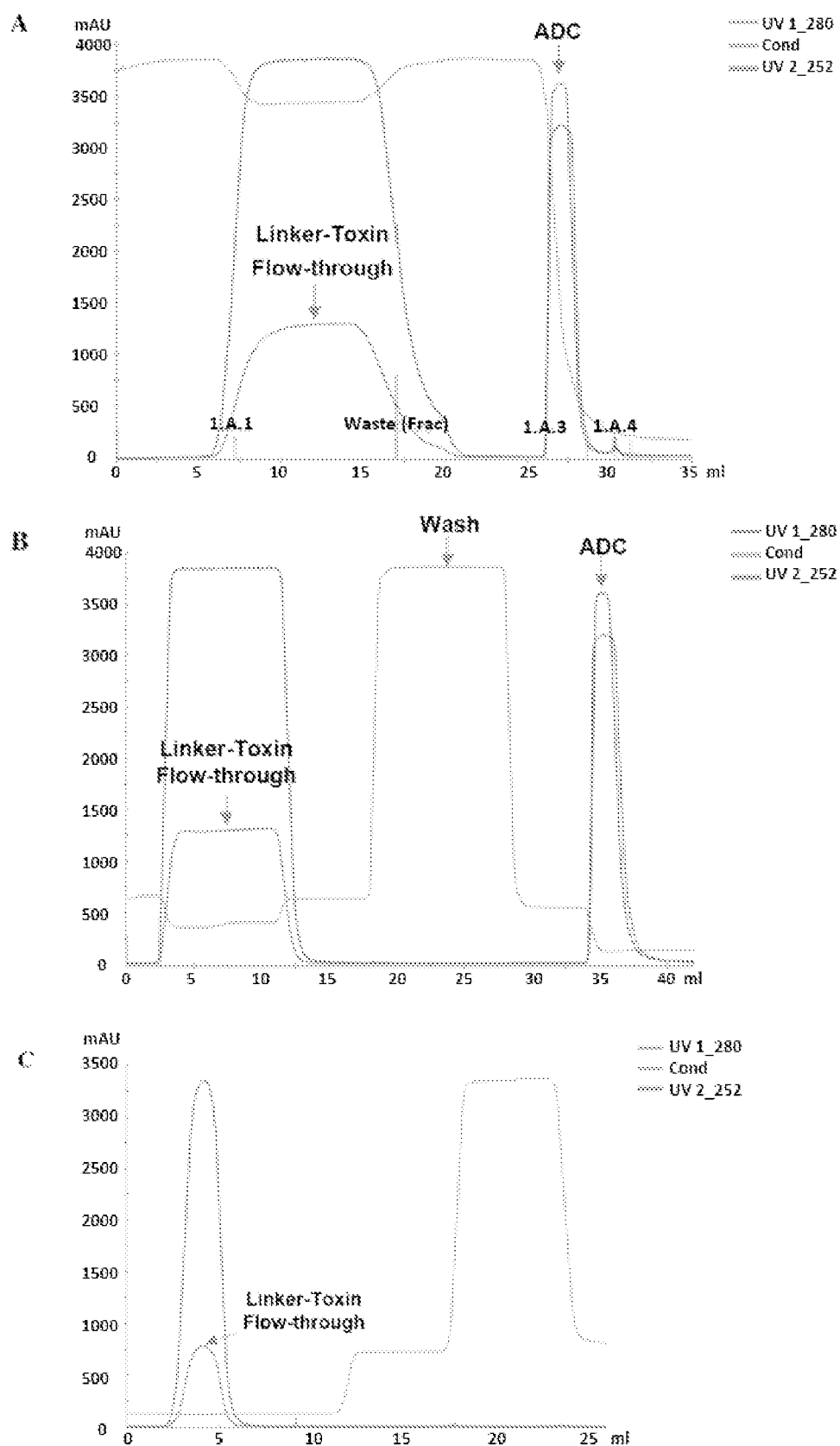
FIG. 14 shows optimized chromatography profiles of Linker-Toxin (linker-payload intermediate) removal by (A) Protein A media from Biomax, (B) Protein A media from GE; (C) CEX media from GE.

The target ADCs are prepared using a method similar to 9.1. The crude conjugate mixture is collected as the flow-through from the Halo-Sortase column and then subjected to Protein A affinity chromatography using Protein A chromatography media provided by different suppliers (Biomax and GE). The method employing GE Protein A comprises a Wash step. And the method employing Biomax Protein A does not comprise a Wash step. The results are shown in FIG. 14.

10.2 CEX

The target ADCs are prepared using a method similar to 9.1. The crude conjugate mixture is collected as the flow-through from the Halo-Sortase column and then subjected to CEX chromatography using CEX media provided by GE. The result is shown in FIG. 14.

10.3 Protein a Affinity Chromatography, AEX and CEX

The target ADCs are prepared using a method similar to 7.1. The crude conjugate mixture is collected as the flow-through from the Halo-Sortase column and then subjected to Protein A affinity chromatography, AEX and CEX sequentially. The samples containing the target ADCs from each step is analyzed by RP-HPLC for determination of residual linker-payload intermediate (Linker-Toxin).

A more than four-log reduction (more than 99.99%) of the linker-payload intermediate content is observed after the Protein A affinity chromatography.

The present disclosure provides diversified methods for the removal of the linker-payload intermediate, for example Protein A affinity chromatography, AEX, CEX and a combination thereof. Further purification can also be achieved by additional steps such as ultrafiltration and/or diafiltration, after the polishing step. Therefore, the linker-payload intermediate could be thoroughly removed.

Sequence Listing (sortase A)

SEQ ID NO: 1
AKPQIPKDKSKVAGYIEIPDADIKEPVYPGPATPEQLNRGVSFAE

Sequence Listing (sortase A)

ENESLDDQNISIAGHTFIDRPNYQFTNLKAAKKGSMVYFKVGNET
RKYKMTSIRDVKPTDVGVLDEQKGKDKQLTLITCDDYNEKT
GVWEKRKIFVATEVK (sortase A)

SEQ ID NO: 2

KTPEIPKDKSKMAGYIKVPDAEIEEPVYPGPATPEQLNRGVSFAE
GNESLSDQNISIAGHTFTDRPHYQFTNLKAAKKGSKVYFKVGNET
RKYKMTSIRDVDPSDVKVLDEHKGEKNQLTLITCDNYNKETG
VWEKRKIFVAKEIK (sortase A)

SEQ ID NO: 3

KAPAIPKDKSKMAGYIKVPDAEIEEPVYPGPATPEQLNRGVSFAE
GNESLTDQNISIAGHTFTDRPHYQFTNLKAAKKGSKVYFKVGNET
RKYKMTSIRNVDPSDVKVLDEHKGEKNQLTLITCDNYNKNT
GVWEKRKIFVAKQIN (sortase A)

SEQ ID NO: 4

KTPTIPKDKSKMAGYIEVPDAEIKEPVYPGPATLEQLNRGVSFAE
GDESLDQQNISIAGHTFTDRPHYQFTNLKAAKKGSKVYFKVGNQT
RKYKMTKIHDVNPSDVEVLDEQKGKKNQLTLITCDDYNEK
TGVWEKRKIFIATQVN (sortase A)

SEQ ID NO: 5

KAVEIPKDKSKMAGYIKIPDAEIEEPVYPGPATPEQLNRGVSFAE
GNESLSDQNISIAGHTFTDRPHYQFTNLKAAKKGSKVYFKVGNET
RKYKMTSIRDVDPSDVKVLDEHKGEKNQLTLITCDNYNKETGVWE
KRKIFVAKEIK (sortase A)

SEQ ID NO: 6

KAPEIPKDKSKMAGYIKVPDAEIEEPVYPGPATPEQLNRGVSFAE
GNESLTDQNISIAGHTFTDRPHYQFTNLKAAKKGSKVYFKVGNET
RKYKMTSIRDVDPSDVKVLDEHKGEKNQLTLITCDNYNKNTGVWE
KRKIFVAKQIN (sortase A)

SEQ ID NO: 7

KKPTIPKDKSKMAGYIEVPDAEIKEPVYPGPATPEQLNRGVSFAE
GDESLDQQNIAIAGHTFTDRPHYQFTNLKAAKKGSKVYFKVGNEV
RKYKMTKIHDVDPTEVKVLDEHKGKKNQLTLITCDDYNEQTGVWE
KRKIFVATQVN (sortase A)

SEQ ID NO: 8

KAVEIPKDKSKMVGYIKVPDAEIEEPVYPGPATPEQLNRGVSFAE
GNESLSDQNISIAGHTFTDRPHYQFTNLKAAKKGSKVYFKVGNET
RKYKMTSIRDVDPSDVKVLDEHKGEKNQLTLITCDNYNKETGVWE
KRKIFVAKEIK (sortase A)

SEQ ID NO: 9

ESPQIPKDKAKMAGYIEIPDAQIKEPVYPGPATPQQLNRGVSFAE
GDESLNQQNISIAGHTFTDRPHYQFTNLKAAKKGSKVYFKVGNQT
RKYKITKIHDVKPTEVKVLDEHPSKKNQLTLITCDDYNEQTGVWE
TRKIFVATQMN (sortase A)

SEQ ID NO: 10

STPKIPSDKSKMAGYIEVPDAQIKEPVYPGPATPEQLNRGVSFAE
GDESLNQQNISIAGHTFTDRPHYQFTNLKSAKIGSKVYFKTGNQT
RKYKITKIRDVKPTEVKVLDEHPNKKNQLTLITCDDYNEETGVWE
TRKIFIATQIN (sortase A)

SEQ ID NO: 11

ERPQIPKDKAKMAGYIEIPDAQIKEPVYPGPATPQQLNRGVSFAE
GDESLYQQNISIAGHTFTDRPHYQFTNLKAAKKGSKVYFKVRNQT
RKYKITKIHDVKPTEVKVLDEHPSKKNQLTLITCDDYNEQTGVWE
TRKIFVATQMN (sortase A)

SEQ ID NO: 12

STPKIPSDKSKMAGYIEVPDAQIKEPVYPGPATPEQLNRGVSFAE
GDESLNQQNISIAGHTFTDRSHYQFTNLKSAKIGSKVYFKTGNQT
RKYKITKIRDVKPTEVKVLDEHPNKKNQLTLITCDDYNEETGVWE
TRKIFIATQIN (sortase A)

SEQ ID NO: 13

EKPTISKDKSKMTGYISIPDADIKEPVYPGPATPEQLNRGVSFAE
EDESLDDQNISIAGHTFIDRPNYQFTNLKAAKKGSKVTFKIGNET
RKYKMTSIRDVNPEDVEVLDEHKGKKNQLTLITCDDYNENTGVWE
KRKIFVAEEVK (sortase A)

SEQ ID NO: 14

EKPTISKDKSKMTGYISIPDADIKEPVYPGPATPEQLNRGVSFAE
EDESLDDQNISIAGHTFTDRPNYQFTNLKAAKKGSKVTFKIGNET
RKYKMTSIRDVDPDAVEVLDENKGKKNQLTLITCDDYNENTGVWE
KRKIFVAEQIK (sortase A)

SEQ ID NO: 15

EKPTISKDKSKMTGYISIPDADIKEPVYPGPATPEQLNRGVSFAE
EDESLDDQNISIAGHTFTDRPNYQFTNLKAAKKGSKVTFKTGNET
RKYKMTSIRDVDPDAVEVLDENKGKKNQLTLITCDDYNENTGVWE
KRKIFVAEQIK (sortase A)

SEQ ID NO: 16

ETPTIPKDKSKMAGYISIPDAEIKEPVYPGPATPEQLNRGVSFAE
EDEKLDDQNISIAGHTFIDRPHYQFTNLKAAKKGSKVYFKVGNET
RKYKMTSIRDVNPDDVKVLDEHKGETNQLTLITCDNYNEQTGIWE

| Sequence Listing |
|---|
| KRKIFVAKQIN |
| (sortase A) |
| SEQ ID NO: 17 |
| ETPTIPKDKSKMAGYISIPDAEIKEPVYPGPATPEQLDRGVSFAE |
| EDEKLDDQNISIAGHTFIDRPHYQFTNLKAAKKGSKVYFKVGNET |
| RKYKMTSIRDVNPDDVKVLDEHKGETNQLTLITCDNYNEQTGIWE |
| KRKIFIAKQIN |
| (sortase A) |
| SEQ ID NO: 18 |
| EKPTIPKDKSKMAGYISVPDAEIKEPVYPGPATPEQLNRGVSFAE |
| GDESLDDQNISIAGHTFTDRPHYQFTNLKAAKKGSKVYFKVGDET |
| REYKMTSIRDVDPEDVQVLDEHKGETNQLTLITCDNYNQQTGVWE |
| KRKIFVAKQIK |
| (sortase A) |
| SEQ ID NO: 19 |
| ERPTIPKNKSEMAGYISIPDAEIKEPVYPGPATLEQLNRGVSFAE |
| GDESLDDQNISIAGHTFTDRPHYQFTNLKAAKKGSKVYFKVGDET |
| REYKMTSIRDVDPEDVQVLDEHKGETNQLTLITCDNYNQQTGVWE |
| KRKIFVAKQIK |
| (sortase A) |
| SEQ ID NO: 20 |
| QTPTIPKDKSKMAGYISVPDAEIKEPVYPGPATPEQLNRGVSFAE |
| EDESLSDQNISIAGHTFTDRPHYQFTNLKAAKKGSKVYFKIGNET |
| REYKMTSIRDVNPDQVEVLNEHKGEKNQLTLITCDDYNEQTGVWE |
| KRKIFVAKQVK |
| (sortase A) |
| SEQ ID NO: 21 |
| QTPTIPKDKTKMAGYISVPDAEIKEPVYPGPATPEQLNRGVSFAE |
| KDESLSDQNISIAGHTFTDRPHYQFTNLKAAKKGSKVYFKIGNET |
| REYKMTSIRDVNPDEVEVLDEHKGEKNQLTLITCDDYNEQTGVWE |
| KRKIFVAKQVK |
| (sortase A) |
| SEQ ID NO: 22 |
| ERPTIPKDKSKMAGYISVPDAEIKEPVYPGPATLEQLNRGVSFAE |
| GDESLDDQNISIAGHTFTDRPHYQFTNLKAAKKGSKVYFKVGDET |
| REYKMTSIRDVNPEDVQVLDEHEGETNQLTLITCDNYNQQTGVWE |
| KRKIFVAKQIK |
| (sortase A) |
| SEQ ID NO: 23 |
| QTPTIPKDKTKMAGYISVPDAEIKEPVYPGPATPEQLNRGVSFAE |
| KDESLSDQNISIAGHTFTDRPHYQFTNLKAAKKGSKVYFKIGNET |
| REYKMTSIRDVNPDEVEVLDEHKGEKNQLTLITCDDYNEQTGVWE |
| KRKIFVAKQVN |
| (sortase A) |
| SEQ ID NO: 24 |
| DKPTIPKDKAEMAGYLRIPDADINEPVYPGPATPEQLNRGVSFAE |
| EQESLDDQNIAIAGHTYIGRPHYQFTNLKAAKKGSKVYFKVGNET |
| REYKMTTIRDVNPDEIDVLDEHRGDKNRLTLITCDDYNEKTGVWE |
| KRKIFIAEQIK |
| (sortase A) |
| SEQ ID NO: 25 |
| QTPTIPKDKTKMAGYISVPDAEIKEPVYPGPATPEQLNRGVSFTE |
| KDESLSDQNISIAGHTFTDRPHYQFTNLKAAKKGSKVYFKIGNET |
| REYKMTSIRDVNPDEVEVLDEHKGEKNQLTLITCDDYNEQTGVWE |
| KRKIFVAKQVN |
| (sortase A) |
| SEQ ID NO: 26 |
| DKPTIPKDKAEMAGYLRIPDADINEPVYPGPATPEQLNRGVSFAE |
| EQESLDDQNIAIAGHTYIGRPHYQFTNLKAAKKGSKVYFKVGNET |
| REYKMTTIRDVDPDEIDVLDEHRGDKNRLTLITCDDYNEKTGVWE |
| KRKIFIAEQIK |
| (sortase A, SNAT counterpart of SEQ ID NO: 1) |
| SEQ ID NO: 27 |
| AKPQIPKDKSKVAGYIEIPDADIKEPVYPGPATSEQLNRGVSFAE |
| ENESLDDQNISIAGHTFIDRPNYQFTNLKAAKKGSMVYFKVGNET |
| RKYKMTSIRNVKPTAVGVLDEQKGKDKQLTLITCDDYNEKTGVWE |
| TRKIFVATEVK |
| (Halo tag) |
| SEQ ID NO: 28 |
| MAEIGTGFPFDPHYVEVLGERMHYVDVGPRDGTPVLFLHGNPTSS |
| YVWRNIIPHVAPTHRCIAPDLIGMKSDKPDLGYFFDDHVRFMDA |
| FIEALGLEEVVLVIHDWGSALGFHWAKRNPERVKGIAFMEFIRPI |
| PTWDEWPEFARETFQAFRTTDVGRKLIIDQNVFIEGTLPMGVVRP |
| LTEVEMDHYREPFLNPVDREPLWRFPNELPIAGEPANIVALVEEY |
| MDWLHQSPVPKLLFWGTPGVLIPPAEAARLAKSLPNCKAVDIGPG |
| LNLLQEDNPDLIGSEIARWLSTLEISG |
| (Halo-Sortase) |
| SEQ ID NO: 29 |
| MAEIGTGFPFDPHYVEVLGERMHYVDVGPRDGTPVLFLHGNPTSS |
| YVWRNIIPHVAPTHRCIAPDLIGMKSDKPDLGYFFDDHVRFMDA |
| FIEALGLEEVVLVIHDWGSALGFHWAKRNPERVKGIAFMEFIRPI |
| PTWDEWPEFARETFQAFRTTDVGRKLIIDQNVFIEGTLPMGVVRP |
| LTEVEMDHYREPFLNPVDREPLWRFPNELPIAGEPANIVALVEEY |
| MDWLHQSPVPKLLFWGTPGVLIPPAEAARLAKSLPNCKAVDIGPG |
| LNLLQEDNPDLIGSEIARWLSTLEISGGGGGSGGGGSAKPQIPKD |
| KSKVAGYIEIPDADIKEPVYPGPATSEQLNRGVSFAEENESLDDQ |
| NISIAGHTFIDRPNYQFTNLKAAKKGSMVYFKVGNETRKYKMTSI |
| RNVKPTAVGVLDEQKGKDKQLTLITCDDYNEKTGVWETRKIFVAT |
| EVK |

The invention claimed is:

1. A process for preparing a conjugate of formula (III):

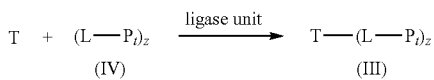

wherein the process comprises contacting T and formula (IV) with a ligase unit to catalyze conjugation of T and formula (IV),
wherein the ligase unit comprises a ligase fusion protein immobilized to a support comprising a ligase which is a sortase and a Halo tag;
wherein the ligase fusion protein has an isoelectric point (pI) that is lower than that of the ligase from which the ligase fusion protein is derived;
wherein T comprises a protein, a peptide, an antibody, or an antibody fragment, which is modified to have either a recognition motif of the ligase donor substrate or a recognition motif of the ligase acceptor substrate;
L comprises a linker, which comprises the other of the recognition motif of the ligase donor substrate and the recognition motif of the ligase acceptor substrate;
P comprises a payload;
z is an integer of 1-20; and
t is an integer of 1-20.

2. The process according to claim 1, wherein at least one of T and formula (IV) comprise one or more impurities.

3. The process according to claim 1, wherein a harvested clarified cell culture fluid (HCCF) comprises T.

4. The process according to claim 1, wherein the ligase unit comprises a sortase A.

5. The process according to claim 1, wherein the support comprises a haloalkyl linker such that the ligase fusion protein is immobilized on the support through covalent interaction between the haloalkyl linker and the Halo tag.

6. The process according to claim 1, further comprising the steps of
(1) subjecting T to one or more chromatography steps to remove one or more impurities prior to contacting T with formula (IV), and/or
(2) subjecting formula (IV) to one or more chromatography steps to remove one or more impurities prior to contacting formula (IV) with T, and/or
(3) subjecting the conjugate obtained, to one or more chromatography steps to remove one or more impurities.

7. The process according to claim 6, wherein the chromatography step is independently selected from affinity chromatography, hydrophobic interaction chromatography, ion exchange chromatography, and a combination thereof.

8. The process according to claim 7, wherein at least one of steps (1)-(3) comprises an affinity chromatography.

9. The process according to claim 7, wherein T comprises an Fc fragment,
steps (1) and (2) do not exist, and step (3) comprises the steps in any order:
(3a-1): Protein A affinity chromatography;

(3a-2): anion exchange chromatography; and
(3a-3): cation exchange chromatography;
or
step (1) or step (2) comprises a Protein A affinity chromatography, and step (3) comprises the steps in any order:
(3b-1): anion exchange chromatography; and
(3b-2): cation exchange chromatography;
or
step (1) or step (2) comprises a Protein A affinity chromatography, and step (3) comprises the steps in any order:
(3c-1): Protein A affinity chromatography;
(3c-2): anion exchange chromatography; and
(3c-3): cation exchange chromatography.
10. The process according to claim 7, wherein
the affinity chromatography is performed in bind-and-elute mode; and/or
the ion exchange chromatography is performed in bind-and-elute mode or flow-through mode.

11. The process according to claim 1, wherein the process is performed in batch mode, semi-continuous mode or continuous mode.
12. The process according to claim 6, wherein at least one of, the conjugation and steps (1)-(3) is performed in semi-continuous mode or continuous mode.
13. The process according to claim 1, wherein
the ligase is a sortase A; and/or
the recognition motif of the ligase donor substrate is LPXTGJ; and/or
the recognition motif of the ligase acceptor substrate is $G_n$, wherein G is glycine (Gly), and n is an integer of 3-10;
X is any natural or unnatural amino acid;
J is absent, or is an amino acid fragment comprising 1-10 amino acids, wherein each amino acid is independently any natural or unnatural amino acid.
14. The process according to claim 1, wherein the conjugate has the structure selected from the following formulae (3), (3'), (5) and (5'):

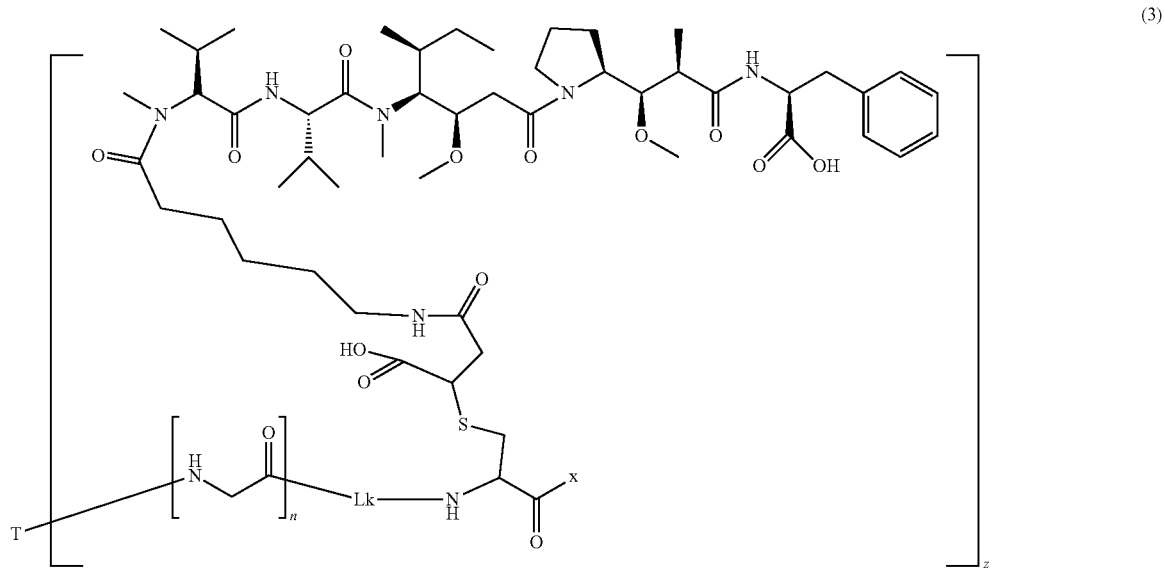

(3)

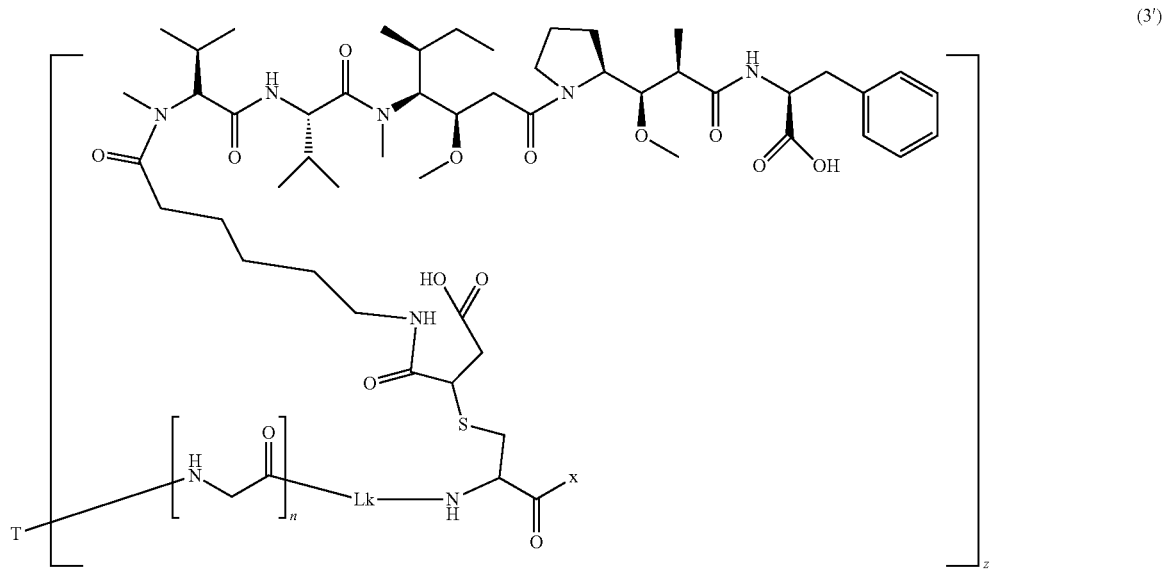

(3')

-continued

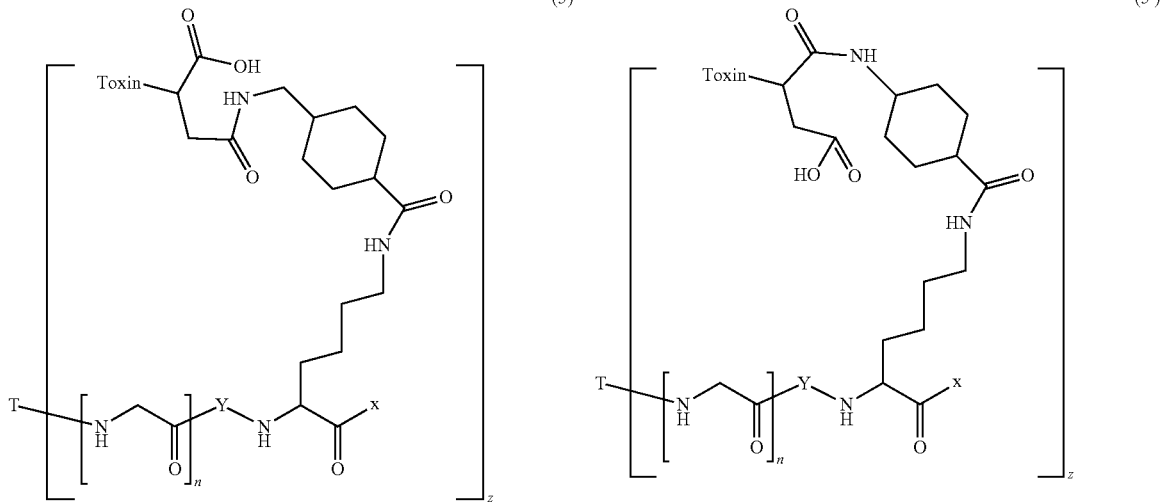

(5) (5')

wherein n is an integer of 3-10;
x is OH, NH$_2$ or Gly;
Toxin represents a cytotoxin;
Lk is L$_1$-L$_2$-L$_3$;
L$_1$ and L$_3$ are each independently selected from the group consisting of:
—CH$_2$—, —NH—, —(CO)—, —NH(CO)—, —(CO)NH—; and combination of a C1-4 alkylene with one of the following groups: —CH$_2$—, —NH—, —(CO)—, —NH(CO)—, —(CO)NH—;
L$_2$ is absent or is a C$_{7-34}$ alkylene, and wherein one or more (—CH$_2$—) structures in the alkylene is optionally replaced by —O—;
L$_1$, L$_2$ and L$_3$ are each optionally and independently substituted with 1, 2 or 3 substituents selected from [[—OR1[[—OR$_1$ and —NR$_1$R$_2$;

R$_1$ and R$_2$ are each independently selected from the group consisting of hydrogen, —C$_{1-6}$ alkyl, —(CO)—C$_{1-6}$ alkyl and —S(=O)$_2$—C$_{1-6}$ alkyl;
Y is absent or selected from the group consisting of a cleavable sequence, spacer Sp1, and a combination thereof;
the cleavable sequence comprises an amino acid sequence which can be cleaved by an enzyme, and the cleavable sequence comprises 1-10 amino acids; and
Sp1 is selected from the group consisting of a spacer sequence containing 1-20 amino acids, PAB, and a combination thereof.

15. The process according to claim 14, wherein Y does not exist, and the conjugate has the structure selected from the following formulae (4), (4'), (6) and (6'):

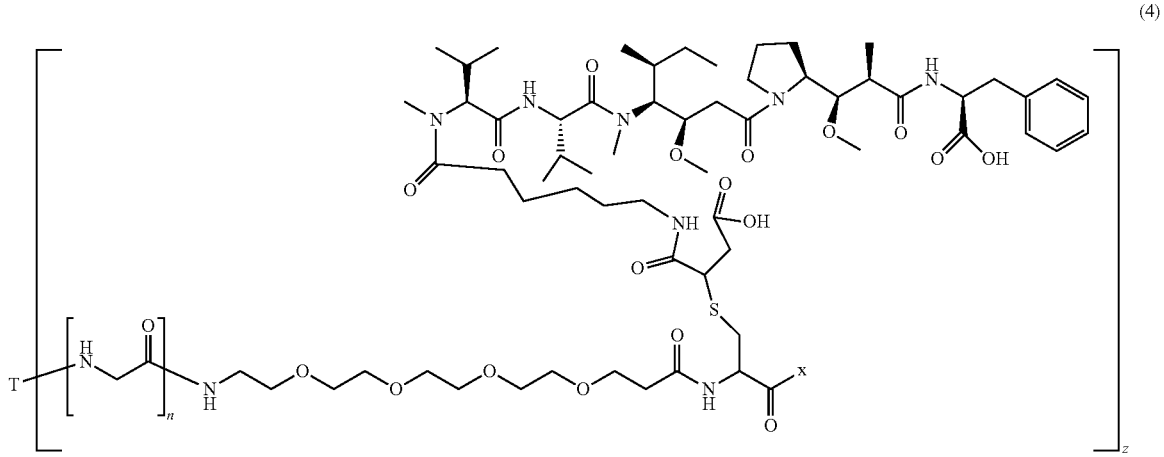

(4)

-continued
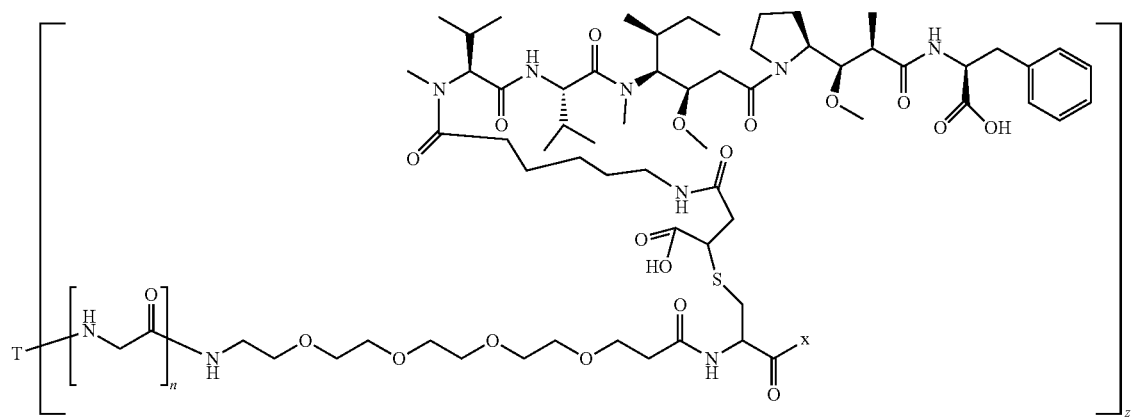
(4')
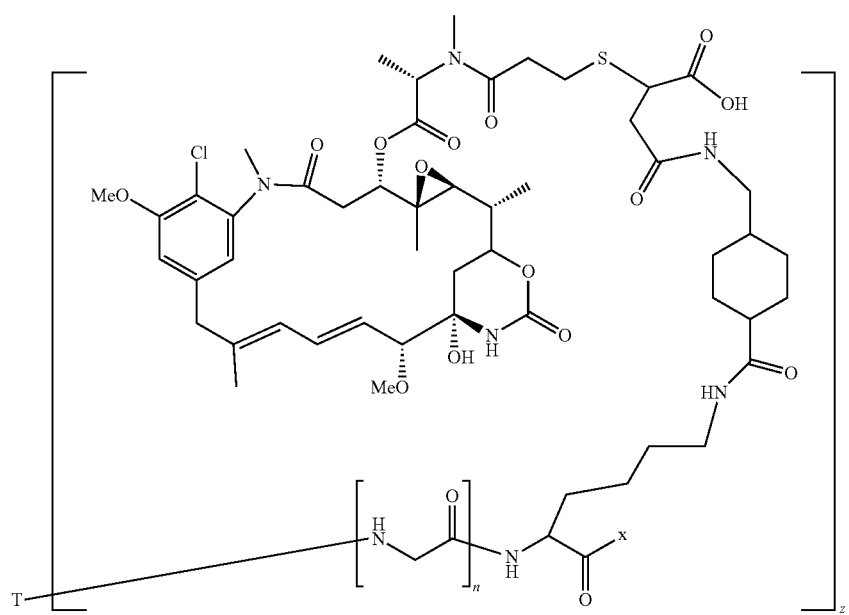
(6)

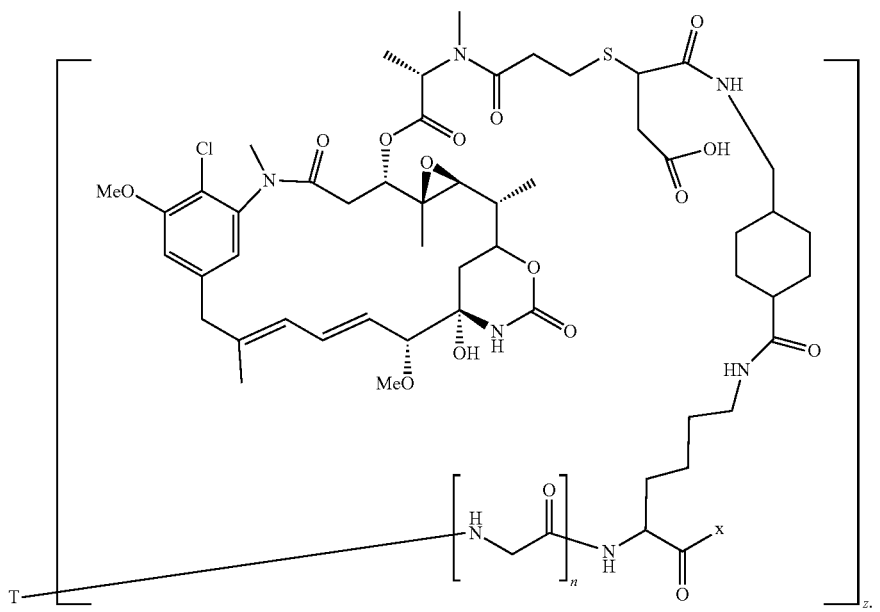

16. A process for the preparation of a conjugate, comprising contacting a ligase unit with a linker-payload intermediate and T to catalyze the conjugation reaction between T and the linker-payload intermediate to obtain the conjugate,

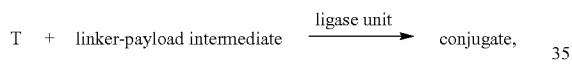

wherein the ligase unit comprises a ligase fusion protein immobilized to a support comprising a ligase which is a sortase and a Halo tag;
wherein the ligase fusion protein has an isoelectric point (pI) that is lower than that of the ligase from which the ligase fusion protein is derived;
wherein the linker-payload intermediate has the structure of formula (IV-1-5) or (IV-1-5'), the conjugate has the structure of formula (5) or (5'), and the formulae (IV-1-5), (IV-1-5'), (5) and (5') are as follows

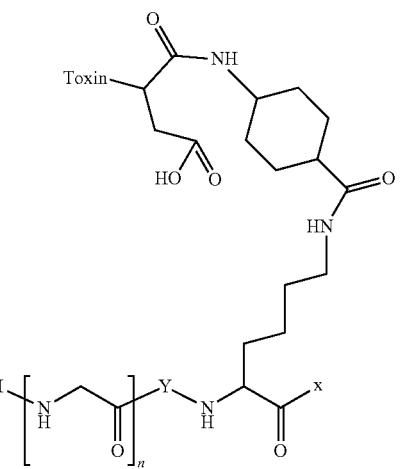

(5')

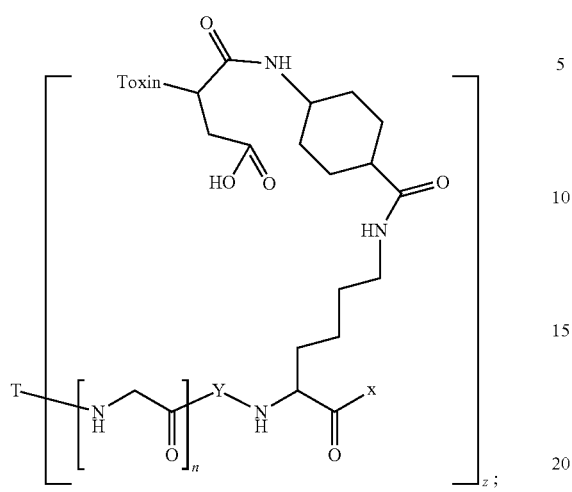

wherein T a protein, a peptide, an antibody, or an antibody fragment, which is optionally modified to have the recognition motif of the ligase donor substrate;

n is an integer of 3-10; and

Toxin represents a cytotoxin.

17. The process according to claim 16, wherein the linker-payload intermediate of formula (IV-1-5) has the structure of formula (IV-1-6), the linker-payload intermediate of formula (IV-1-5') has the structure of formula (IV-1-6'), the conjugate of formula (5) has the structure of formula (6), and the conjugate of formula (5') has the structure of formula (6'), and the formulae (IV-1-6), (IV-1-6'), (6) and (6') are as follows

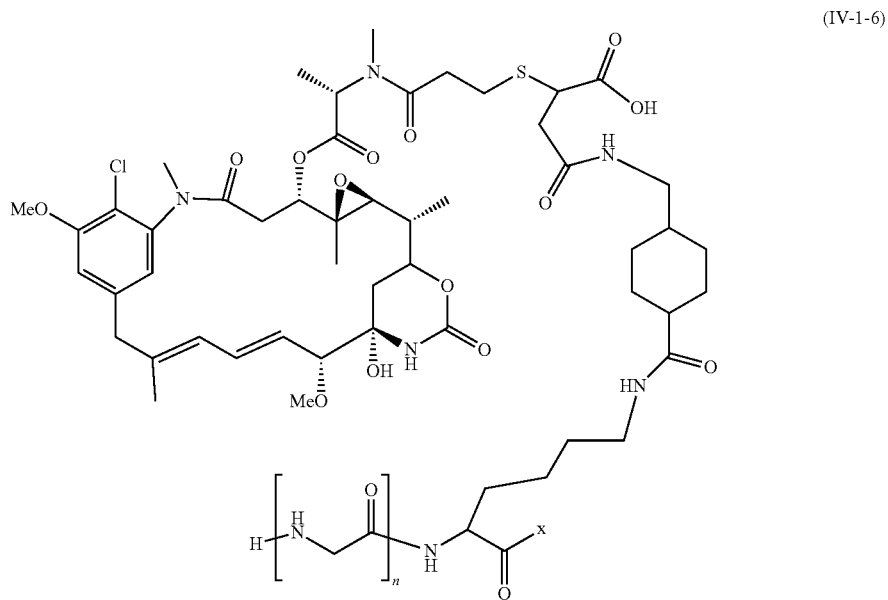

(IV-1-6)

-continued
(IV-1-6′)
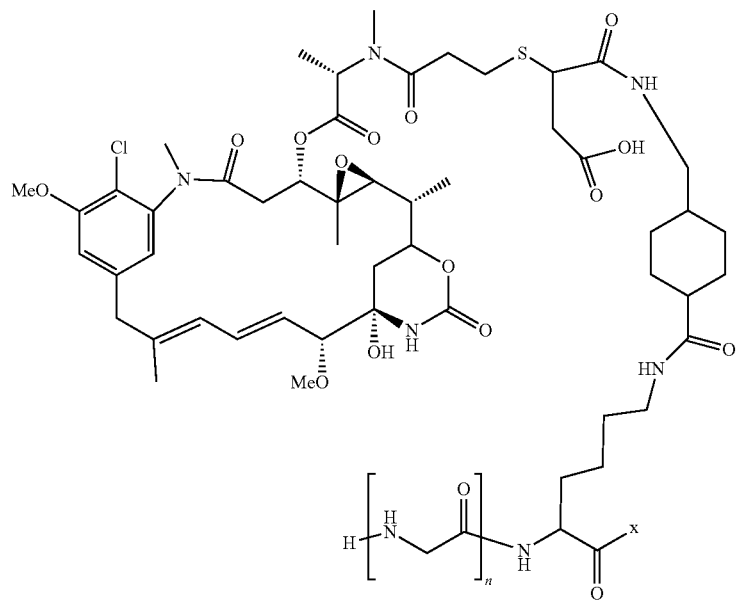
(6)
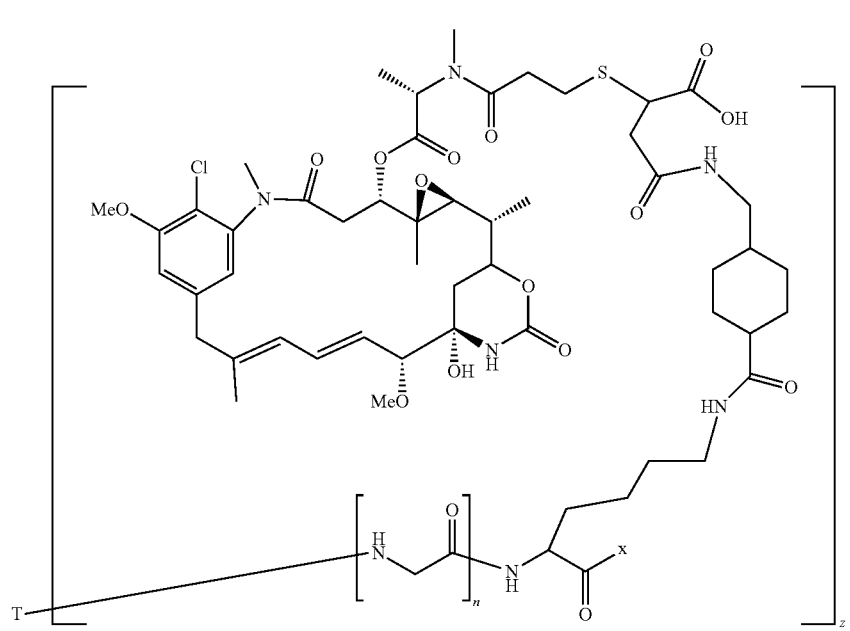

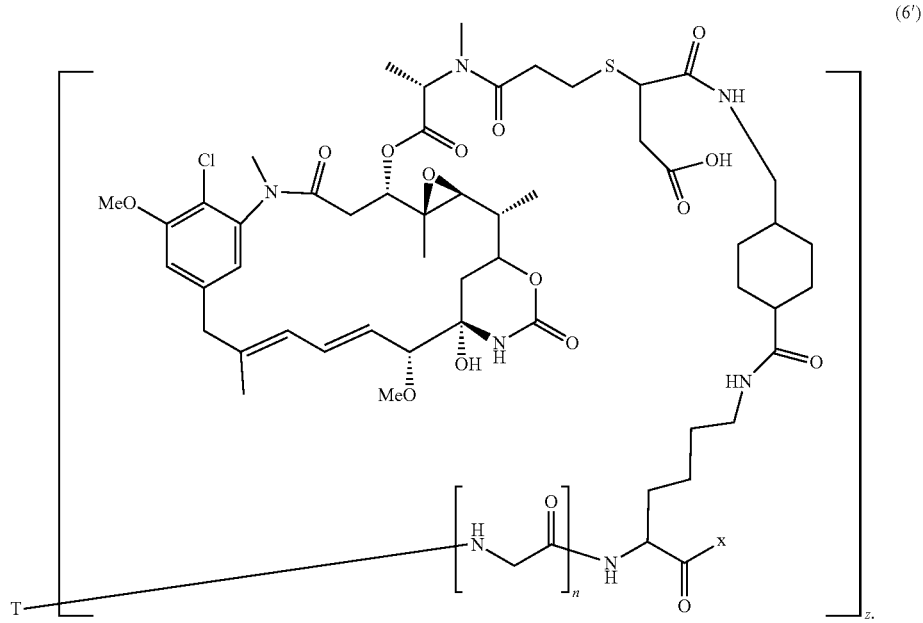

(6')

18. The process according to claim 5, wherein the haloalkane linker is a chloroalkane linker produced by a chloroalkyl substrate having the structure of formula (I-1):

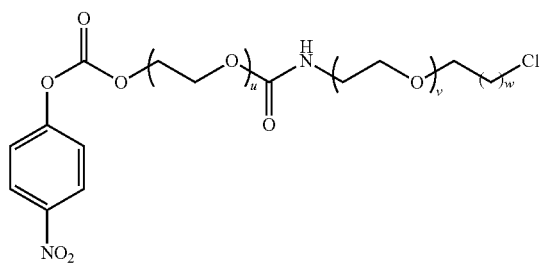

(I-1)

wherein u is an integer of 1 to 20, v is an integer of 0 to 20, and w is an integer of 1 to 19.

19. The process according to claim 1, wherein the ligase fusion protein comprises a ligase, a Halo tag, and optionally a linker peptide, wherein the ligase, the Halo tag, and optionally the linker peptide are fused by a covalent bond, wherein the ligase is a sortase A comprising the amino acid sequence of SEQ ID NO:27 or an amino acid sequence having a sequence identity of at least 85% thereto, and wherein the ligase has an isoelectric point (pI) of about 7.5 to about 10.0, the Halo tag has an isoelectric point of about 4.5 to about 5.0, and the pI of the ligase fusion protein is about 2.0 to about 4.5 pH units lower than that of the ligase.

20. The process according to claim 19, wherein the Halo tag comprises the amino acid sequence of SEQ ID NO: 28 or an amino acid sequence having a sequence identity of at least about 85% thereto.

21. The process according to claim 19, wherein the pI of the ligase fusion protein is about 4.5 to about 6.5.

22. The process according to claim 21, wherein the pI of the ligase fusion protein is about 5.0 to about 6.0.

23. The process according to claim 19, wherein the ligase fusion protein comprises the amino acid sequence of SEQ ID NO: 29.

24. The process according to claim 16, wherein the support comprises a haloalkyl linker such that the ligase fusion protein is immobilized on the support through covalent interaction between the haloalkyl linker and the Halo tag, wherein the haloalkane linker is a chloroalkane linker produced by a chloroalkyl substrate having the structure of formula (I-1):

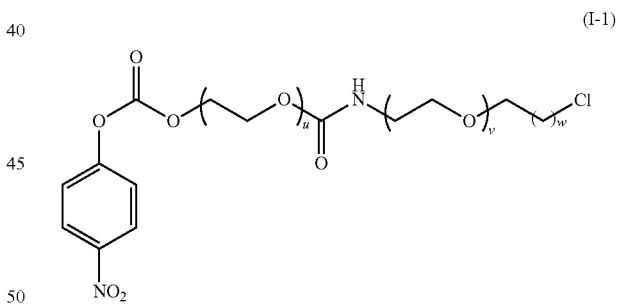

(I-1)

wherein u is an integer of 1 to 20, v is an integer of 0 to 20, and w is an integer of 1 to 19.

25. The process according to claim 24, wherein the ligase fusion protein comprises a ligase, a Halo tag, and optionally a linker peptide, wherein the ligase, the Halo tag, and optionally the linker peptide are fused by a covalent bond, wherein the ligase is a sortase A comprising the amino acid sequence of SEQ ID NO:27 or an amino acid sequence having a sequence identity of at least 85% thereto, and wherein the ligase has an isoelectric point (pI) of about 7.5 to about 10.0, the Halo tag has an isoelectric point of about 4.5 to about 5.0, and the pI of the ligase fusion protein is about 2.0 to about 4.5 pH units lower than that of the ligase.

26. The process according to claim 25, wherein the ligase fusion protein comprises the amino acid sequence of SEQ ID NO: 29.

27. The process according to claim 15, wherein the conjugate has the structure selected from the following formulae (6) and (6'):
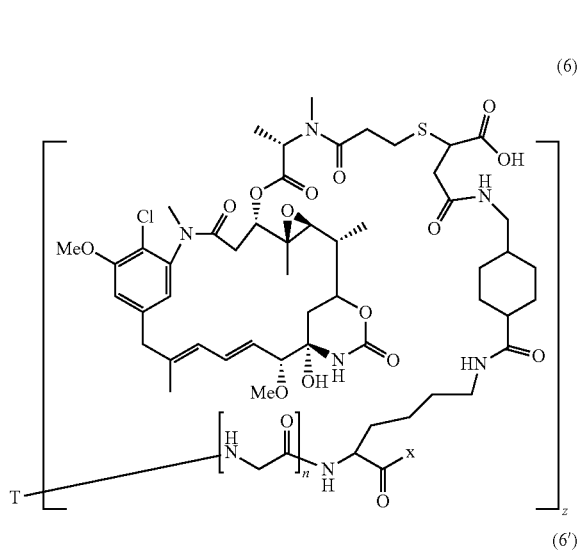
(6)
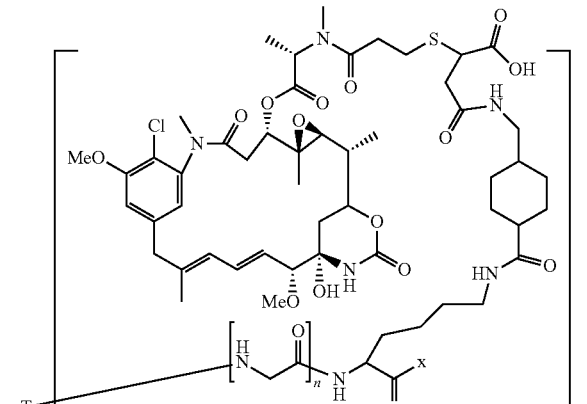
(6)
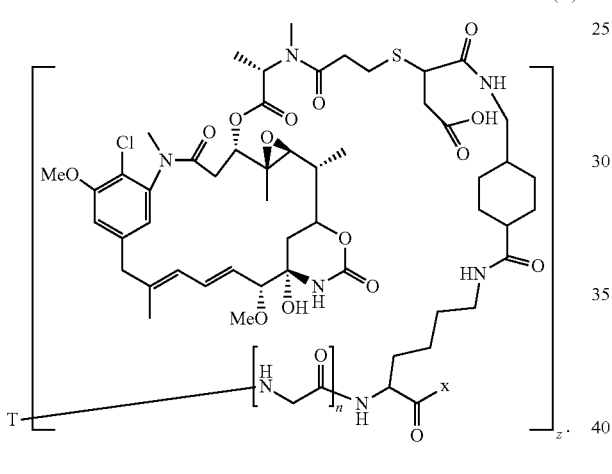
(6')
28. The process according to claim 26, wherein the conjugate has the structure selected from the following formulae (6) and (6'):
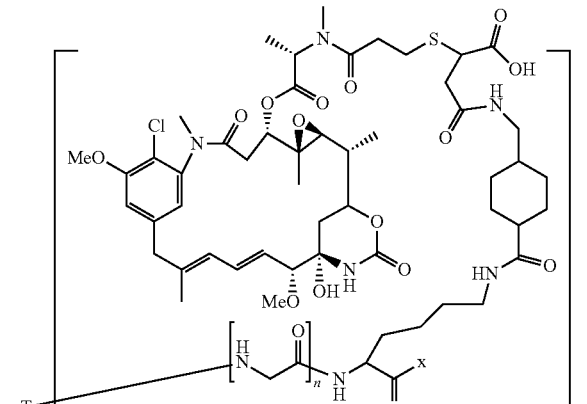
(6')
* * * * *

UNITED STATES PATENT AND TRADEMARK OFFICE
CERTIFICATE OF CORRECTION

| | | |
|---|---|---|
| PATENT NO. | : 11,834,688 B2 | Page 1 of 1 |
| APPLICATION NO. | : 17/815371 | |
| DATED | : December 5, 2023 | |
| INVENTOR(S) | : Gang Qin et al. | |

It is certified that error appears in the above-identified patent and that said Letters Patent is hereby corrected as shown below:

In the Claims

In Column 101, Line 40, in Claim 14:
"[[-OR1[[-OR$_1$" should be corrected to "-OR$_1$".

Signed and Sealed this
Second Day of April, 2024

Katherine Kelly Vidal
*Director of the United States Patent and Trademark Office*

SEQUENCE LISTING

```
Sequence total quantity: 29
SEQ ID NO: 1            moltype = AA  length = 146
FEATURE                 Location/Qualifiers
REGION                  1..146
                        note = sortase A
source                  1..146
                        mol_type = protein
                        organism = synthetic construct
SEQUENCE: 1
AKPQIPKDKS KVAGYIEIPD ADIKEPVYPG PATPEQLNRG VSFAEENESL DDQNISIAGH   60
TFIDRPNYQF TNLKAAKKGS MVYFKVGNET RKYKMTSIRD VKPTDVGVLD EQKGKDKQLT  120
LITCDDYNEK TGVWEKRKIF VATEVK                                      146

SEQ ID NO: 2            moltype = AA  length = 146
FEATURE                 Location/Qualifiers
REGION                  1..146
                        note = sortase A
source                  1..146
                        mol_type = protein
                        organism = synthetic construct
SEQUENCE: 2
KTPEIPKDKS KMAGYIKVPD AEIEEPVYPG PATPEQLNRG VSFAEGNESL SDQNISIAGH   60
TFTDRPHYQF TNLKAAKKGS KVYFKVGNET RKYKMTSIRD VDPSDVKVLD EHKGEKNQLT  120
LITCDNYNKE TGVWEKRKIF VAKEIK                                      146

SEQ ID NO: 3            moltype = AA  length = 146
FEATURE                 Location/Qualifiers
REGION                  1..146
                        note = sortase A
source                  1..146
                        mol_type = protein
                        organism = synthetic construct
SEQUENCE: 3
KAPAIPKDKS KMAGYIKVPD AEIEEPVYPG PATPEQLNRG VSFAEGNESL TDQNISIAGH   60
TFTDRPHYQF TNLKAAKKGS KVYFKVGNET RKYKMTSIRN VDPSDVKVLD EHKGEKNQLT  120
LITCDNYNKN TGVWEKRKIF VAKQIN                                      146

SEQ ID NO: 4            moltype = AA  length = 146
FEATURE                 Location/Qualifiers
REGION                  1..146
                        note = sortase A
source                  1..146
                        mol_type = protein
                        organism = synthetic construct
SEQUENCE: 4
KTPTIPKDKS KMAGYIEVPD AEIKEPVYPG PATLEQLNRG VSFAEGDESL DQQNISIAGH   60
TFTDRPHYQF TNLKAAKKGS KVYFKVGNQT RKYKMTKIHD VNPSDVEVLD EQKGKKNQLT  120
LITCDDYNEK TGVWEKRKIF IATQVN                                      146

SEQ ID NO: 5            moltype = AA  length = 146
FEATURE                 Location/Qualifiers
REGION                  1..146
                        note = sortase A
source                  1..146
                        mol_type = protein
                        organism = synthetic construct
SEQUENCE: 5
KAVEIPKDKS KMAGYIKIPD AEIEEPVYPG PATPEQLNRG VSFAEGNESL SDQNISIAGH   60
TFTDRPHYQF TNLKAAKKGS KVYFKVGNET RKYKMTSIRD VDPSDVKVLD EHKGEKNQLT  120
LITCDNYNKE TGVWEKRKIF VAKEIK                                      146

SEQ ID NO: 6            moltype = AA  length = 146
FEATURE                 Location/Qualifiers
REGION                  1..146
                        note = sortase A
source                  1..146
                        mol_type = protein
                        organism = synthetic construct
SEQUENCE: 6
KAPEIPKDKS KMAGYIKVPD AEIEEPVYPG PATPEQLNRG VSFAEGNESL TDQNISIAGH   60
TFTDRPHYQF TNLKAAKKGS KVYFKVGNET RKYKMTSIRD VDPSDVKVLD EHKGEKNQLT  120
LITCDNYNKN TGVWEKRKIF VAKQIN                                      146

SEQ ID NO: 7            moltype = AA  length = 146
FEATURE                 Location/Qualifiers
REGION                  1..146
                        note = sortase A
source                  1..146
```

```
                        mol_type = protein
                        organism = synthetic construct
SEQUENCE: 7
KKPTIPKDKS KMAGYIEVPD AEIKEPVYPG PATPEQLNRG VSFAEGDESL DQQNIAIAGH    60
TFTDRPHYQF TNLKAAKKGS KVYFKVGNEV RKYKMTKIHD VDPTEVKVLD EHKGKKNQLT   120
LITCDDYNEQ TGVWEKRKIF VATQVN                                        146

SEQ ID NO: 8            moltype = AA  length = 146
FEATURE                 Location/Qualifiers
REGION                  1..146
                        note = sortase A
source                  1..146
                        mol_type = protein
                        organism = synthetic construct
SEQUENCE: 8
KAVEIPKDKS KMVGYIKVPD AEIEEPVYPG PATPEQLNRG VSFAEGNESL SDQNISIAGH    60
TFTDRPHYQF TNLKAAKKGS KVYFKVGNET RKYKMTSIRD VDPSDVKVLD EHKGEKNQLT   120
LITCDNYNKE TGVWEKRKIF VAKEIK                                        146

SEQ ID NO: 9            moltype = AA  length = 146
FEATURE                 Location/Qualifiers
REGION                  1..146
                        note = sortase A
source                  1..146
                        mol_type = protein
                        organism = synthetic construct
SEQUENCE: 9
ESPQIPKDKA KMAGYIEIPD AQIKEPVYPG PATPQQLNRG VSFAEGDESL NQQNISIAGH    60
TFTDRPHYQF TNLKAAKKGS KVYFKVGNQT RKYKITKIHD VKPTEVKVLD EHPSKKNQLT   120
LITCDDYNEQ TGVWETRKIF VATQMN                                        146

SEQ ID NO: 10           moltype = AA  length = 146
FEATURE                 Location/Qualifiers
REGION                  1..146
                        note = sortase A
source                  1..146
                        mol_type = protein
                        organism = synthetic construct
SEQUENCE: 10
STPKIPSDKS KMAGYIEVPD AQIKEPVYPG PATPEQLNRG VSFAEGDESL NQQNISIAGH    60
TFTDRPHYQF TNLKSAKIGS KVYFKTGNQT RKYKITKIRD VKPTEVKVLD EHPNKKNQLT   120
LITCDDYNEE TGVWETRKIF IATQIN                                        146

SEQ ID NO: 11           moltype = AA  length = 146
FEATURE                 Location/Qualifiers
REGION                  1..146
                        note = sortase A
source                  1..146
                        mol_type = protein
                        organism = synthetic construct
SEQUENCE: 11
ERPQIPKDKA KMAGYIEIPD AQIKEPVYPG PATPQQLNRG VSFAEGDESL YQQNISIAGH    60
TFTDRPHYQF TNLKAAKKGS KVYFKVRNQT RKYKITKIHD VKPTEVKVLD EHPSKKNQLT   120
LITCDDYNEQ TGVWETRKIF VATQMN                                        146

SEQ ID NO: 12           moltype = AA  length = 146
FEATURE                 Location/Qualifiers
REGION                  1..146
                        note = sortase A
source                  1..146
                        mol_type = protein
                        organism = synthetic construct
SEQUENCE: 12
STPKIPSDKS KMAGYIEVPD AQIKEPVYPG PATPEQLNRG VSFAEGDESL NQQNISIAGH    60
TFTDRSHYQF TNLKSAKIGS KVYFKTGNQT RKYKITKIRD VKPTEVKVLD EHPNKKNQLT   120
LITCDDYNEE TGVWETRKIF IATQIN                                        146

SEQ ID NO: 13           moltype = AA  length = 146
FEATURE                 Location/Qualifiers
REGION                  1..146
                        note = sortase A
source                  1..146
                        mol_type = protein
                        organism = synthetic construct
SEQUENCE: 13
EKPTISKDKS KMTGYISIPD ADIKEPVYPG PATPEQLNRG VSFAEEDESL DDQNISIAGH    60
TFIDRPNYQF TNLKAAKKGS KVTFKIGNET RKYKMTSIRD VNPEDVEVLD EHKGKKNQLT   120
LITCDDYNEN TGVWEKRKIF VAEEVK                                        146
```

```
SEQ ID NO: 14              moltype = AA  length = 146
FEATURE                    Location/Qualifiers
REGION                     1..146
                           note = sortase A
source                     1..146
                           mol_type = protein
                           organism = synthetic construct
SEQUENCE: 14
EKPTISKDKS KMTGYISIPD ADIKEPVYPG PATPEQLNRG VSFAEEDESL DDQNISIAGH  60
TFTDRPNYQF TNLKAAKKGS KVTFKIGNET RKYKMTSIRD VDPDAVEVLD ENKGKKNQLT 120
LITCDDYNEN TGVWEKRKIF VAEQIK                                     146

SEQ ID NO: 15              moltype = AA  length = 146
FEATURE                    Location/Qualifiers
REGION                     1..146
                           note = sortase A
source                     1..146
                           mol_type = protein
                           organism = synthetic construct
SEQUENCE: 15
EKPTISKDKS KMTGYISIPD ADIKEPVYPG PATPEQLNRG VSFAEEDESL DDQNISIAGH  60
TFTDRPNYQF TNLKAAKKGS KVTFKTGNET RKYKMTSIRD VDPDAVEVLD ENKGKKNQLT 120
LITCDDYNEN TGVWEKRKIF VAEQIK                                     146

SEQ ID NO: 16              moltype = AA  length = 146
FEATURE                    Location/Qualifiers
REGION                     1..146
                           note = sortase A
source                     1..146
                           mol_type = protein
                           organism = synthetic construct
SEQUENCE: 16
ETPTIPKDKS KMAGYISIPD AEIKEPVYPG PATPEQLNRG VSFAEEDEKL DDQNISIAGH  60
TFIDRPHYQF TNLKAAKKGS KVYFKVGNET RKYKMTSIRD VNPDDVKVLD EHKGETNQLT 120
LITCDNYNEQ TGIWEKRKIF VAKQIN                                     146

SEQ ID NO: 17              moltype = AA  length = 146
FEATURE                    Location/Qualifiers
REGION                     1..146
                           note = sortase A
source                     1..146
                           mol_type = protein
                           organism = synthetic construct
SEQUENCE: 17
ETPTIPKDKS KMAGYISIPD AEIKEPVYPG PATPEQLDRG VSFAEEDEKL DDQNISIAGH  60
TFIDRPHYQF TNLKAAKKGS KVYFKVGNET RKYKMTSIRD VNPDDVKVLD EHKGETNQLT 120
LITCDNYNEQ TGIWEKRKIF IAKQIN                                     146

SEQ ID NO: 18              moltype = AA  length = 146
FEATURE                    Location/Qualifiers
REGION                     1..146
                           note = sortase A
source                     1..146
                           mol_type = protein
                           organism = synthetic construct
SEQUENCE: 18
EKPTIPKDKS KMAGYISVPD AEIKEPVYPG PATPEQLNRG VSFAEGDESL DDQNISIAGH  60
TFTDRPHYQF TNLKAAKKGS KVYFKVGDET REYKMTSIRD VDPEDVQVLD EHKGETNQLT 120
LITCDNYNQQ TGVWEKRKIF VAKQIK                                     146

SEQ ID NO: 19              moltype = AA  length = 146
FEATURE                    Location/Qualifiers
REGION                     1..146
                           note = sortase A
source                     1..146
                           mol_type = protein
                           organism = synthetic construct
SEQUENCE: 19
ERPTIPKNKS EMAGYISIPD AEIKEPVYPG PATLEQLNRG VSFAEGDESL DDQNISIAGH  60
TFTDRPHYQF TNLKAAKKGS KVYFKVGDET REYKMTSIRD VDPEDVQVLD EHKGETNQLT 120
LITCDNYNQQ TGVWEKRKIF VAKQIK                                     146

SEQ ID NO: 20              moltype = AA  length = 146
FEATURE                    Location/Qualifiers
REGION                     1..146
                           note = sortase A
source                     1..146
                           mol_type = protein
                           organism = synthetic construct
```

```
SEQUENCE: 20
QTPTIPKDKS KMAGYISVPD AEIKEPVYPG PATPEQLNRG VSFAEEDESL SDQNISIAGH    60
TFTDRPHYQF TNLKAAKKGS KVYFKIGNET REYKMTSIRD VNPDQVEVLN EHKGEKNQLT   120
LITCDDYNEQ TGVWEKRKIF VAKQVK                                       146

SEQ ID NO: 21          moltype = AA   length = 146
FEATURE                Location/Qualifiers
REGION                 1..146
                       note = sortase A
source                 1..146
                       mol_type = protein
                       organism = synthetic construct
SEQUENCE: 21
QTPTIPKDKT KMAGYISVPD AEIKEPVYPG PATPEQLNRG VSFAEKDESL SDQNISIAGH    60
TFTDRPHYQF TNLKAAKKGS KVYFKIGNET REYKMTSIRD VNPDEVEVLD EHKGEKNQLT   120
LITCDDYNEQ TGVWEKRKIF VAKQVK                                       146

SEQ ID NO: 22          moltype = AA   length = 146
FEATURE                Location/Qualifiers
REGION                 1..146
                       note = sortase A
source                 1..146
                       mol_type = protein
                       organism = synthetic construct
SEQUENCE: 22
ERPTIPKDKS KMAGYISVPD AEIKEPVYPG PATLEQLNRG VSFAEGDESL DDQNISIAGH    60
TFTDRPHYQF TNLKAAKKGS KVYFKVGDET REYKMTSIRD VNPEDVQVLD EHEGETNQLT   120
LITCDNYNQQ TGVWEKRKIF VAKQIK                                       146

SEQ ID NO: 23          moltype = AA   length = 146
FEATURE                Location/Qualifiers
REGION                 1..146
                       note = sortase A
source                 1..146
                       mol_type = protein
                       organism = synthetic construct
SEQUENCE: 23
QTPTIPKDKT KMAGYISVPD AEIKEPVYPG PATPEQLNRG VSFAEKDESL SDQNISIAGH    60
TFTDRPHYQF TNLKAAKKGS KVYFKIGNET REYKMTSIRD VNPDEVEVLD EHKGEKNQLT   120
LITCDDYNEQ TGVWEKRKIF VAKQVN                                       146

SEQ ID NO: 24          moltype = AA   length = 146
FEATURE                Location/Qualifiers
REGION                 1..146
                       note = sortase A
source                 1..146
                       mol_type = protein
                       organism = synthetic construct
SEQUENCE: 24
DKPTIPKDKA EMAGYLRIPD ADINEPVYPG PATPEQLNRG VSFAEEQESL DDQNIAIAGH    60
TYIGRPHYQF TNLKAAKKGS KVYFKVGNET REYKMTTIRD VNPDEIDVLD EHRGDKNRLT   120
LITCDDYNEK TGVWEKRKIF IAEQIK                                       146

SEQ ID NO: 25          moltype = AA   length = 146
FEATURE                Location/Qualifiers
REGION                 1..146
                       note = sortase A
source                 1..146
                       mol_type = protein
                       organism = synthetic construct
SEQUENCE: 25
QTPTIPKDKT KMAGYISVPD AEIKEPVYPG PATPEQLNRG VSFTEKDESL SDQNISIAGH    60
TFTDRPHYQF TNLKAAKKGS KVYFKIGNET REYKMTSIRD VNPDEVEVLD EHKGEKNQLT   120
LITCDDYNEQ TGVWEKRKIF VAKQVN                                       146

SEQ ID NO: 26          moltype = AA   length = 146
FEATURE                Location/Qualifiers
REGION                 1..146
                       note = sortase A
source                 1..146
                       mol_type = protein
                       organism = synthetic construct
SEQUENCE: 26
DKPTIPKDKA EMAGYLRIPD ADINEPVYPG PATPEQLNRG VSFAEEQESL DDQNIAIAGH    60
TYIGRPHYQF TNLKAAKKGS KVYFKVGNET REYKMTTIRD VDPDEIDVLD EHRGDKNRLT   120
LITCDDYNEK TGVWEKRKIF IAEQIK                                       146

SEQ ID NO: 27          moltype = AA   length = 146
FEATURE                Location/Qualifiers
```

```
REGION              1..146
                    note = sortase A, SNAT counterpart of SEQ ID NO: 1
source              1..146
                    mol_type = protein
                    organism = synthetic construct
SEQUENCE: 27
AKPQIPKDKS KVAGYIEIPD ADIKEPVYPG PATSEQLNRG VSFAEENESL DDQNISIAGH    60
TFIDRPNYQF TNLKAAKKGS MVYFKVGNET RKYKMTSIRN VKPTAVGVLD EQKGKDKQLT   120
LITCDDYNEK TGVWETRKIF VATEVK                                        146

SEQ ID NO: 28       moltype = AA  length = 297
FEATURE             Location/Qualifiers
REGION              1..297
                    note = Halo tag
source              1..297
                    mol_type = protein
                    organism = synthetic construct
SEQUENCE: 28
MAEIGTGFPF DPHYVEVLGE RMHYVDVGPR DGTPVLFLHG NPTSSYVWRN IIPHVAPTHR    60
CIAPDLIGMG KSDKPDLGYF FDDHVRFMDA FIEALGLEEV VLVIHDWGSA LGFHWAKRNP   120
ERVKGIAFME FIRPIPTWDE WPEFARETFQ AFRTTDVGRK LIIDQNVFIE GTLPMGVVRP   180
LTEVEMDHYR EPFLNPVDRE PLWRFPNELP IAGEPANIVA LVEEYMDWLH QSPVPKLLFW   240
GTPGVLIPPA EAARLAKSLP NCKAVDIGPG LNLLQEDNPD LIGSEIARWL STLEISG      297

SEQ ID NO: 29       moltype = AA  length = 453
FEATURE             Location/Qualifiers
REGION              1..453
                    note = Halo-Sortase
source              1..453
                    mol_type = protein
                    organism = synthetic construct
SEQUENCE: 29
MAEIGTGFPF DPHYVEVLGE RMHYVDVGPR DGTPVLFLHG NPTSSYVWRN IIPHVAPTHR    60
CIAPDLIGMG KSDKPDLGYF FDDHVRFMDA FIEALGLEEV VLVIHDWGSA LGFHWAKRNP   120
ERVKGIAFME FIRPIPTWDE WPEFARETFQ AFRTTDVGRK LIIDQNVFIE GTLPMGVVRP   180
LTEVEMDHYR EPFLNPVDRE PLWRFPNELP IAGEPANIVA LVEEYMDWLH QSPVPKLLFW   240
GTPGVLIPPA EAARLAKSLP NCKAVDIGPG LNLLQEDNPD LIGSEIARWL STLEISGGGG   300
GSGGGGSAKP QIPKDKSKVA GYIEIPDADI KEPVYPGPAT SEQLNRGVSF AEENESLDDQ   360
NISIAGHTFI DRPNYQFTNL KAAKKGSMVY FKVGNETRKY KMTSIRNVKP TAVGVLDEQK   420
GKDKQLTLIT CDDYNEKTGV WETRKIFVAT EVK                                453
```